(12) United States Patent
Andresen et al.

(10) Patent No.: US 10,561,746 B2
(45) Date of Patent: Feb. 18, 2020

(54) GEL FORMULATIONS FOR GUIDING RADIOTHERAPY

(71) Applicants: DANMARKS TEKNISKE UNIVERSITET, Kgs. Lyngby (DK); NANOVI RADIOTHERAPY APS, Kgs. Lyngby (DK)

(72) Inventors: Thomas Lars Andresen, Vanlose (DK); Rasmus Irming Jolck, Kgs. Lyngby (DK); Morten Albrechtsen, Charlottenlund (DK)

(73) Assignees: Danmarks Tekniske Universitet, Kgs. Lyngby (DK); Nanovi Radiotherapy APS, Kgs. Lyngby (DK)

( * ) Notice: Subject to any disclaimer, the term of this patent is extended or adjusted under 35 U.S.C. 154(b) by 791 days.

(21) Appl. No.: 14/892,811

(22) PCT Filed: May 23, 2014

(86) PCT No.: PCT/EP2014/060673
§ 371 (c)(1),
(2) Date: Nov. 20, 2015

(87) PCT Pub. No.: WO2014/187962
PCT Pub. Date: Nov. 27, 2014

(65) Prior Publication Data
US 2016/0089454 A1    Mar. 31, 2016

(30) Foreign Application Priority Data

May 24, 2013   (SE) ...................................... 1350637

(51) Int. Cl.
| | | |
|---|---|---|
| *A61K 49/04* | (2006.01) | |
| *A61B 6/00* | (2006.01) | |
| *A61K 49/18* | (2006.01) | |
| *A61K 51/00* | (2006.01) | |
| *A61N 5/10* | (2006.01) | |

(52) U.S. Cl.
CPC .......... *A61K 49/0438* (2013.01); *A61B 6/481* (2013.01); *A61K 49/04* (2013.01); *A61K 49/1806* (2013.01); *A61K 51/00* (2013.01); *A61N 5/10* (2013.01)

(58) Field of Classification Search
None
See application file for complete search history.

(56) References Cited

U.S. PATENT DOCUMENTS

| | | |
|---|---|---|
| 2005/0036946 A1 | 2/2005 | Pathak et al. |
| 2005/0119746 A1 | 6/2005 | Lidgren |
| 2009/0110644 A1 | 4/2009 | Margel et al. |
| 2009/0263455 A1* | 10/2009 | Zanella ................ A61K 9/0024 424/426 |
| 2010/0290995 A1 | 11/2010 | Pathak et al. |
| 2010/0297007 A1 | 11/2010 | Lanza et al. |
| 2011/0104052 A1 | 5/2011 | Barnett et al. |
| 2011/0142936 A1 | 6/2011 | Campbell et al. |
| 2012/0039814 A1 | 2/2012 | Sample et al. |
| 2012/0065614 A1 | 3/2012 | Omary et al. |

FOREIGN PATENT DOCUMENTS

| | | | |
|---|---|---|---|
| EP | 1006935 A1 | 6/2000 | |
| GB | 1400985 A | 7/1975 | |
| JP | 2006523507 A | 10/2006 | |
| JP | 2009515669 A | 4/2009 | |
| JP | 2011518164 A | 6/2011 | |
| RU | 2207808 | 7/2003 | |
| WO | 9403155 A1 | 2/1992 | |
| WO | 9519184 A1 | 7/1995 | |
| WO | 2006/124021 | 11/2006 | |
| WO | WO-2012007567 A1 * | 1/2012 | ............ A61B 6/037 |
| WO | 2013/076305 A1 | 5/2013 | |
| WO | 2014/187962 A1 | 11/2014 | |

OTHER PUBLICATIONS

Agarawal et al. The role of external beam radiotherapy in the management of bone metastases. 2006 Clin. Oncol. 18: 747-760. (Year: 2006).*
Jing, B., et al., "Sol-Gel-Sol Transition of gold Nanoparticle-Based Supramolecular Hydrogels Induced by Cyclodextrin Inclusion", ChemPhysChem, 2008, vol. 9, pp. 249-252.
Kim, Jun-Hyun and Lee, T. Randall, "Thermo- and pH-Responsive Hydrogel-Coated Gold Nanoparticles", Chem. Mater., 2004, vol. 16, pp. 3647-3651.
Lahoti, S, et at., "PH triggered sol-gel transition system of ofloxacin for prolonged gastric retention", Pelagia Research Library, 2011, vol. 5, pp. 235-250.
International-Type Search Report dated Jan. 17, 2014 for National Application No. SE1350637-3, 7 pages.
International Search Report dated Aug. 26, 2014 for International Patent Application No. PCT/EP/2014/060673, 4 pages.
Lu, et al., "Rheological properties of sucrose acetate isobutyrate in situ gel," Acta Pharmaceutica Sinica, 2007, 42(4). pp. 445-449, Abstract only in English.
Hill et al., "In Vitro Assessment of Poly-iodinated Triglyceride Reconstituted Low-Density Lipoprotein: Initial Steps Toward CT Molecular Imaging", Academic Radiology, Nov. 2010, vol. 17, pp. 1359-1365.

* cited by examiner

Primary Examiner — Jennifer A. Lamberski
(74) Attorney, Agent, or Firm — Finch & Maloney PLLC

(57) ABSTRACT

The present invention describes an X-ray contrast composition for local administration, wherein the X-ray contrast composition exhibits contrast properties and wherein at least 60% of an administrated amount of said X-ray contrast composition remains more than 24 hours within 10 cm from an injection point when the X-ray contrast composition is administrated to a human or animal body.

16 Claims, 10 Drawing Sheets

Gelling mechanisms

Figure 1:
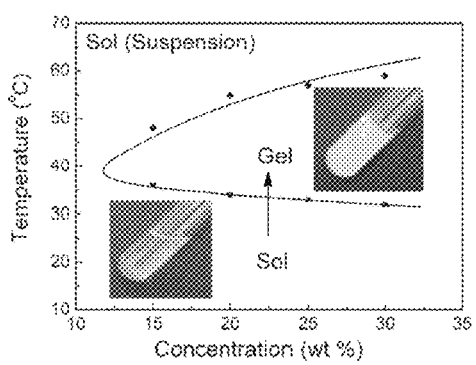
Figure 1:
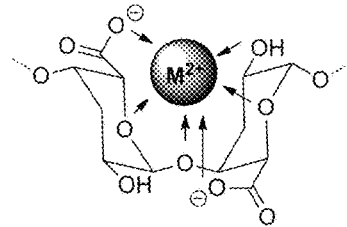
Figure 1:
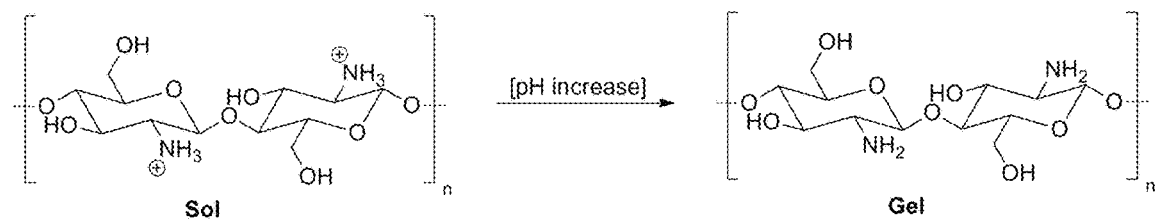
Figure 1:
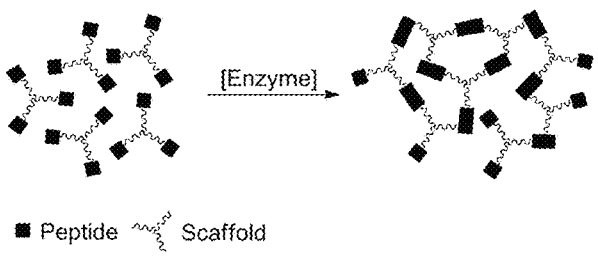
Figure 1:
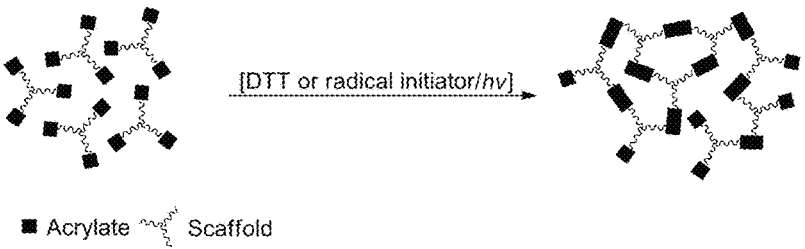
Figure 1:
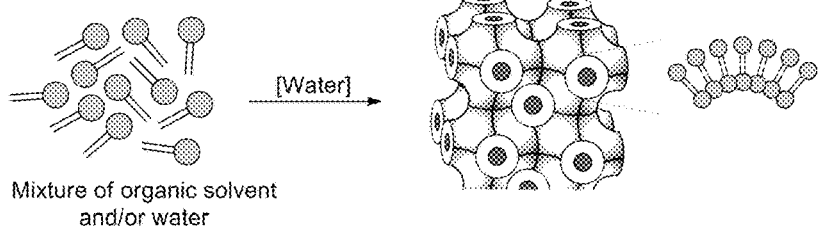

(A) Temperature change:

(B) Ion strength:

(C) pH:

(D) Enzymatic activity:

■ Peptide  ⁓⁓ Scaffold

(E) Initiator:

■ Acrylate  ⁓⁓ Scaffold

(F) Hydration:

Mixture of organic solvent
and/or water

Ion sensitive gel forming systems pH sensitive gel forming systems

Enzymatically triggered gel forming systems

SAIB dissolved in organic
solvent eg. ethanol
(low viscosity)

Neat SAIB forming an
amorphous carbohydrate glass matrix
(very high vicosity)

GEL FORMULATIONS FOR GUIDING RADIOTHERAPY

RELATED APPLICATIONS

This application is a National Stage Filing under U.S.C. § 371 of PCT International Application PCT/EP2014/060673, filed May 23, 2014, which designates the U.S., and which claims benefit of SE Application No. 1350637-3 filed May 24, 2013, the content of each of which is incorporated by reference herein in its entirety.

FIELD OF THE INVENTION

The present invention relates to improved formulations for guiding radiotherapy.

TECHNICAL BACKGROUND

Every year more than 12 million people are diagnosed with cancer worldwide and over 7.5 million people die from cancer each year. These numbers are expected to increase because of population growth and due to the lifestyle in the Western world. Radiotherapy is an important part of modern cancer treatment and more than 50% of cancer patients receive radiotherapy at least once. Modern radiotherapy relies on advanced high precision planning, treatment equipment and imaging techniques (such as, e.g., computed tomography (CT), positron-emission tomography (PET) and magnetic imaging resonance (MRI)) in order to deliver high radiation doses to a precisely defined target in patients.

One of the main difficulties in external beam radiotherapy is that both tumors and the surrounding tissue move significantly and unpredictably during radiotherapy; both within each single treatment, and during the whole course of radiotherapy, lasting usually 5-7 weeks. These movements can be dramatic (e.g. several cm within seconds) and may be caused by various factors such as respiration, bladder- and bowel filling, air passing colon, tumor shrinkage and set-up variation of the patient. One way of minimizing this problem is the implantation of markers in or adjacent to the tumor allowing frequent imaging and treatment adaptation. So far, markers have been inserted using long and thick needles, a complicated procedure with a significant risk of complications, which is limiting the practical usefulness of markers in radiotherapy.

Ideally, a tissue marker should enable tracking of tumor movement; be visible on several image modalities; be visible for an extended period (e.g., at least 4 weeks); be non-toxic; and be easy to insert.

Various attempts have been made for improvements within the field of radiotherapy. EP1006935 describes a composition for controlled release of a substance WO9403155 describes a hydrogel composition prepared from a backbone bonded to a cross-linking agent. The hydrogels may be loaded with therapeutic drugs and diagnostic labels, including X-ray contrast imaging agents for disease diagnostics and treatment. US20120065614 discloses a hybrid system for bio imaging. Gold is bound into a matrix comprising a hydrogel or polymer or similar. In US20100297007 a substantially bi concave shaped nanoparticle is disclosed, the nanoparticle comprising an aqueous inner core and a hydrophilic outer shell comprising an amphiphilic polymer.

Furthermore, US2009110644 discloses a nanoparticle consisting of a polymer which is a metal chelating agent coated with a magnetic metal oxide, wherein at least one active agent is covalently bound to the polymer. In the documents US20100290995 and US2005036946, radio-opaque biodegradable compositions are disclosed by modifying terminal groups of synthetic and natural biodegradable polymers such as polylactones with iodinated moieties and in SE403255 a contrast agent is disclosed that comprises a polymer comprising hydroxy- and/or carboxy- and/or amino groups further comprising X-ray contrast giving iodo-substituted aromatic groups. Further yet, the document WO9519184 discloses air encapsulating micro particles formed by ionotropically gelling synthetic polyelectrolytes such as poly(carboxylato-phenoxy)phosphazene, poly(acrylic acid), poly(methacrylic acid) and methacrylic acid copolymers (Eudragit's) by contact with multivalent ions such as calcium ions.

There are several drawbacks to the current clinical practice using solid markers and the methods described in the documents above. Installation of solid markers is invasive due to the large dimension of the solid implant which may cause severe complications limiting is usefulness in radiotherapy. By combining gel-forming, low-viscosity solutions with solid particles and/or organic X-ray contrast agents (or other imaging modalities) injectable gels can be formulated with fine-tuned properties as these can be modified by multiply parameters with respect to the gel forming solution and the contrast agents used. The solid particles can, besides contributing to the overall contrast of the system, also carry pharmaceutical substances and control their release in a controlled manner.

One aim of the present invention is to provide new formulations comprising gel-forming, low-viscosity systems that are easy to administer parenterally, and wherein the present invention provides good visualization by one or multiple imaging modalities, including X-ray imaging.

SUMMARY OF THE INVENTION

X-ray imaging of a locally administered reference marker is achieved by use of an X-ray contrast composition, wherein the X-ray contrast composition exhibits contrast properties and wherein at least 60% of an administrated amount of said X-ray contrast composition remains more than 24 hours within 10 cm from an injection point when the X-ray contrast composition is administrated to a human or animal body.

DETAILED DESCRIPTION OF THE INVENTION

The formulation is preferably in the form adapted for parenteral administration, and should preferably consist of pharmaceutically acceptable constituents. The formulation which as such has a comparable low viscosity is intended for injection in the body of a human or animal, where after the formulation becomes more viscous, e.g. it goes through a sol-gel transition (liquid to gel) or forms a amorphous glass matrix, due to the presence of the gel-forming system. It is preferred that the viscosity of the formulation after injection in the body of a human or animal increases by at least 50%, such as at least 80%, such as at least 100%, or at least 150%, or at least 200%, or at least 300%, or at least 500%, or at least 750%, or at least 1000%, or at least 10,000%, or that the formulation becomes essentially solid (non-viscous).

The formulation is preferably adapted for injection via a thin needle used for injection into a body or surgical related procedures, such as but not limited to biopsy. The viscosity of the hydrogel or gel-forming formulation before injection can be any suitable viscosity such that the formulation can be parenterally administered to a patient.

Exemplary formulations include, but are not limited to, those having a viscosity (prior to administration/injection) lower than 10,000 centipoise (cP), e.g. lower than 2,000 cP, such as 10 to 2,000 cP, such as 20 to 1,000 cP, such as 150 to 350 cP, such as 400 to 600 cP, such as 600 to 1,200 cP or such as 1,000 to 2,000 cP, or 10 to 600 cP, or 20 to 350 cP, at 20° C.

Alternative formulations include, but are not limited to, those having a viscosity (prior to administration/injection) lower than 10,000 centipoise (cP), e.g. lower than 2,000 cP, such as 10 to 2,000 cP, such as 20 to 1,000 cP, such as 150 to 350 cP, such as 400 to 600 cP, such as 600 to 1,200 cP or such as 1,000 to 2,000 cP, or 10 to 600 cP, or 20 to 350 cP, at 5° C.

When referred to herein, the (dynamic) viscosity is measured at the specified temperature in accordance with the method described in ASTM D7483.

Hydrogels, gels or amorphous glass matrixes may be formed either through covalent bond formation or ionic- or hydrophobic interactions. Physical (non-covalent) cross-links may result from complexation, hydration, hydrogen bonding, desolvation, Van der Waals interactions, ionic bonding, combinations thereof, and the like, and may be initiated by mixing two precursors that are physically separated until combined in situ, or as a consequence of a prevalent condition in the physiological environment, including temperature, pH, ionic strength, combinations thereof, and the like. Chemical (covalent) cross linking may be accomplished by any of a number of mechanisms, including free radical polymerization, condensation polymerization, anionic or cationic polymerization, step growth polymerization, electrophile-nucleophile reactions, combinations thereof, and the like. FIGS. 1-6 illustrate exemplary hydrogel and/or gel-forming and/or amorphous glass matrix systems that can be used in the present invention.

The hydrogel, gel or amorphous glass matrix forming compositions may be loaded with organic x-ray agents such as iodinated polymers or sugars and nanoparticles or sub-micron particles either prior to or during gel formation, such as when the formulation is in a sol-state or in transition to the gel-state, e.g., by diffusion into the hydrogel composition. These x-ray agents or particles may either be entrapped in the gel matrix without any chemical cross-linking, or they may be bonded, non-covalently or covalently, to the backbone or cross-linking agent of the hydrogel, gel or amorphous glass matrix. The organic x-ray agents may be one component in the gel and the particles another component, where the particles are either a contrast agent for imaging by x-ray, MRI, PET, SPECT, fluorescence or ultrasound, and/or contain pharmaceutical agents. Pharmaceutical agents may be, but not limited to, radiosensitzers, chemotherapeutics or hormones. MRI agents such as gadolinium may be a component in the gel forming systems. Pharmaceutical agents can furthermore be covalent or non-covalently embedded in the hydrogel, gel or amorphous glass matrix.

After injection, the formulation typically provides a well defined assembly of x-ray contrast agents which provides contrast in e.g. X-ray imaging, and which may serve as a marker, thus, enabling tracking of tumor movement during e.g. radiotherapy or surgical procedures.

US2001/0142936 discloses covalently linked hydrogels particles in the micrometer range (10 μm-500 μm) with/without radiopaque agents for use of conformal filling of surgical sites with optional imaging in order to ensure that the implants are positioned correctly. The present invention offers several advantageous features as it exploits organic x-ray contrast agents that may be in combination with nano-sized particles combined with a gel forming injectable liquid. Nano-sized particles exhibit low/no sedimentation rate due to the effects of Brownian motion which is problematic for micrometer sized particles. Furthermore, dividing the particles and the gel forming solution into two components enables control over particle diffusion, release etc. within the gel which is advantageous for controlling the overall properties of the formulation. US2011/0142936 is built on the invention that swelling of the gel will increase the distance between normal and tumor tissue by injecting into iatrogenic ("medically produced") spaced. The present invention aims at infiltrate tissue with minimal impact on the shape and position of the target tissue typically being a cancer. Furthermore, the intention of the present invention is to infiltrate tissue with minimal change in size and location why swelling is for this invention a disadvantage. This in contrast to US2001/0142936

In the context of the present invention, a "marker" or "tissue marker" is a detectable agent or composition which does not move, or stays substantially in the same position, for several days or weeks once it has been administered or implanted into a specific site or tissue of a mammalian body. A tissue marker can, for example, comprise one or more X-ray contrast agents, radioactive compounds, paramagnetic compounds, fluorescent agents, or other detectable agents.

In the context of the present invention, a "gel" is defined as a carrier matrix in which the detectable agent (contrast agent) is dispersed and/or dissolved within. The term "gel" includes systems such as hydrogels, gels or amorphous glass matrices which upon injection into a human or an animal increases viscosity due to chemical and/or physical stimulus.

An "imageable tissue marker" or "imageable marker" comprises a detectable agent in a form and/or a sufficient amount to allow for detection of the tissue marker by an external imaging modality if administered or implanted into a mammalian body. Exemplary external imaging modalities include, but are not limited to, X-ray imaging, CT imaging, MRI, PET imaging, single photon emission computed tomography (SPECT) imaging, nuclear scintigraphy imaging, ultrasonography imaging, ultrasonic imaging, near-infrared imaging and/or fluorescence imaging. Some examples of the brand names and types of different image techniques are e.g. ExacTrac® (BrainLAB), Cone Beam (e.g. Vairan) and OBI (e.g. On-Board Imager® Varian).

Contrast Agents

Contrast may be achieved using organic x-ray contrast agents, such as radiopague agents such as iodinated compounds, which may be combined with chelators of MRI agents such as gadolinium, and/or combined with chelators of PET imaging agents such as copper-64, which may further be combined with solid inorganic particles. Chelators may be DOTA, EDTA, or DTPA and chelators will be non-covalently embedded or covalently conjugated to the gel-forming components. The combined contrast agents should preferably be visible by at least CT imaging. Preferred contrast agents are iodinated compounds such as polymers or sugar molecules such as derivatives of glucose or sucrose or other oligosaccharides. Solid particles may comprise, or consist of, one or more X-ray contrast agents, i.e., compounds that are able to block or attenuate X-ray radiation. Such compounds include transition metals, rare earth metals, alkali metals, alkali earth metals, other metals, as defined by the periodic table. A metal or alkali metal may appear in non-oxidized or any of the existing oxidation states for the metal. These oxidation states include monovalent cations, divalent cations, trivalent cations, tetravalent cations, pentavalent cations, hexavalent cations and heptavalent cations.

In one embodiment, the one or more X-ray contrast agents are selected from Iodine (I), gold (Au), bismuth (Bi), gadolinium (Gd), iron (Fe), barium (Ba), calcium (Ca) and magnesium (Mg). In a particular embodiment, the detectable compound comprises one or more compounds selected from the group of gold (Au) and bismuth (Bi). The one or more X-ray contrast agents are typically present in metal form, in alloy form, in oxide form or in salt form.

It should be understood that besides iodinated compounds which provides a useful contrast for X-ray imaging, the formulation may also include solid particles that are visible by X-ray imaging or other imaging modalities than X-ray imaging. In one embodiment, the solid-particles are furthermore visible by MR and/or PET imaging, or by other imaging modalities.

In a particular embodiment, the gel-forming composition may further comprise a radioactive or paramagnetic compound for one or more imaging modalities such as MRI, PET imaging, SPECT imaging, nuclear scintigraphy imaging, ultrasonography imaging, ultrasonic imaging, near-infrared imaging and/or fluorescence imaging.

In some interesting embodiments, the formulation according to any one of the preceding claims, contain solid particles that comprise one or more radioactive, paramagnetic or ferromagnetic particles.

Moreover, individual particles may comprise two or more types of compounds which are visible in different imaging modalities.

Said radioactive compounds may comprise isotopes of Copper ($^{61}$Cu, $^{64}$Cu, and $^{67}$Cu), Indium ($^{111}$In) Technetium ($^{99m}$Tc), Rhenium ($^{186}$Re, $^{188}$Re), Gallium ($^{67}$Ga, $^{68}$Ga), Strontium ($^{89}$Sr), Samarium ($^{153}$Sm), Ytterbium ($^{169}$Yb) Thallium ($^{201}$Tl), Astatine ($^{211}$At), Lutetium ($^{177}$Lu), Actinium ($^{225}$Ac), Yttrium ($^{90}$Y), Antimony ($^{119}$Sb), Tin ($^{117}$Sn, $^{113}$Sn), Dysprosium ($^{159}$Dy), Cobalt ($^{56}$Co), Iron ($^{59}$Fe), Ruthenium ($^{97}$Ru, $^{103}$Ru), Palladium ($^{103}$Pd), Cadmium ($^{115}$Cd), Tellurium ($^{118}$Te, $^{123}$Te), Barium ($^{131}$Ba, $^{140}$Ba), Gadolinium ($^{149}$Gd, $^{151}$Gd), Terbium ($^{160}$Tb), Gold ($^{198}$Au, $^{199}$Au), Lanthanum ($^{140}$La), Zirconium ($^{89}$Zr) and Radium ($^{223}$Ra, $^{224}$Ra), wherein said isotope of a metal radionuclide may appear in any of the existing oxidation states for the metal. These oxidation states include monovalent cations, divalent cations, trivalent cations, tetravalent cations, pentavalent cations, hexavalent cations and heptavalent cations.

Said paramagnetic or ferromagnetic compounds may also be selected from the group of Scandium (Sc), Yttrium (Y), Lanthanum (La), Titanium (Ti), Zirconium (Zr), Hafnium (Hf), Vandium (V), Niobium (Nb), Tantalum (Ta); Chromium (Cr), Molybdenium (Mo), Tungsten (W), Manganese (Mn), Technetium (Tc), Rhenium (Re), Iron (Fe), Ruthenium (Ru), Osmium (Os), Cobalt (Co), Rhodium (Rh), Iridium (Ir), Nickel (Ni), Palladium (Pd), Platinum (Pt), Copper (Cu), Silver (Ag), Gold (Au), Zinc (Zn), Cadmium (Cd), Mercury (Hg), the lanthanides such as Lathanum (La), Cerium (Ce), Praseodymium (Pr), Neodymium (Nd), Promethium (Pm), Samarium (Sm), Europium (Eu), Gadolinium (Gd), Terbium (Tb), Dysprosium (Dy), Holmium (Ho), Erbium (Er), Thulium (Tm), Ytterbium (Yb), Lutetium (Lu)) and the actinides such as Actinium (Ac), Thorium (Th), Protactinium (Pa), Uranium (U), Neptunium (Np), Plutonium (Pu), Americium (Am), Curium (Cm), Berkelium (Bk), Californium (Cf), Einsteinium (Es), Fermium (Fm), Mendelevium (Md), Nobelium (No) and Lawrencium (Lr), wherein said paramagnetic or ferromagnetic compounds may appear in any of the existing oxidation states for the metal. These oxidation states include monovalent cations, divalent cations, trivalent cations, tetravalent cations, pentavalent cations, hexavalent cations and heptavalent cations.

Said one or more radioactive, paramagnetic or ferromagnetic compounds may be covalently linked to gel-forming components or the nano-sized particles or non-covalently associated with the gel-forming components or nano-sized particles.

In one embodiment, the gel-forming components or nano-sized particles further comprise one or more fluorophore compounds for near infrared fluorescence imaging. Said compounds may comprise a fluorescent proteins, peptides, or fluorescent dye molecules. Common classes of fluorescent dyes include xanthenes such as rhodamines, rhodols and fluoresceins, and their derivatives; bimanes; coumarins and their derivatives such as umbelliferone and aminomethyl coumarins; aromatic amines such as dansyl; squarate dyes; benzofurans; fluorescent cyanines; carbazoles; dicyanomethylene pyranes, polymethine, oxabenzanthrane, xanthene, pyrylium, carbostyl, perylene, acridone, quinacridone, rubrene, anthracene, coronene, phenanthrecene, pyrene, butadiene, stilbene, lanthanide metal chelate complexes, rare-earth metal chelate complexes, and derivatives of such dyes. Typical fluorescein dyes include 5-carboxyfluorescein, fluorescein-5-isothiocyanate and 6-carboxyfluorescein; examples of other fluorescein dyes can be found, for example, in U.S. Pat. Nos. 6,008,379, 5,750,409, 5,066,580, and 4,439,356. The species may also include a rhodamine dye, such as, for example, tetramethylrhodamine-6-isothiocyanate, 5-carboxytetramethylrhodamine, 5-carboxy rhodol derivatives, tetramethyl and tetraethyl rhodamine, diphenyldimethyl and diphenyldiethyl rhodamine, dinaphthyl rhodamine, rhodamine 101 sulfonyl chloride (sold under the tradename of TEXAS RED), and other rhodamine dyes. The species may alternatively include a cyanine dye, such as, for example, Cy3, Cy3B, Cy3.5, Cy5, Cy5.5, Cy. Or IRDye 800CW, IRDye 680LT, Qdot 800 nanocrystal, Qdot 705 nanocrystal or porphyrazine compounds In another embodiment, the nano-sized particles further comprise or consist of one or more gasses encapsulated in lipid, polymer or inorganic based particles for ultrasonography imaging. Said gasses may comprise air, sulphur halides such as sulphur hexafluoride or disulphur decafluoride; fluorocarbons such as perfluorocarbons; fluorinated (e.g. perfluorinated) ketones such as perfluoroacetone; and fluorinated (e.g. perfluorinated) ethers such as perfluorodiethyl ether. Representative perfluorocarbons, which may for example contain up to 7 carbon atoms, include perfluoroalkanes such as perfluoromethane, perfluoroethane, perfluoropropanes, perfluorobutanes (e.g. perfluoro-n-butane, optionally in a mixture with other isomers such as perfluoro-iso-butane), perfluoropentanes, perfluorohexanes and perfluoroheptanes; perfluoroalkenes such as perfluoropropene, perfluorobutenes (e.g. perfluorobut-2-ene) and perfluorobutadiene; perfluoroalkynes such as perfluorobut-2-yne; perfluorocycloalkanes such as perfluorocyclobutane, perfluoromethylcyclobutane, perfluorodimethylcyclobutanes, perfluorotrimethylcyclobutanes, perfluorocyclopentane, perfluoromethylcyclopentane, perfluorodimethylcyclopentanes, perfluorocyclohexane, perfluoromethylcyclohexane and perfluorocycloheptane; and mixtures of any of the foregoing, including mixtures with gases such as nitrogen, carbon dioxide, oxygen etc, but not limited to those.

Figure 7:
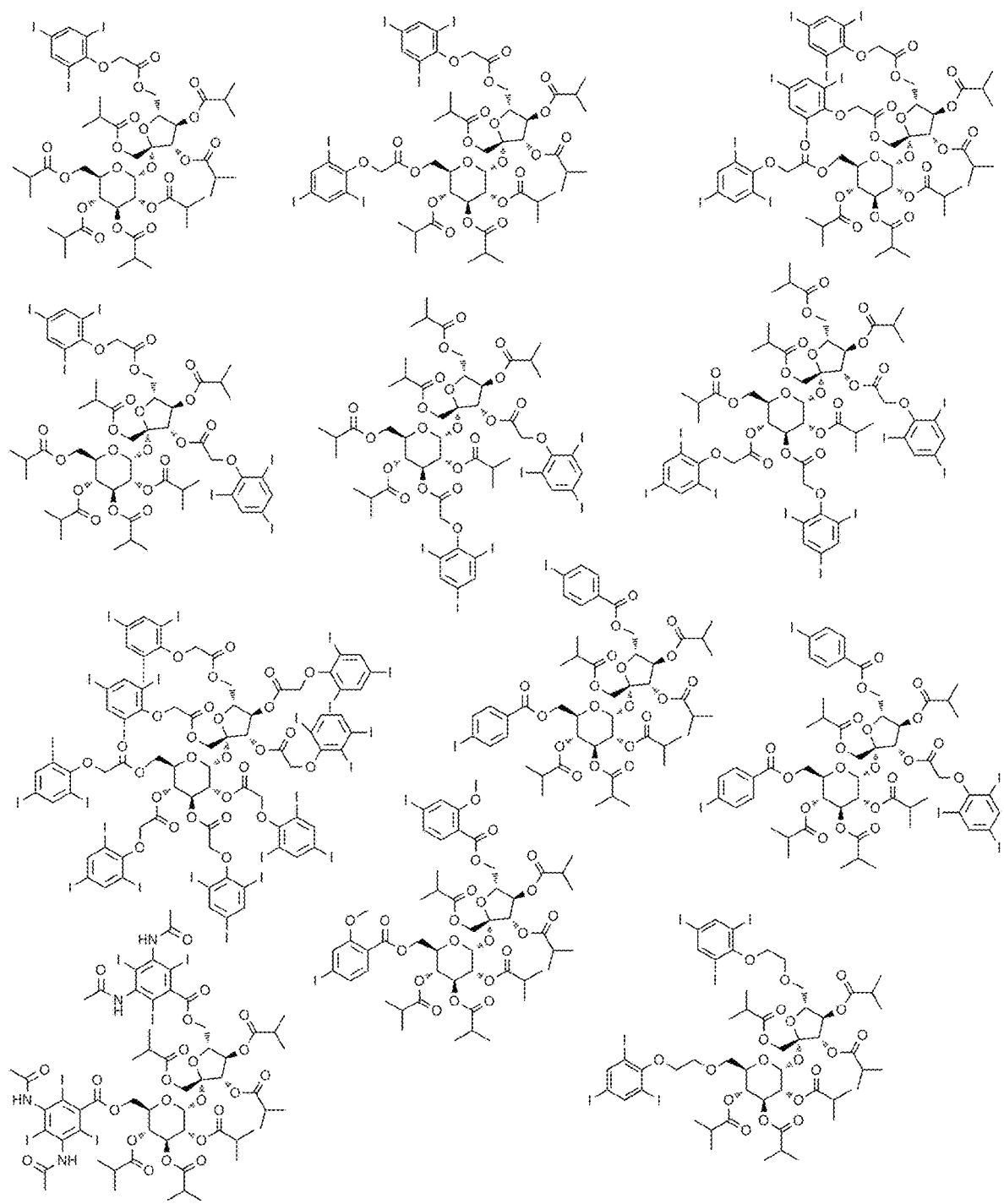

In another embodiment, contrast in achieved using small organic iodine containing compounds. Said small organic iodine containing compounds includes commercial available iodinated contrast agents such as diatrizoate (marketed e.g. under the trade name Gastrografen™), ionic dimers such as ioxaglate (marketed e.g. under the trade name Hexabrix™), nonionic monomers such as iohexol (marketed e.g. under the trade name Omnipaque™), iopamidol (marketed e.g. under the trade name Isovue™), iomeprol (marketed e.g. under the trade name Iomeron™) and the non-ionic dimer iodixanol (marketed under the trade name and Visipaque™) Additional examples of small organic iodine containing compounds includes the ones disclosed in WO2009/071605, EP1186305, EP686046, EP108638, EP0049745, EP0023992, WO2003080554, WO2000026179, WO1997000240, WO9208691, U.S. Pat. Nos. 3,804,892, 4,239,747, 3,763,226, 3,763,227 and 3,678,152, but not limited to those. In another interesting embodiment, the said small organic iodine containing compounds includes iodinated derivates of sucrose acetate isobutyrate (SAIB). In contrast to what is disclosed in for example EP1006935, where a composition for controlled release of a substance is disclosed which composition comprises SAIB, this specific embodiment according to the present invention aims at providing a stable contrast agent embedded in SAIB-gel. Examples of such iodinated derivates of sucrose acetate isobutyrate (SAIB) are illustrated in FIG. 7, but not limited to those. Such compounds may be used alone or in combination with solid particles to achieve an injectable gel visible by at least CT imaging. In one specific embodiment of the invention the hydration sensitive gel forming component is sucrose acetate isobutyrate (SAIB) a hydrophobic component composed of sucrose (the scaffold) which has been acylated with isobutyrate and acetate. Preferred scaffolds of this invention are monosaccharides, disaccharides or trisaccharides. A particularly preferred dissacharide scaffold is sucrose, however, the alcohol containing scaffold may be derived from a polyhydroxy alcohol having from about 2 to about 20 hydroxy groups and may be formed by esterifying 1 to 20 polyol molecules. Suitable alcohol moieties include those derived by removing one or more hydrogen atoms from: monofunctional C1-C20 alcohols, difunctional C1-C20 alcohols, trifunctional alcohols, hydroxy-containing carboxylic acids, hydroxy-containing amino acids, phosphate-containing alcohols, tetrafunctional alcohols, sugar alcohols, monosaccharides, and disaccharides, sugar acids, and polyether polyols. More specifically, alcohol moieties may include one or more of: dodecanol, hexanediol, more particularly, 1,6-hexanediol, glycerol, glycolic acid, lactic acid, hydroxybutyric acid, hydroxyvaleric acid, hydroxycaproic acid, serine, ATP, pentaerythritol, mannitol, sorbitol, glucose, galactose, fructose, maltose, lactose, glucuronic acid, polyglycerol ethers containing from 1 to about 10 glycerol units, polyethylene glycols containing 1 to about 20 ethylene glycol units. Additionally, any oligosaccharide containing from 3 to about 6 monosaccharides may be used as the scaffold in the present invention. In general, the scaffold esters of the invention can be made by reacting one or more alcohols, in particular one or more polyols, which will form the alcohol moiety of the resulting esters with one or more carboxylic acids, lactones, lactams, carbonates, or anhydrides of the carboxylic acids which will form the acid moieties of the resulting esters. The esterification reaction can be conducted simply by heating, although in some instances addition of a strong acid or strong base esterification catalyst may be used. Alternatively, an esterification catalyst such as stannous 2-ethylhexanoate or activation reagents such as N-(3-Dimethylaminopropyl)-N'-ethylcarbodiimide (EDC), N,N'-Dicyclohexylcarbodiimide (DCC), O-(7-azabenzotriazol-1-yl)-N,N,N',N'-tetramethyluronium hexafluorophosphate (HATU) and the like can be used.

The acyl groups forming the acyloxy substituents of the invention may be any moiety derived from a carboxylic acid. More particularly, the acyl groups of the compositions of the invention may be of the RCO—, where R is optionally oxy-substituted alkyl of 2-10 carbon atoms which may be linear or branched hydrocarbons with one or more functional groups present in the chain. Using carboxylic acids and/or polyols of different chain length and using carboxylic acids having oxy-substitution allows control of the degree of hydrophilicity and of the solubility of the resulting ester. Such materials are sufficiently resistant to dissolution in vivo that they are able to form stabile hydrophobic gels which may encapsulate the said contrast agents of the present invention. The gels may further comprise a pharmaceutical agent in combination with the contrast agent.

Coating of Solid Particles

The solid particles may further comprise a variety of other components. Useful solid particles include uncoated or coated metal particles, uncoated or coated solid metal salts, as well as liposomes, polymersomes, dendrimers, water-soluble cross-linked polymers, and micelles comprising such solid particles. As used herein, a solid particle which is "coated" comprises a shell or surface coating around a solid core material. The shell or surface coating can be attached to the core material covalently, non-covalently, or by a mixture of covalent and non-covalent bonds. Exemplary shell or surface coatings are described herein. In one embodiment, the solid particle comprises a polymer surface coating non-covalently or covalently attached to the particle core surface. The polymer may be a homopolymer, a copolymer, block copolymer, or a graft copolymer, or a dendrimer-type copolymer of synthetic or natural origin, but not limited to those. Typically, the polymer coating comprises polyethylene glycol (PEG), typically with a PEG molecular weight from 2,000 to 70,000 Daltons, such as 5,000 Daltons; dextrans, typically with a molecular weight between 2,000 and 1,000,000 Daltons; and/or hyaluronic acid, typically with a molecular weight between 2,000 and 1,000,000 Daltons. The polymers are typically combined as block copolymers in such a way that the overall polymer structure is negatively charged, allowing electrostatic interactions with a positively charged nano-sized particle surface to achieve efficient coating. In a particular embodiment, the solid particles comprise conjugated $PEG_{1000}$, $PEG_{2000}$, $PEG_{3000}$, $PEG_{5000}$ or $PEG_{10000}$, i.e., PEG preparations having an average molecular weight of approximately 1,000, 2,000, 3,000, 5,000 and 10,000 Daltons, respectively, but not limited to those. In an additional embodiment, the solid particles comprise conjugated $PNIPAM_{1000}$, $PNIPAM_{2000}$, $PNIPAM_{3000}$, $PNIPAM_{5000}$ or $PNIPAM_{10000}$, i.e., PNIPAM preparations having an average molecular weight of approximately 1,000, 2,000, 3,000, 5,000 and 10,000 Daltons, respectively, but not limited to those. In one embodiment, the solid particles comprise a shell or surface coat comprising a lipid layer such as a lipid monolayer and/or one or more lipid bilayers, and a particle core comprising an inorganic particle. Surface-coating lipids for the purpose of the present invention, and include, for example, fatty acids, neutral fats, phosphatides, glycolipids, ceramides, sphingoglipids, aliphatic alcohols, and steroids. Specific, non-limiting examples of solid particles are gold nano-sized particles synthesized with a PEG coating or PEGylated gold nanorods as described in WO 2007/129791 and Kim et al 2007 [Invest. Radiol., 2007, 42, 797-806], polymer-coated bismuth sulphide nano-sized particles as described in Rabin 2006 [Nat. Mater., 2006, 5, 188-122], calcium phosphate liposome core-shell nanocomposites, dendrimers of PAMAM with entrapped gold nano-sized particles for CT imaging as described in Haba et al. 2007 [Langmuir, 2007, 23, 5243-5246] and Kojima et al 2010 [Bioconjugate Chem., 2010, 21, 1559-1564] and other solid particles comprising X-ray contrast agents known in the art. In a specific embodiment of the present invention, the shell of the nano-sized particle comprises 1,2-distearoyl-sn-glycero-3-phosphocholine (DSPC) "A", cholesterol "B", and 1,2-distearoyl-sn-glycero-3-phosphoethanolamine-N-[methoxy (polyethylene glycol)-2000] (DSPE-PEG-2000) "C", and 1,2-distearoyl-sn-glycero-3-phosphoethanolamine-N-[methoxy (polyethylene glycol)-2000]-TATE (DSPE-PEG-2000-RGD) "D" with the molar ratio A:B:C:D, wherein A is selected from the interval 45 to 65, B is selected from the interval 35 to 45, C is selected from the interval 5 to 13, D is selected from the interval 0 to 3, and wherein A+B+C+D=100.

Coating of the solid particles can be exploited to introduce the desired chemical and/or physical properties to the colloid particles. Properties such as hydrophobicity/hydrophilicity, particle charge, hydrodynamic diameter and stability in various environments such as high/low salt concentrations, organic solvents, reductive environments and heat, among others, can be controlled by choosing the correct surface coating material. These properties, introduced to the solid particles by the surface coating, are important factors to control in order to tune the overall behavior of the X-ray contrast composition described here.

The amount of contrast agent comprised within the gel-forming composition including an embedded the nano-sized particles according to the present invention may be quantified by the weight percent of the contrast agent relative to the total weight of the gel-forming system including an embedded nano-sized particle, excluding any water comprised by the nano-sized particle, by defining the weight percent of the contrast agent relative to the weight of the shell of the nano-sized particle, or by quantifying the size of the contrasting agent within the prepared nano-sized particles. The latter can be measured by conventional methods in the art, such as cryo-transmission electron microscopy or dynamic light scattering.

Shape and Size

The nano-sized particles according to the present invention can be quasi spherical, spherical or non-spherical such as rod-shaped. Suitable nanoparticles include those having a size up to 50 µm, preferably up to 5 µm.

Preferably, the nano-sized particles according to the present invention are of a size in the range of 1 to 1000 nm, such as 2 to 10 nm, or such as 10 to 100 nm, such as 10 to 80 nm, such as 10 to 50 nm, such as 10 to 20 nm, such as 10 to 15 nm, or such as 15 to 20 nm, or such as 20 to 50 nm, or such as 50 to 80 nm, or such as 80 to 110 nm, or such as 110 to 140 nm, or such as 140 to 170 nm, or such as 170 to 200 nm or such as 200 to 220, or such as 220 to 250 nm, or such as 250 to 280 nm, or such as 280 to 310 nm, or such as 310 to 340 nm, or such as 340 to 370 nm, or such as 370 to 400 nm, or such as 400 to 420, or such as 420 to 450 nm, or such as 450 to 480 nm, or such as 480 to 500 nm, or such as 500 to 1000 nm. The size may according to the present invention be measured in terms of the diameter, length or width, including the number average diameter, length or width. In a preferred embodiment, the nano-sized particles in the composition of the present invention have a number average diameter in the range of 10 nm to 150 nm, such as 10 to 100 nm, such as 10 to 80 nm, such as 10 to 50 nm, such as 10 nm to 30 nm, such as 10 to 20 nm, or such as 30 nm to 40 nm, or such as 40 nm to 50 nm, or such as 50 nm to 60 nm, or such as 60 nm to 70 nm, or such as 70 nm to 80 nm, or such as 90 nm to 100 nm, or such as 100 nm to 110 nm, or such as 110 nm to 120 nm, or such as 120 nm to 130 nm, or such as 130 nm to 140 nm, or such as 140 nm to 150 nm. Controlling the shape and the size of the nano-sized particles may have significant influence on the stability of the nanoscale colloidal suspensions as well as the in vivo fate of the particles. In a preferred embodiment, the nano-sized particles in the composition of the present invention have a number average diameter in the range of 10 nm to 100 nm. Such nano-sized particles exhibit low/no sedimentation rate due to the effects of Brownian motion. In another preferred embodiment, the nano-sized particles in the composition of the present invention have a number average diameter <10 nm. Such particles may be cleared, after degradation of the hydrogel, by e.g. renal filtration with subsequently excretion into the urine, which may prevent prolonged tissue retention and/or thus lower the risk of toxicity.

The Organic Gel-Forming System

Suitable gel-forming components include, but are not limited to, those composed of organic constituents such as derivatized saccharides such as esterified saccharides, derivatized polyols such as esterified polyols, polymers, lipids, peptides, proteins, low molecular weight gelators and non-water soluble high-viscosity liquid carrier materials as well as combinations hereof.

The saccharides and polyols gel forming systems may be sucrose acetate isobutyrate (SAIB) a hydrophobic component composed of sucrose (the scaffold) which has been acylated with isobutyrate and acetate. Preferred scaffolds of this invention are monosaccharides, disaccharides or trisaccharides. A particularly preferred disaccharide scaffold is sucrose, however, the alcohol containing scaffold may be derived from a polyhydroxy alcohol having from about 2 to about 20 hydroxy groups and may be formed by esterifying 1 to 20 polyol molecules. Suitable alcohol moieties include those derived by removing one or more hydrogen atoms from: monofunctional C1-C20 alcohols, difunctional C1-C20 alcohols, trifunctional alcohols, hydroxy-containing carboxylic acids, hydroxy-containing amino acids, phosphate-containing alcohols, tetrafunctional alcohols, sugar alcohols, monosaccharides, and disaccharides, sugar acids, and polyether polyols. More specifically, alcohol moieties may include one or more of: dodecanol, hexanediol, more particularly, 1,6-hexanediol, glycerol, glycolic acid, lactic acid, hydroxybutyric acid, hydroxyvaleric acid, hydroxycaproic acid, serine, ATP, pentaerythritol, mannitol, sorbitol, glucose, galactose, fructose, maltose, lactose, glucuronic acid, polyglycerol ethers containing from 1 to about 10 glycerol units, polyethylene glycols containing 1 to about 20 ethylene glycol units. Additionally, any oligosaccharide containing from 3 to about 6 monosaccharides may be used as the scaffold in the present invention. In general, the scaffold esters of the invention can be made by reacting one or more alcohols, in particular one or more polyols, which will form the alcohol moiety of the resulting esters with one or more carboxylic acids, lactones, lactams, carbonates, or anhydrides of the carboxylic acids which will form the acid moieties of the resulting esters. Such systems are known to form biodegradable, amorphous carbohydrate glass matrixes upon hydration due to solvent induced phase separation.

The polymer may be a homopolymer, a copolymer, block copolymer, or a graft copolymer, or a dendrimer-type copolymer of synthetic or natural origin. Specific examples of suitable monomers may include: Lactide, glycolide, N-vinyl pyrrolidone, vinyl pyridine, acrylamide, methacrylamide, N-methyl acrylamide, hydroxyethyl methacrylate, hydroxyethyl acrylate, hydroxymethyl methacrylate, hydroxymethyl acrylate, methacrylic acid and acrylic acid having an acidic group, and salts of these acids, vinyl sulfonic acid, styrenesulfonic acid, etc., and derivatives having a basic group such as N,N-dimethylaminoethyl methacrylate, N,N-diethylaminoethyl methacrylate, N,N-dimethylaminopropyl acrylamide, salts of these derivatives, etc. Other monomers may include: acrylate derivatives and methacrylate derivatives such as ethyl acrylate, methyl methacrylate, and glycidyl methacrylate; N-substituted alkyl methacrylamide derivatives such as N-n-butyl methacrylamide; vinyl chloride, acrylonitrile, styrene, vinyl acetate, lactones such as ε-caprolactone, lactames such as ε-caprolactame and the like. Additional examples of suitable monomers include alkylene oxides such as propylene oxide, ethylene oxide and the like, but not restricted to any of these specific examples.

On the other hand, specific examples of polymeric blocks to be combined with (or bonded to) the above-mentioned monomers may include: methyl cellulose, dextran, polyethylene oxide, polypropylene oxide, polyvinyl alcohol, poly N-vinyl pyrrolidone, polyvinyl pyridine, polyacrylamide, polymethacrylamide, poly N-methyl acrylamide, polyhydroxymethyl acrylate, polyacrylic acid, polymethacrylic acid, polyvinyl sulfonic acid, polystyrene sulfonic acid, and salts of these acids; poly N,N-dimethylaminoethyl methacrylate, poly N,N-diethylaminoethyl methacrylate, poly N,N-dimethylaminopropyl acrylamide, and salts of these, poly lactic-co-glycolic acid, polycaprolactone and combinations hereof, but not limited to those. The lipid may be any phospholipid including one or more of a sterol such as cholesterol, and cholestanol, a fatty acid having a saturated or unsaturated acyl group having 8 to 22 carbon atoms and an antioxidant such as alpha-tocopherol. Examples of the phospholipids include, for example, phosphatidylethanolamines, phosphatidylcholines, phosphatidylserines, phosphatidylinositols, phosphatidyl-glycerols, cardiolipins, sphingomyelins, ceramide phosphorylethanolamines, ceramide phosphorylglycerols, ceramide phosphorylglycerol phosphates, 1,2-dimyristoyl-1,2-deoxyphosphatidylcholines, plasmalogens, phosphatidic acids, and the like, and these may be used alone or two or more kind of them can be used in combination. The fatty acid residues of these phospholipids are not particularly limited, and examples thereof include a saturated or unsaturated fatty acid residue having 12 to 20 carbon atoms. Specific examples include an acyl group derived from a fatty acid such as lauric acid, myristic acid, palmitic acid, stearic acid, oleic acid and linoleic acid. Further, phospholipids derived from natural products such as egg yolk lecithin and soybean lecithin can also be used. Also suitable are, for example, di- and tri-glycerides, 1,2-bis (oleoyloxy)-3-(trimethylammonio)propane (DOTAP), 1-N, N-dimethylaminodioleoylpropane (DODAP), 1-oleoyl-2-hydroxy-3-N,N-dimethylaminopropane, 1,2-diacyl-3-N,N-dimethylaminopropane, 1,2-didecanoyl-1-N,N-dimethylaminopropane, 3-beta-[n-[(N',N'-dimethylamino) ethane]-carbamoyl]-cholesterol (DC-Chol), 1,2-dimyristyloxypropyl-3-dimethylhydroxyethylammonium bromide (DMRIE), 1,2-dioleoyloxypropyl-3-dimethylhydroxyethylammonium bromide (DORI), and the like, but not limited to those.

A "peptide" or "polypeptide" refers to a string of at least two α-amino acid residues linked together by chemical bonds (for example, amide bonds). Depending on the context, the term "peptide" may refer to an individual peptide or to a collection of peptides having the same or different sequences, any of which may contain only naturally occurring α-amino acid residues, non-naturally occurring α-amino acid residues, or both. The peptide may exhibit self-assembling properties, for example, peptide amphiphiles, and peptides with β-sheet or α-helical forming sequences. The peptides may include D-amino acids, L-amino acids, or combinations thereof. Suitable, naturally-occurring hydrophobic amino acid residues which may be in the self-assembling peptides include Ala, Val, Ile, Met, Phe, Tyr, Trp, Ser, Thr and Gly. The hydrophilic amino acid residues may be basic amino acids (for example, Lys, Arg, His, Orm); acidic amino acids (for example, Glu, Asp); or amino acids that form hydrogen bonds (for example, Asn, Gln). Degradation of L-amino acids produces amino acids that may be reused by the host tissue. L-configured amino acid residues occur naturally within the body, distinguishing peptides formed from this class of compounds from numerous other biocompatible substances. L-configured amino acids contain biologically active sequences such as RGD adhesion sequences. The amino acid residues in the self-assembling peptides may be naturally occurring or non-naturally occurring amino acid residues. Naturally occurring amino acids may include amino acid residues encoded by the standard genetic code, amino acids that may be formed by modifications of standard amino acids (for example pyrrolysine or selenocysteine), as well as non-standard amino acids (for example, amino acids having the D-configuration instead of the L-configuration). Although, non-naturally occurring amino acids have not been found in nature, they may be incorporated into a peptide chain. These include, for example, D-alloiso-leucine(2R,3S)-2-amino-3-methylpentanoic: acid, L-cyclopentyl glycine (S)-2-amino-2-cyclopentyl acetic acid. Self-assembling peptides used in accordance with the disclosure may vary in length so long as they retain the ability to e.g. self-assemble to an extent useful for one or more of the purposes described herein. Peptides having as few as two α-amino acid residues or as many as approximately 50 residues may be suitable. In embodiments, α-amino acid analogs can be used. In particular, α-amino acid residues of the D-form may be used. Useful peptides may also be branched. One or more of the amino acid residues in a self-assembling peptide may be functionalized by the addition of a chemical entity such as an acyl group, a carbohydrate group, a phosphate group, a farnesyl group, an isofarnesyl group, a fatty acid group, or a linker for conjugation. This functional group may provide for inter-peptide linkages, or linkages between the peptide and the hydrogel or hydrogel precursor. For example, the hydrophobic portion of an amphiphilic peptide may be functionalized with acetylene groups. Alternatively, either or both ends of a given peptide may be modified. For example, the carboxyl and/or amino groups of the carboxyl- and amino-terminal residues, respectively, may be protected or not protected. Examples of self assembling peptides include the ones disclosed by Nagai, et al. [J. Controlled Release, 2006, 115, 18-25], Schneider et al. [PLoS ONE, 2008, 1, 1-8] and Hartgerink et al. [PNAS, 2002, 99, 5133-5138].

The protein is not particularly limited and may have a molecular weight from 5-500 kDa, such as 20-200 kDa. It may be of natural origin or human engineered protein expressed in accessible biological expression systems such as e.g. yeast, mammalian, and bacterial expression systems. Preferably, is has a responsive domain such as α-helical coiled-coil or leucine zipper domain—but not limited to those, which upon external or internal stimuli results in hydrogel formation which structurally respond to changes in e.g. pH, temperature, and ionic strength. Examples of such proteins include the ones disclosed by Banta et al. [Annu. Rev. Biomed. Eng., 2010, 12, 167-86].

The low molecular weight gelators include any molecule with molecular weight from 100-4,000 Daltons, such as 250-1,000 Daltons with an amphiphilic structure capable of forming a hydrogel. Specific, non-limiting examples of low molecular weight gelators as described in WO 2008/102127 A2, Chem. Rev., 2004, 104, 1201-1217 and Eur. J. Org. Chem., 2005, 3615-3631.

The non-water soluble high-viscosity liquid carrier materials include, but are not limited to, sucrose acetate isobutyrate, stearate esters such as those of propylene glycol, glyceryl, diethylaminoethyl, and glycol, stearate amides and other long-chain fatty acid amides, such as N,N'-ethylene distearamide, stearamide MEA and DEA, ethylene bistearamide, cocoamine oxide, long-chain fatty alcohols, such as cetyl alcohol and stearyl alcohol, long-chain esters such as myristyl myristate, behenyerucate, glyceryl phosphates, acetylated sucrose distearate (Crodesta A-IO), and the like.

The gel of the present invention having biodegradability and sol-gel phase transition which depends on pH, temperature, ion-concentration, enzymatic activity, electric field or hydration.

The composition of the solvent (dispersion medium) should not be particularly limited, and examples include, for example, a buffer such as phosphate buffer, citrate buffer, and phosphate-buffered physiological saline, physiological saline, a medium for cell culture and biocompatible organic solvent such as ethanol, ethyl lactate, propylene carbonate, glycofurol, N-methylpyrrolidone, 2-pyrrolidone, propylene glycol, acetone, methyl acetate, ethyl acetate, methyl ethyl ketone, benzyl alcohol, triacetin, dimethylformamide, dimethylsulfoxide, tetrahydrofuran, caprolactam, decylmethylsulfoxide, oleic acid, 1-dodecylazacycloheptan-2-one and the like. Although the formulation can be stably dispersed in these solvents (dispersion media), the solvents may be further added with a saccharide (aqueous solution), for example, a monosaccharide such as glucose, galactose, mannose, fructose, inositol, ribose and xylose, disaccharide such as lactose, sucrose, cellobiose, trehalose and maltose, trisaccharide such as raffinose and melezitose, and polysaccharide such as $\alpha$-, $\beta$-, or $\gamma$-cyclodextrin, sugar alcohol such as erythritol, xylitol, sorbitol, mannitol, and maltitol, or a polyhydric alcohol (aqueous solution) such as glycerin, diglycerin, polyglycerin, propylene glycol, polypropylene glycol, ethylene glycol, diethylene glycol, triethylene glycol, polyethylene glycol, ethylene glycol mono-alkyl ether, diethylene glycol mono-alkyl ether and 1,3-butylene glycol. Additives may furthermore be selected from the group consisting of bioavailable materials such as amiloride, procainamide, acetyl-beta-methylcholine, spermine, spermidine, lysozyme, fibroin, albumin, collagen, transforming growth factor-beta (TGF-beta), bone morphogenetic proteins (BMPs), fibroblast growth factor (bFGF), dexamethason, vascular endothelial growth factor (VEGF), fibronectin, fibrinogen, thrombin, proteins, dexrazoxane, leucovorin, ricinoleic acid, phospholipid, small intestinal submucosa, vitamin E, polyglycerol ester of fatty acid, Labrafil, Labrafil M1944CS, citric acid, glutamic acid, hydroxypropyl, isopropyl myristate, Eudragit, tego betain, dimyristoylphosphatidyl-choline, scleroglucan, and the like; organic solvents such as cremophor EL, ethanol, dimethyl sulfoxide, and the like; preservatives such as methylparaben and the like; sugars such as starch and derivatives thereof, sugar-containing polyols such as sucrose-mannitol, glucose-mannitol, and the like; amino acids such as alanine, arginine, glycine, and the like; polymer-containing polyols such as trehalose-PEG; sucrose-PEG, sucrose-dextran, and the like; sugar-containing amino acid such as sorbitol-glycine, sucrose-glycine, and the like; surfactants such as poloxamer of various molecular weights, Tween 20 Tween 80, Triton X-100, sodium dodecyl sulfate (SDS), Brij, and the like; sugar-containing ions such as trehalose-$ZnSO_4$, maltose-$ZnSO_4$, and the like; and bio-acceptable salts such as silicate, NaCl, KCl, NaBr, NaI, LiCl, n-$Bu_4$NBr, n-$Pr_4$NBr, $Et_4$NBr, $Mg(OH)_2$, $Ca(OH)_2$, $ZnCO_3$, $Ca_3(PO_4)_2$, $ZnCl_2$, $(C_2H_3O_2)_2$Zn, $ZnCO_3$, $CdCl_2$, $HgCl_2$, $CaCl_2$, $(CaNO_3)_2$, $BaCl_2$, $MgCl_2$, $PbCl_2$, $AlCl_2$, $FeCl_2$, $FeCl_3$, $NiCl_2$, AgCl, AuCl, $CuCl_2$, sodium tetradecyl sulfate, dodecyltrimethyl-ammonium bromide, dodecyltrimethylammonium chloride, tetradecyltrimethyl-ammonium bromide, and the like, but not limited to those.

In one embodiment of the present invention, the content of the additive is from $1 \times 10^{-6}$–30 wt %, preferably $1 \times 10^{-3}$ to 10 wt %, based on the total weight of the gel forming component(s).

A preferred injectable medical gel-forming system can have one or more, preferably all, of the following features:

(1) In order to be injectable, the system should be in a sol state before administration. The sol state should be of sufficiently low viscosity—typically lower than 10,000 cP, preferably lower than 2,000 cP, at 20° C. (or alternatively lower than lower than 10,000 cP, preferably 2,000 cP, at 5° C.)—to allow for small needle head to alleviate the patient discomfort and simplify insertion procedure.

(2) Gelation via either chemical cross-linking, physical association or hydration starts to happen or is complete after injection.

(3) The gels should be biodegradable or gradually dissolvable within a controlled time period, and the products should be cleared/secreted through normal pathways.

(4) The polymer itself and the degradable products should be biocompatible. Likewise, if additives are added, such as cross-linking agents, initiators etc. these should also be biocompatible.

(5) The gel could potentially have cell/tissue-adhesive properties.

(6) The gel should not result in adverse effects such as immune response, e.g. inflammation.

It should be understood, that the gel-forming system should preferably be biocompatible, i.e. does not stimulate a severe, long-lived or escalating biological response to the formulation when injected into a mammal, in particular a human. To facilitate metabolism of the gel scaffold, degradable linkages can be included through the use of polylactide, polyglycolide, poly(lactide-co-glycolide), polyphosphazine, polyphosphate, polycarbonate, polyamino acid, polyanhydride, and polyorthoester-based building blocks, among others. Additionally, small molecule crosslinking agents containing similar hydrolyzable moieties as the polymers such as carbonates, esters, urethanes, orthoesters, amides, imides, imidoxy, hydrazides, thiocarbazides, and phosphates may be used as building blocks. Additionally, polyglycolide diacrylate, polyorthoester diacrylate and acrylate-substituted polyphosphazine, acrylate-substituted polyamino acid, or acrylate-substituted polyphosphate polymers can be used as degradable building blocks. Methacrylate or acrylamide moieties can be employed instead of acrylate moieties in the above examples. Similarly, small molecules containing a hydrolyzable segment and two or more acrylates, methacrylates, or acrylamides may be used. Such degradable polymers and small molecule building blocks may be functionalized with acrylate, methacrylate, acrylamide or similar moieties by methods known in the art.

In order to be injectability, the system should be in a sol state before administration. The sol state should be of sufficiently low viscosity to allow for small needle head to alleviate the patient discomfort and simplify insertion procedure. Gelation via either chemical cross linking or physical association starts to happen or is complete after injection.

Preferred properties of the gel-forming system include one or more of the following:

The gel-forming system may form a hydrogel. Hydrogels are comprised of cross-linked polymer networks that have a high number of hydrophilic groups or domains. These networks have a high affinity for water, but are prevented from dissolving due to the chemical or physical bonds formed between the polymer chains. Water penetrates these networks causing swelling, giving the hydrogel its form. Fully swollen hydrogels have some physical properties common to living tissues, including a soft and rubbery consistency, and low interfacial tension with water or biological fluids. The elastic nature of fully swollen or hydrated hydrogels can minimize irritation to the surrounding tissues after implantation. A low interfacial tension between the hydrogel surface and body fluid minimizes protein adsorption and cell adhesion, which reduces the risk of an adverse immune reaction. Many polymers used in hydrogel preparations (e.g. polyacrylic acid (PAA), PHEMA, PEG, and PVA) have mucoadhesive and bioadhesive characteristics that enhance drug residence time and tissue permeability. This adhesive property is due to interchain bridges between the hydrogel polymer's functional groups and the mucus glycoproteins, which can help enhance tissue specific binding.

Preferably, before in vivo administration, the gel-forming system according to the invention is a flowable solution. The organic x-ray contrast agent, such as iodinated SAIB derivatives as illustrated in FIG. 7 or other iodinated polymers, and solid inorganic particles can, for example, be added to the gel-forming system simply by mixing before injection. Once injected, the gel-forming system rapidly gels under physiological conditions. An injectable matrix can thus be implanted in the human body with minimal surgical procedure. After gelation in situ, the matrix can provide a reference marker for imaging and image-guided radiotherapy.

A number of activators or conditions can be used to trigger this transition upon injection, either externally applied or in response to the tissue micro-environment. Examples of this include gelation as a response to pH, temperature, ion-concentration, enzymatic activity, electric field and hydration (FIG. 1). In relation to the invention it is relevant to be able to tune the mechanical stability within the tissue to allow for single injections.

Gel-Forming System in Response to Temperature Change

In one embodiment, the gel-forming system undergoes gel-formation in response to a temperature in the range of 10-65° C., preferably in the range 35-40° C.

Figure 2:
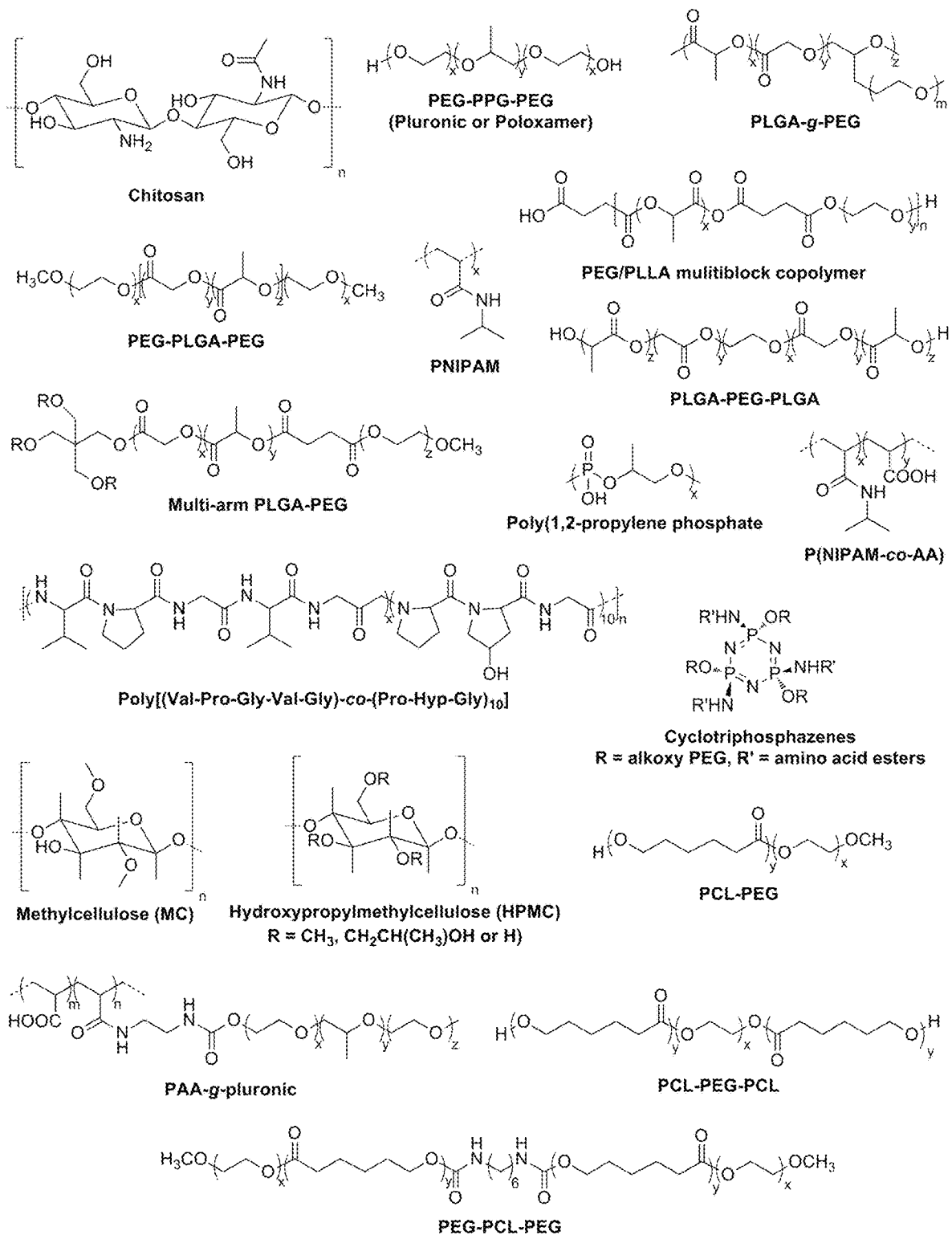

The favored thermosensitive material might exhibit an inverse sol-gel transition. The term "inverse" here means that gelation occurs upon heating instead of cooling. Exemplary biodegradable or bioabsorbable thermogelling polymers are shown in FIG. 2. According to the origin of materials, thermogelling hydrogels can be classified into natural (or seminatural) polymeric systems and synthetic polymeric systems. The polymers in the former system include cellulose, chitosan, xyloglucan, gelatin etc. and their derivatives. The polymers in the latter class include some polyethers, block copolymers of polyethers and biodegradable polyesters, synthetic polypeptides, and other polymers (FIG. 2).

Other examples of such gel-forming systems are those described in; i) Eur. J. Pharm. Biopharm., 2004, 57, 53-63, ii) Chem. Soc. Rev., 2008, 37, 1473-1481, iii) Adv. Drug Deliv. Rev., 2010, 62, 83-99, iv) Macromol. Biosci., 2010, 10, 563-579, v) J. Controlled Release, 2005, 103, 609-624, vi) Expert Opin. Ther. Patents, 2007, 17, 965-977, vii) Appl. Microbiol. Biotechnol., 2011, 427-443, viii) Science, 1998, 281, 389-392, ix) Eur. J. Pharm. Biopharm. 2008, 68, 34-45, x) Biomacromolecules, 2002, 4, 865-868, xi) Colloids and Surfaces B: Biointerfaces, 2011, 82, 196-202, xii) Biomacromolecules, 2010, 11, 1082-1088, xiii) Adv. Eng. Mater., 2008, 10, 515-527, xiv) Eur. J. Pharm. Biopharm., 2004, 58, 409-426, xv) Adv. Drug Deliv. Rev., 2002, 54, 37-51, xvi) Biomater., 2004, 25, 3005-3012, xvii) J. Biomed. Mater. Res., 2000, 50, 171-177, xviii) xix) WO 2007/064252, xx) WO 2009/150651, xxi) WO 2007/064152, xxii) WO 99/07416, xxiii) Park K., Shalaby W. S. W., Park H., *Biodegradable hydrogels for drug delivery*. Basel: Technomic Publishing Co., Inc., 1993. ISBN 1-56676-004-6, Print, xxiv) *Biomedical polymers and polymers therapeutics*, Ed. Chiellini E., Sunamoto J., Migliaresi C., Ottenbrite R. M., Cohn D., New York, Kluwer Academic Publishers, 2002, ISBN 0-30646472-1, Print—and references herein, but not limited to those.

In one interesting embodiment the thermo sensitive polymer is poly(ethylene glycol)-b-poly(propylene glycol)-b-poly(ethylene glycol) (PEG-PPG-PEG, Pluronic® or Poloxamer) or derivates hereof. By controlling the PEG/PPG composition, the molecular weight and the concentration, reversible gelation can occur at physiological temperature and pH.

In another interesting embodiment the thermo sensitive polymer is chitosan. Chitosan can be a thermally sensitive, pH dependent, gel-forming system by the addition of polyol salts (e.g. β-glycerophosphate, GP). These formulations possess a neutral pH, remain liquid at or below room temperature, and form monolithic gels at body temperature. The stability of the sol at room temperature and the gelation time increase as the chitosan degree of deacetylation decreases [Int. J. Pharm., 2000, 203, 89-98]. The gelation for these chitosan-based systems occurs by the combination of charge neutralization, ionic and hydrogen bonds and, as the main driving force, hydrophobic interaction factors. Additionally, such systems are highly compatible with biological compounds and can be used to inject in vivo biologically active growth factors and cells [Biomater., 2000, 21, 2155-2161].

In one very interesting embodiment the thermo sensitive polymer is poly(caprolactone-b-ethylene glycol-b-caprolactone) (PCL-PEG-PCL), poly(ethylene glycol-b-caprolactone-ethylene glycol) (PEG-PCL-PEG) or poly(ethylene glycol-b-caprolactone) (PEG-PCL). This family of block co-polymers can be tuned to be free flowing solutions at room temperature and strong biodegradable gels at body temperature. Such polymers are highly biocompatible having showed very little toxicity with a maximum tolerance dose of 25 g/kg body weight by subcutaneous administration [J. Pharm. Sci., 2009, 98, 4684-4694] and have been found stabile in vivo for more than 4 weeks [Tissue Eng. 2006, 12, 2863-2873].

In another interesting embodiment the thermo sensitive polymer is poly(ethylene glycol-b-[DL-lactic acid-co-glycolic acid]-b-ethylene glycol) (PEG-PLGA-PEG) triblock copolymers. PEG-PLGA-PEG (33 wt %) is a free-flowing sol at room temperature and become a gel at body temperature. The gel showed good mechanical strength and the integrity of gels persisted longer than 1 month [J. Biomed. Mater. Res., 2000, 50, 171-177]. Additional examples includes poly(N-isopropylacrylamide)-g-methylcellulose copolymer as a reversible and rapid temperature-responsive sol-gel hydrogel. By tuning the methylcellulose content gelation temperature, gelation time and mechanical strength can be controlled [Biomater., 2004, 25, 3005-3012].

Gel-Forming System in Response to Change in Ion-Strength

In another embodiment, wherein the gel-forming system undergoes gel-formation in response to change in ion-strength in the range of 1 µM-500 mM—preferably in the range of 1-50 mM or 50-200 mM.

Figure 3:
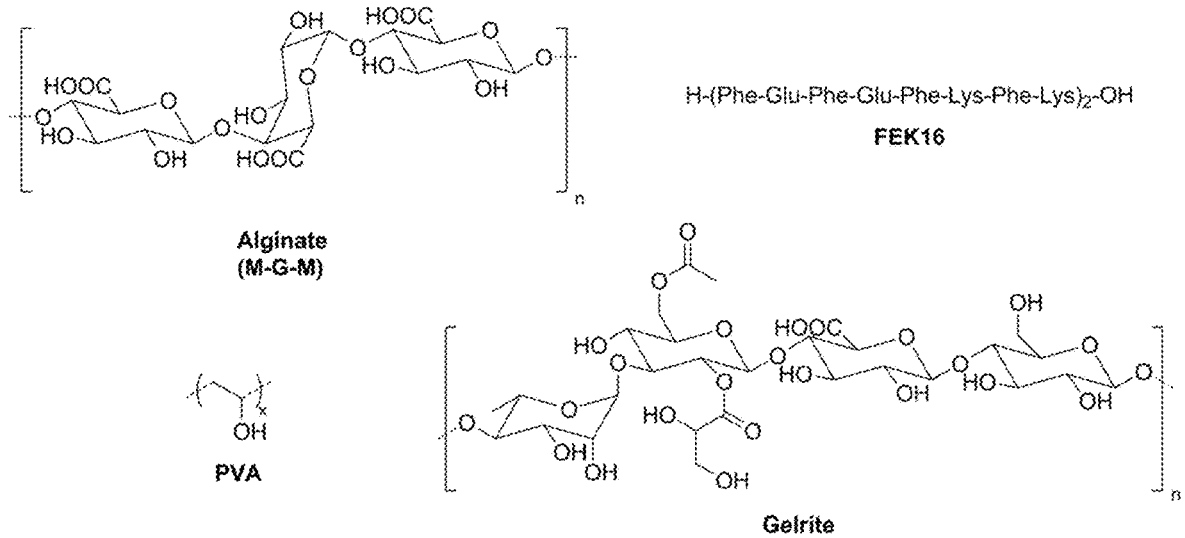

Non-limiting examples of such gel-forming systems include those illustrated in FIG. 3 and those described in i) Int. J. Pharm. 1989, 57, 163-168, ii) J. Controlled Release, 1997, 44, 201-208, iii) J. Am. Chem. Soc., 2001, 123, 9463-9464, iv) J. Controlled Release, 2003, 86, 253-265, v) Biomater., 2001, 22, 511-521, xi) Park K., Shalaby W. S. W., Park H., *Biodegradable hydrogels for drug delivery*. Basel: Technomic Publishing Co., Inc., 1993. ISBN 1-56676-004-6, Print xii) *Biomedical polymers and polymers therapeutics*, Ed. Chiellini E., Sunamoto J., Migliaresi C., Ottenbrite R. M., Cohn D., New York, Kluwer Academic Publishers, 2002, ISBN 0-30646472-1, Print; and references cited therein.

One intriguing example of such a gel-forming system is that of alginate. Alginic acid is an unbranched binary copolymer of 1-4 glycosidically linked L-guluronic acid (G) and its C-5 epimer D-mannuronic acid (M). The proportion as well as the distribution of the two monomers determines to a large extent the physiochemical properties of alginate.

In one embodiment, the gel-forming system is based on an aqueous solution of an alginate. Alginates are a family of linear polysaccharides, which, in aqueous solutions, can gel after addition of multivalent cations. The use of alginate as an immobilizing agent in most applications rests in its ability to form heat-stable strong gels which can develop and set at room temperatures. It is the alginate gel formation with calcium ions which has been of interest in most applications. However, alginate forms gels with most di- and multivalent cations. Monovalent cations and $Mg^{2+}$ ions do not induce gelation while ions like $Ba^{2+}$ and $Sr^{2+}$ will produce stronger alginate gels than $Ca^{2+}$. The gel strength depends on the guluronic content and also of the average number of G-units in the G-blocks. Gelling of alginate occur when divalent cations takes part in the interchain binding between G-blocks giving rise to a three-dimensional network in the form of a gel (FIG. 1). The alginate gel as an immobilization matrix is sensitive to chelating compounds such as phosphate, lactate and citrate, presence of anti-gelling cations such as $Na^+$ or $Mg^{2+}$. To avoid this gel beads may be kept in a medium containing a few millimolar free calcium ions and by keeping the $Na^+/Ca^{2+}$ ratio less than 25:1 for high G alginates and 3:1 for low G alginates. An alternative is also to replace $Ca^{2+}$ with other divalent cations with a higher affinity for alginate. There has been found a correlation between mechanical gel strength and affinity for cations. It has been found that gel strength may decrease in the following orders: $Pb^{2+}>Cu^{2+}=Ba^{2+}>Sr^{2+}>Cd^{2+}>Ca^{2+}>Zn^{2+}>Co^{2+}>Ni^{2+}$ However, in applications involving immobilization of living cells toxicity is a limiting factor in the use of most ions, and only $Sr^{2+}$, $Ba^{2+}$ and $Ca^{2+}$ are considered as nontoxic for these purposes. Alginate gels have been found stable in a range of organic solvents.

Since the gel-inducing factor is added before injection, slow physical gelation is required in order to avoid syringe jam. To combat this, calcium ions can be slowly released from, e.g., $CaSO_4$ powder after the powder has been added to a sodium alginate aqueous solution [J. Biomater. Sci., Polym. Ed., 1998, 9, 475-487]. In another interesting embodiment co-injection of the gel-inducing factor and the aqueous alginate solution using a double syringe results in rapid gelation in the tissue of interest thus avoiding syringe jam. Another interesting embodiment is Gellan gum (Gelrite®, FIG. 3)—a high molecular weight polysaccharide (500 kDa) produced by the microbe *Sphingomonas elodea*. Gellan gum is consists of four linked monosaccharides, including one molecule of rhamnose, one molecule of glucuronic acid and two molecules of glucose. It forms gels when positively charged ions (i.e., cations) are added. Thus, the properties of the gel can be controlled by manipulating the concentration of potassium, magnesium, calcium, and/or sodium salts.

In another interesting embodiment the ion-strength sensitive gel-forming system is a peptide such as H-(FEFEFKFK)$_2$-OH (FEK16) which is known to self-assemble into β-sheet structures in an ionic-strength dependent manner [J. Am. Chem. Soc., 2001, 123, 9463-9464]. FEK16 has been found to be highly soluble in pure $H_2O$ but form self-assembled hydrogels at concentrations >10 mg/mL in the presence of mM concentrations of NaCl, KCl, and $CaCl_2$.

Gel-Forming System in Response to Change in pH

In still another embodiment, the gel-forming system undergoes gel-formation in response to changes in pH. Optionally, the gel-forming system undergoes gel-formation in response to a combined change in pH and temperature, such as a pH in the range of 6-8 and a temperature in the range of 35 to 40° C.

Figure 4:
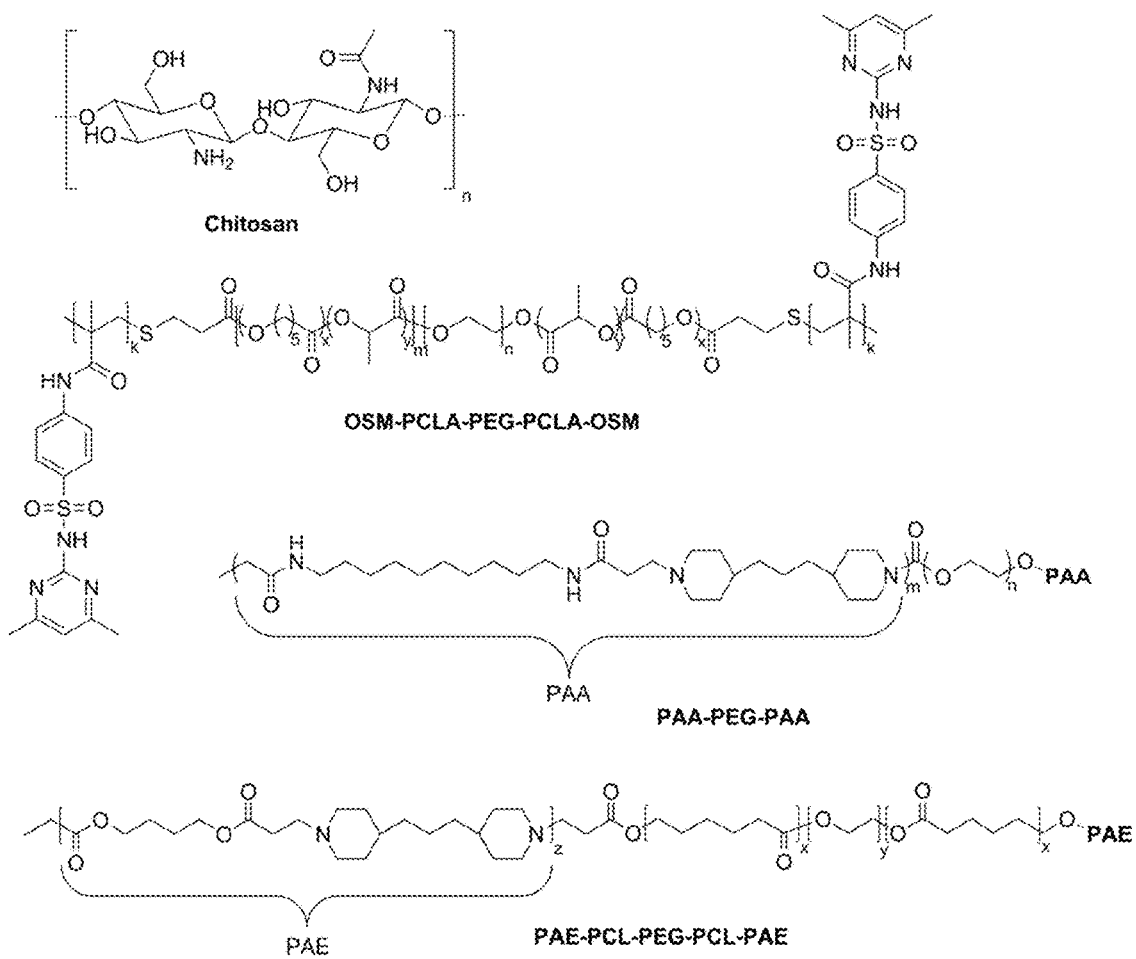

Non-limiting examples of such gel-forming systems are illustrated in FIG. 4, and include those described in i) Macromol. Biosci., 2010, 10, 563-579, ii) J. Controlled Release, 2001, 73, 205-211, iii) Topics in tissue engineering—Smart Polymers, Vol. 3, 2007, Chapter 6, iv) Adv. Drug Delivery Rev., 2010, 62, 83-99, v) J. Controlled Release, 2003, 86, 253-265 vi) *Biodegradable hydrogels for drug delivery*. Basel: Technomic Publishing Co., Inc., 1993. ISBN 1-56676-004-6, Print, vii) *Biomedical polymers and polymers therapeutics*, Ed. Chiellini E., Sunamoto J., Migliaresi C., Ottenbrite R. M., Cohn D., New York, Kluwer Academic Publishers, 2002, ISBN 0-30646472-1, Print, and references cited therein.

The pH of the formulation (before injection) is preferably in the range of pH=2-10, optionally in a range selected from 4-6, 6-8 and 8-9.

The properties of pH responsive hydrogels are highly depending on the $pK_a$ of the ionizable moiety, the hydrophobic moieties in the polymer backbone, their amount and distribution. When ionizable groups become neutral—non-ionized—and electrostatic repulsion forces disappear within the polymer network, hydrophobic interactions dominate. The introduction of a more hydrophobic moiety can offer a more compact conformation in the uncharged state and a more accused phase transition. The hydrophobicity of these polymers can be controlled by the copolymerization of hydrophilic ionizable monomers with more hydrophobic monomers with or without pH-sensitive moieties, such as 2-hydroxyethyl methacrylate, methyl methacrylate and maleic anhydride.

An example of a gel-forming system responsive to pH changes is that which employs the pH-sensitive property of chitosan solutions at low pH. Once injected into the body, these polymer solutions face different environmental pH conditions and form gels. One example is mucoadhesive pH-sensitive chitosan/glyceryl monooleate (C/GMO) in situ gel system which consisted of 3% (w/v) chitosan and 3% (w/v) GMO in 0.33 M citric acid. Chitosan is normally insoluble in neutral or alkaline pH. However, in dilute acids (pH≤5.0), it becomes soluble due to the protonation of free amino groups on the chitosan chains ($RNH_3^+$). The solubility of chitosan in acidic medium also depends on its molecular weight. Acidic solutions of chitosan when exposed to alkaline pH or body biological pH lose this charge and form viscous gels. Chitosan and GMO both own mucoadhesive property which has been applied in drug delivery system. Positive charges on the chitosan backbone may give rise to a strong electrostatic interaction with mucus or a negatively charged mucosal surface.

Gel-Forming System in Response to Enzymatic Activity

In still another embodiment, the gel-forming system undergoes gel-formation in response to enzymatic activity.

Figure 5:
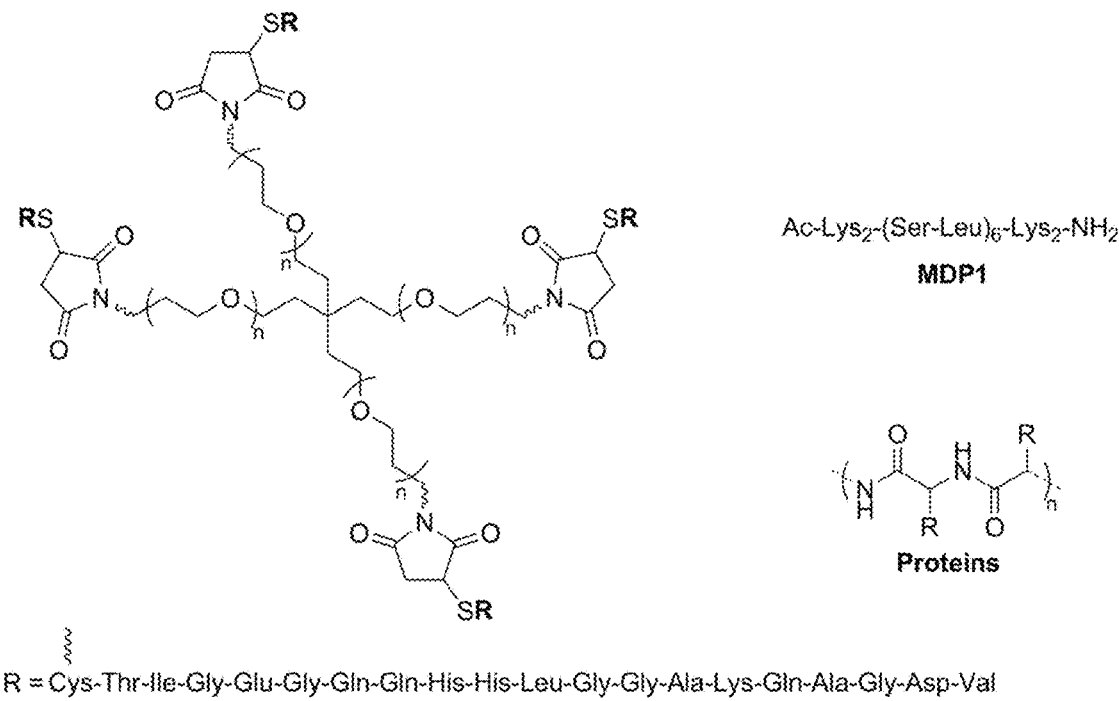

Non-limiting examples of such gel-forming systems are illustrated in FIG. 5 and include those described in i) Tissue Eng., 2006, 12, 1151-1168, ii) Biomater. 2001, 22, 453-462, iii) Biomater., 2002, 23, 2703-2710, iv) Colloids Surf., B, 2010, 79, 142-148, v) Biomacromolecules, 2011, 12, 82-87, vi) Macromolecules 1997, 30, 5255-5264, vii) *Biodegradable hydrogels for drug delivery*. Basel: Technomic Publishing Co., Inc., 1993. ISBN 1-56676-004-6, Print, viii) *Biomedical polymers and polymers therapeutics*, Ed. Chiellini E., Sunamoto J., Migliaresi C., Ottenbrite R. M., Cohn D., New York, Kluwer Academic Publishers, 2002, ISBN 0-30646472-1, Print, and references cited therein.

The enzyme or its origin is not particularly limited. I can be added prior, during or after injection of the gel forming system, thus function as a trigger molecule to induce gel formation. It may be encapsulated in an e.g. liposomes etc. which upon exposure to an internal or external stimuli releases the enzyme. Additionally, the enzyme might be present in the injected tissue, either as a natural tissue component, or as an up-regulated enzyme due to the pathophysiological conditions at the site of injection.

In one embodiment, the enzyme triggered gel-forming system is based on caseins, a group of phosphoproteins with a molecular weight in the range from 20 kDa to 30 kDa. Such system can be turned into a hydrogel by addition of microbial transglutaminase (MTGase), a natural tissue enzyme, at physiological temperature and pH [Colloids Surf., B, 2010, 79, 142-148].

Another interesting example of a gel forming system based on enzymatic activation is based on Schiff base formation of lysine rich peptides due to activation by either lysyl oxidase or plasma amine oxidase [Biomacromolecules, 2011, 12, 82-87]. Oxidation of ε-amino groups of lysine by either lysyl oxidase or plasma amine oxidase results in aldehyde formation which readily forms a Schiff base with an additional ε-amino group of lysine resulting in hydrogel formation.

Gel-Forming System in Response to an Initiator

In still another embodiment, the gel-forming system undergoes gel-formation in response to contact with an initiator, e.g. a molecule or irradiation which results in gel formation by cross linking the gel forming system by the means of a covalent chemical bond.

Non-limiting examples of such gel-forming systems are described in i) U.S. Pat. No. 5,410,016, ii) J. Controlled Release, 2005, 102, 619-627, iii) Macromol. Res., 2011, 19, 294-299, iv) Polym. Bull. 2009, 62-699-711, v) J. Biomater. Sci., Polym. Ed., 2004, 15, 895-904, and references cited therein.

In one embodiment the gel forming system is cross linked by photoinitiation by free radical generation, most preferably in the visible or long wavelength ultraviolet radiation. The preferred polymerizable regions are acrylates, diacrylates, oligoacrylates, methacrylates, dimethacrylates, oligomethoacrylates, or other biologically acceptable photopolymerizable groups. Useful photoinitiators for the above mentioned system which can be used to initiate by free radical generation polymerization of the macromers without cytotoxicity and within a short time frame, minutes at most and most preferably seconds. Preferred dyes as initiators of choice for visible light initiation are ethyl eosin, 2,2-dimethoxy-2-phenyl acetophenone, other acetophenone derivatives, and camphorquinone. In all cases, cross linking are initiated among macromers by a light activated free-radical polymerization initiator such as 2,2-dimethoxy-2-phenylacetophenone or a combination of ethyl eosin and triethanol amine, for example.

In another embodiment the gel forming system is cross linked by hetero- or homo bifunctional linkers such as e.g. dithiothreitol, glutaraldehyde, diphenylmethanebismaleimide, dissucinimidyl suberate, bis(sulfosuccinimidyl) suberate, dimethyl adipim and the like, but not limited to those. An example of such a gel forming system is multiacrylate PEG-based polymers which have been reported to form a hydrogel upon addition of the initiator DTT [J. Controlled Release, 2005, 102, 619-627]. The properties the gel could be fine tuned by controlling the size of the polymer and the amount of initiator added and the gel could be formed under physiological temperature and pH. An additional example of such a system is hydrogel formation by chemically cross-linking an hyaluronic acid (HA) derivative with a hydrazide moiety and another HA derivative with an aldehyde, thus, forming a slowly hydrolysable hydrazone bond [Eur. J. Pharm. Biopharm., 2008, 68, 57-66]. This method has the advantage of allowing in situ cross-linking without the use of initiators, cross-linking chemicals, or extra equipment for cross-linking such as a light source.

Gel-Forming System in Response to Hydration

In still another embodiment, the gel-forming system undergoes gel-formation in response to hydration. Example of such gel-forming systems are those is selected from; i) WO 2006/075123, ii) Adv. Drug Delivery Rev., 2001, 47, 229-250, iii) US 2007/0092560—and references herein, but not limited to those. Formulations composed of neutral diacyllipids and/or tocopherols and/or phospholipids solubilized in biocompatible, oxygen containing, low viscosity organic solvent may form a liquid crystalline phase structure upon hydration, e.g. contact with an aqueous fluid such as extra-vascular fluid, extracellular fluid, interstitial fluid or plasma, but not limited to those. Other systems include non-water soluble high-viscosity liquid carrier materials such as sucrose acetate isobutyrate (SAIB). Such a system may be mixed with solid particles described in the present invention followed by parental injection, thus functioning as a injectable contrast agent which that can be visualized by one or multiple imaging modalities, including X-ray imaging.

Gel-Forming Systems with Cross Linking Groups

In still another embodiment, any of the afore mentioned gel-forming systems, are further functionalized by introducing one or more cross-linkable groups such as acrylate, methacrylate, acrylamide, methacrylamide, vinyl ether, styryl, epoxide, maleic acid derivative, diene, substituted diene, thiol, alcohol, amine, hydroxyamine, carboxylic acid, carboxylic anhydride, carboxylic acid halide, aldehyde, ketone, isocyanate, succinimide, carboxylic acid hydrazide, glycidyl ether, siloxane, alkoxysilane, alkyne, azide, 2'-pyridyldithiol, phenylglyoxal, iodo, maleimide, imidoester, dibromopropionate, and halo acetates, such as bromoacetate, but not limited to those.

Gel-Forming Systems with Chelating Groups

In an additional embodiment, the gel-forming system is comprised of a chelating agent that is known to chelate ions. Any ion chelating agent now known or later discovered may be used in the articles of the present invention. Examples of metal ion (e.g., $Gd^{3+}$ or $Cu^{2+}$) chelating agents include, but are not limited to, expanded porphyrins and porphyrin-like derivatives, DOTA, DTPA, AngioMARK™ (a backbone-functionalized DTPA chelate), DTPA-BMA (a neutral bis-methyl amide derivative of DTPA), and HP-D03A (a DOTA-like macrocyclic compound wherein one chelate arm is replaced with a hydroxylpropyl group). Additional chelates include, but are not limited to, DPDP (TeslaScan™) and Deferoxamine (e.g. $Fe^{3+}$ and $Zr^{4+}$).

Other Constituents of the Formulation

The formulation may further include other constituents, such as α-, β-, and/or γ-cyclodextrins and any derivate hereof. Such constituents may form guest/host complexes with the gel forming system and the nano-sized particles, thus, both aiding in the gel formation and possible alter the particle leakage profile [Adv. Drug Delivery Rev., 2008, 60, 1000-1017]. In one very interesting embodiment the gel forming system is based on PEG-PHB-PEG triblock copolymers, α-cyclodextrin and PEG coated solid nano sized particles. In such a formulation, α-cyclodextrin may form inclusion complexes with both the PEG blocks of the PEG-PHB-PEG triblock copolymers and the PEG coated solid nano sized particles which, combined with hydrophobic interactions between the PHB middle block, forms a strong hydrogel with enhanced retention of solid nano sized particles due α-cyclodextrin interactions which thus altering the particle leakage profile.

The formulation may further comprise compounds or polymers which are visible in imaging modalities other than X-ray imaging.

In one embodiment, the formulation further comprises an iodine-containing polymer, e.g. polyvinylpyrrolidone-iodine (PVP-I), or one selected from i) Polym. Chem., 2010, 1, 1467-1474, ii) U.S. Pat. No. 3,852,341, iii) U.S. Pat. No. 4,406,878, iv) U.S. Pat. No. 5,198,136, v) Biomedical polymers and polymers therapeutics, Ed. Chiellini E., Sunamoto J., Migliaresi C., Ottenbrite R. M., Cohn D., New York, Kluwer Academic Publishers, 2002, ISBN 0-30646472-1, Print, and references cited therein. Such polymers can be added to the gel forming components prior to gelation and function as contrast agent in vivo. Such polymers may additionally or alternatively be covalently bound to the one or more of the gel forming components or adhered to the particles of the present invention.

In one specific embodiment, the formulation consist of SAIB/6,6'-(2,4,6-triiodophenoxy)acetoxy-isobutyric-Sucrose (8)/EtOH. The said combination enables the formation of stabile injectable formulations with very high iodine content which may be used to provide good visualization by one or multiple imaging modalities, including X-ray imaging. High iodine contents (high HU-contrast) is especially important for less sensitive imagining techniques such as e.g. fluoroscopy among others. The iodine concentration of the said formulation consisting of SAIB/6,6'-(2,4,6-triiodo-phenoxy)acetoxy-isobutyric-Sucrose (8)/EtOH can be fine tuned by varying the weight percent (w %), as defined by the weight of the atom/molecule giving x-ray contrast such as iodoine divided by the total weight of the material composition times 100, of 6,6'-(2,4,6-triiodophenoxy)acetoxy-isobutyric-Sucrose (8) added to the matrix. The elemental composition of 6,6'-(2,4,6-triiodophenoxy)-acetoxy-isobutyric-Sucrose (8) is; C, 34.96; H, 3.61; I, 42.62; 0, 18.81, based on this, the overall iodine content (w %) in various formulations can be calculated: SAIB/6,6'-(2,4,6-triiodophenoxy)acetoxy-isobutyric-Sucrose (8)/EtOH (75:5:20) equals 2.13 w %/2.67 w % iodine before/after injection (diffusion of EtOH out of the formulation after injection causes an increases the w % of iodine); SAIB/6,6'-(2,4,6-triiodophenoxy)acetoxy-isobutyric-Sucrose (8)/EtOH (70:10:20) equals 4.26 w %/5.33 w % iodine before/after injection; SAIB/6,6'-(2,4,6-triiodophenoxy)acetoxy-isobutyric-Sucrose (8)/EtOH (60:20:20) equals 8.52 w %/10.66 w % iodine before/after injection; SAIB/6,6'-(2,4,6-triiodophenoxy)acetoxy-isobutyric-Sucrose (8)/EtOH (55:25:20) equals 10.65 w %/13.32 w % iodine before/after injection; SAIB/6,6'-(2,4,6-triiodophenoxy)acetoxy-isobutyric-Sucrose (8)/EtOH (45:35:20) equals 14.92 w %/18.65 w % iodine before/after injection; SAIB/6,6'-(2,4,6-triiodophenoxy)acetoxy-isobutyric-Sucrose (8)/EtOH (30:50:20) equals 21.30 w %/26.64 w % iodine before/after injection.

An increase in iodine concentration of the formulation can directly be correlated to the observed contrast in Hounsfield units (HU). The following contrast (HU) was observed at different energies; 80-, 100-, 120- and 140 kV, all 200 mAs, 2 mm (col 40×0.6 mm) for the following formulations; a) SAIB/6,6'-(2,4,6-triiodophenoxy)acetoxy-isobutyric-Sucrose (8)/EtOH (70:10:20) (4.26 w %/5.33 w % iodine before/after injection) 2500 HU (80 kV), 1800 HU (100 kV), 1500 HU (120 kV) and 1300 HU (140 kV); b) SAIB/6,6'-(2,4,6-triiodophenoxy)acetoxy-isobutyric-Sucrose (8)/EtOH (55:25:20) (10.65 w %/13.32 w % iodine before/after injection) 5000 HU (80 kV), 4500 HU (100 kV), 3500 HU (120 kV) and 3000 HU (140 kV); c) SAIB/6,6'-(2,4,6-triiodophenoxy)acetoxy-isobutyric-Sucrose (8)/EtOH (30:50:20) (21.30 w %/26.64 w % iodine before/after injection) 10500 HU (80 kV), 8800 HU (100 kV), 6200 HU (120 kV) and 5900 HU (140 kV).

The gel-forming formulation may further comprise pharmaceutical agents including prodrugs (in short "drugs"; broadly interpreted as agents which are able to modulate the biological processes of a mammal). Examples of pharmaceutical active agents include small drugs, plasmid DNA (e.g. for gene therapy), mRNA, siRNA, carbohydrates, peptides and proteins. Specific examples of pharmaceutical agents include; a) chemotherapeutic agents such as doxorubicin, mitomycin, paclitaxel, nitrogen mustards, etoposide, camptothecin, 5-fluorouracil, etc.; b) radiation sensitizing agents such as gemcitabine and doranidazole, porphyrins for photodynamic therapy (e.g. visudyne) or 10B clusters or 157Gd for neutron capture therapy; c) peptides or proteins that modulate apoptosis, the cell cycle, or other crucial signaling cascades; d) Anti inflammatory drugs, such as methylprednisolone hemisuccinate, β-methasone; e) Anti anxiety muscle relaxants such as diclofenac, pridinol; f) Local anesthetics such as lidocaine, bupivacaine, dibucaine, tetracaine, procaine; g) Analgesics such as opiods, non-steroidal anti-inflammatory drugs (NSAIDs); h) Antimicrobial medications such as pentamidine, azalides; i) Antipsychotics such as chlorpromazine, perphenazine; j) The antiparkinson agents such as budipine, prodipine, benztropine mesylate, trihexyphenidyl, L-DOPA, dopamine; k) Antiprotozoals such as quinacrine, chloroquine, amodiaquine, chloroguanide, primaquine, mefloquine, quinine; l) Antihistamines such as diphenhydramine, promethazine; m) Antidepressants such as serotonin, imipramine, amitriptyline, doxepin, desipramine; n) Anti anaphylaxis agents such as epinephrine; o) Anticholinergic drugs such as atropine, decyclomine, methixene, propantheline, physostigmine; p) Antiarrhythmic agents such as quinidine, propranolol, timolol, pindolol; q) Prostanoids such as prostaglandins, thromboxane, prostacyclin, but not limited to those. These drugs can be formulated as a single drug or as a combination of two or more of the above mentioned drugs in its active form or as a prodrug.

Additional examples of antitumor agents include camptothecin derivatives such as irinotecan hydrochloride, nogitecan hydrochloride, exatecan, RFS-2000, lurtotecan, BNP-1350, Bay-383441, PNU-166148, IDEC-132, BN-80915, DB-38, DB-81, DB-90, DB-91, CKD-620, T-0128, ST-1480, ST-1481, DRF-1042 and DE-310, taxane derivatives such as docetaxel hydrate, IND-5109, BMS-184476, BMS-188797, T-3782, TAX-1011, SB-RA-31012, SBT-1514 and DJ-927, ifosfamide, nimustine hydrochloride, carboquone, cyclophosphamide, dacarbazine, thiotepa, busulfan, melphalan, ranimustine, estramustine phosphate sodium, 6-mercaptopurine riboside, enocitabine, gemcitabine hydrochloride, carmofur, cytarabine, cytarabine ocphosphate, tegafur, doxifluridine, hydroxycarbamide, fluorouracil, methotrexate, mercaptopurine, fludarabine phosphate, actinomycin D, aclarubicin hydrochloride, idarubicin hydrochloride, epirubicin hydrochloride, daunorubicin hydrochloride, pirarubicin hydrochloride, bleomycin hydrochloride, zinostatin stimalamer, neocarzinostatin, mytomycin C, bleomycin sulfate, peplomycin sulfate, vinorelbine tartrate, vincristine sulfate, vindesine sulfate, vinblastine sulfate, amrubicin hydrochloride, gefitinib, exemestan, capecitabine, TNP-470, TAK-165, KW-2401, KW-2170, KW-2871, KT-5555, KT-8391, TZT-1027, S-3304, CS-682, YM-511, YM-598, TAT-59, TAS-101, TAS-102, TA-106, FK-228, FK-317, E7070, E7389, KRN-700, KRN-5500, J-107088, HMN-214, SM-11355, ZD-0473 and the like.

Additional examples of radiation sensitizing agents include magnesium 5,10,15,20-tetrakis(4-sulphophenyl)-porphine dodecahydrate, PYROA protein (*Emericella nidulans*), photosan III, lomefloxacin, cyamemazine, tiaprofenic acid and the like, but not limited to those.

The drugs are included in the composition in an amount sufficient to achieve a desired effect. The amount of drug or biologically active agent incorporated into the composition depends upon the desired release profile, the concentration of drug required for a biological effect, and the desired period of release of the drug. The biologically active substance is typically present in the composition in the range from about 0.5 percent to about 20 percent by weight relative to the total weight of the composition, and more typically, between approximately 1 percent to about 15 percent by weight. Another preferred range is from about 2 percent to about 10 percent by weight. For very active agents, such as growth factors, preferred ranges are less than 1% by weight, and less than 0.0001%.

Viscosity of the Formulation

The viscosity of the formulation is before the injection preferably lower than 10,000 cP, in particular lower than 2,000 cP, at 20° C. Alternatively, the viscosity of the formulation is before the injection typically lower than 2,000 cP at 5° C.

The organic gel-forming system of the formulation is preferably one which, after injection or under conditions mimicking those in a human body, forms a gel having a viscosity at 37° C. in the range of 2,000 to 50,000,000 cP. More particularly, the viscosity of the hydrogel can be about 2,000 cP, about 5,000 cP, about 10,000 cP, about 20,000 cP, about 30,000 cP, about 50,000 cP, about 75,000 cP, about 100,000 cP, about 125,000 cP, about 150,000 cP, about 200,000 cP, about 30,000 cP, about 800,000 cP, about 1,000,000 cP, about 2,000,000 cP, about 5,000,000 cP, about 10,000,000 cP, about 20,000,000 cP, about 30,000,000 cP, about 40,000,000 cP, about 50,000,000 cP, or ranges thereof. Preferably, the viscosity of the hydrogel after injection (i.e. when present in the desired location) is above 20,000 cP, e.g. in the range of 20,000 cP to 1,000,000 cP. In particular, the formulation after injection is preferably essentially solid.

Use of the Formulation

The present invention also provides the formulation as defined hereinabove for use in X-ray imaging as a marker of specific tissue, such as computer tomography (CT), of the body of a mammal.

In one interesting embodiment, the formulation is parenterally administered to a predetermined location of the body of a human or animal, and wherein an X-ray image of at least a part of the body of the human or animal including the predetermined location is recorded.

A Kit Comprising the Formulation

The present invention further comprises a kit comprising a syringe, a needle used for injection into a body or surgical related procedures, such as but not limited to biopsy, adapted to the open end of said syringe, and a formulation as defined hereinabove. In one embodiment, the formulation is held in the interior or said syringe.

The gel forming system may be provided as a lyophilized powder, a suspension or a solution. Different components may be provided in one or more individual vials or pre-mixed in the interior or said syringe. Exemplary different components include, but are not limited to, the gel-forming system and the solid particles, and the formulation and one or more initiators.

The syringe may consist of a single, a multiple barrel syringe (e.g. MEDMIX SYSTEMS AG) or a double champer syringe (e.g. Debiotech S.A.) and the like, but not limited to those. Multiple barrel syringes and double champer syringes and the like may be useful for e.g. two components formulations were one component is a mixture of the gel forming system and the contrast agent(s) and the other component is an initiator or salt suspension of e.g. $Ca^{2+}$ in the case there the gel forming system is based on alginate.

The needle of the syringe can, in some embodiments, be one suitable for fine-needle biopsies. Non-limiting examples of syringes and needles for such embodiments are described in U.S. Pat. No. 7,871,383, U.S. patent publication No. 20040162505, and references cited therein. Such syringes and needles can advantageously be used in procedures where a biopsy of a tissue is to be taken in conjunction with imaging of the same, using a formulation of the invention. Preferably, the kit has a shelf-life of at least 6 months, such as at least 12 months when stored at, e.g., room temperature (typically 18 to 25° C.) or lower temperatures, such as, e.g., 2 to 10° C., such as about 5° C. The shelf-life can, for example, be determined as the period wherein the kit can be stored at 25° C., at 80% RH and 1 atm. pressure, and where the viscosity is kept within ±5% of the initial viscosity.

A Method of Recording an X-Ray Image of a Body of Animal or Human

The present invention also provides a method of recording an X-ray image of the body of a mammal, comprising the steps of:

(a) providing a formulation comprising an organic gel-forming system that is a homogenous liquid before injection that comprise an organic x-ray contrast agent such as an iodinated compound detectable by X-ray imaging;

(b) administering the formulation to a subject, and (c) recording X-ray-based images, such as Computed Tomography (CT)-images or 2D X-ray images.

In one embodiment, the method is for joint radiotherapy and X-ray imaging of a target tissue in an individual, wherein the images in step (c) provides a definition of the target tissue, and further comprises the step of:

(d) using the definition of the target tissue obtained in c) to direct external beam radiotherapy to the target tissue.

The target tissue is typically one that comprises undesirably growing cells. In one embodiment, the undesirably growing cells are tumor cells, such as malignant cells, and the individual is suffering from or at risk for cancer. In a particular embodiment, the undesirable growth of cells is associated with lung cancer, prostate cancer, cervix or ovarian cancer. Other types of conditions or diseases associated with undesirable cell growth include extra uterine (ectopic) pregnancy, benign tumors in brain, such as benign tumors located closely to the optical nerve, glandule with overproduction of hormone, such as for example hypothalamus, bone and cartilage in relation with nerve compression, blood cells which may be killed prior to transplantation, conditions associated with large tonsils such as acute tonsillitis or adenoiditis, obstructive sleep apnoea, nasal airway obstruction, snoring, or peritonsillar abscess or hyperplasic or angiogenic eye disorders.

In embodiments where the gel-forming system is one that gels upon the addition of an initiator, the administration step (a) or (b) may further comprise mixing with an initiator.

The formulation according to the present invention may be administered parenterally, such as by intravenous, intramuscular, intraspinal, subcutaneous, intraarterial, intracardiac, intraosseous, intradermal, intracisternal, intrathecal, intracerebral, transdermal, transmucosal, inhalational, epidural, sublingual, intravitreal, intranasal, intrarectal, intravaginal or intraperitoneal administration. The parental administration may be performed by, e.g., infusion or injection. Typically, the formulation is administered into, or adjacent to, a predetermined location, such as a target tissue, optionally in conjunction with a biopsy of the target tissue.

The amount of formulation to administer to the mammal or individual in step (c) can be determined by one of skill in the art, taking into consideration the nature of the investigation and the size of the area to be imaged. Typically, at least 100 µL formulation is administered. In various specific embodiments, the method comprises administration of between 100 µL and 20 mL, such as between 200 µL and 10 mL, such as between 200 µL and 2 mL.

In step (c), an X-ray image is typically recorded of at least a part of the body of the mammal including the predetermined location. In particular embodiments, steps (c) and (d) may be performed simultaneously, so that image-recording and execution of radiotherapeutic treatment is integrated and performed sequentially or simultaneously.

Use of the Formulation as a Tissue Sealant

The present invention also provides the formulation as defined herein above for use as a tissue sealant, e.g. for needle canals formed by biopsy in conjunction with an imaging procedure according to the invention.

The tissue sealant may include an effective amount of a hemostatic agent, e.g. an agent selected from coagulation factors, coagulation initiators, platelet activators, vasoconstrictors and fibrinolysis inhibitors, e.g. epinephrine, adrenochrome, collagens, thrombin, fibrin, fibrinogen, oxidized cellulose and chitosan.

SPECIFIC EMBODIMENTS OF THE INVENTION

As said above, the present invention is in one embodiment an X-ray contrast composition for local administration, wherein the X-ray contrast composition exhibits contrast properties and wherein at least 60% of an administrated amount of said X-ray contrast composition remains more than 24 hours within 10 cm from an injection point when the X-ray contrast composition is administrated to a human or animal body. There are various forms of injection forms and routes possible, such as, but not limited to, transcutane injection, using a scope (bronchoscope, gastroscope, or any other flexible wired systems used to navigate inside a body), spraying or just adding on a open wound, attached to another such system, intracranial injection, inside air and fluent filled organs or cavities (e.g. bladder, stomach), or inside non naturally or medically created cavities.

Furthermore, there are various forms of dosing such as, but not limited to, fast injections ('bolus'), pulling back to needle while injecting, slowly injection on the site (e.g. less than 5 seconds, 60 seconds, 120 seconds, 5 minutes, 10 minutes or less than 20 minutes), pulsating the injection, pushing the needle forward, and pump giving a constant pressure for a defined period. Furthermore, there are various devices that may be used such as, but not limited to, needle with 1 or more holes on the side of the needle forming multiple smaller objects, flexible, multiple chamber systems. In one embodiment, the present invention has gelating properties and is a liquid before administration and has the ability to transform into a gel after administration. In one specific embodiment, the present invention has gelating properties and is a homogeneous liquid before administration and has the ability to transform into a gel after administration. Furthermore, in one embodiment the present invention is a non-colloidal x-ray contrast agent as part of a homogeneous liquid x-ray contrast composition that gels upon injection into a human or animal subject. In yet another specific embodiment the X-ray contrast composition is a liquid before administration into a human or animal body that increases in viscosity by more than 100 centipoise (cP), such as e.g. more than 1,000, more than 2,000 or more than 5,000 centipoise (cP), after administration into a human or animal body. According to another specific embodiment of the present invention the X-ray contrast composition is a liquid before administration into a human or animal body that increases in viscosity by more than 10,000 centipoise (cP) after administration into a human or animal body. In another specific embodiment the present invention has a viscosity of less than 10,000 centipoise (cP) at 20° C.

Furthermore, from one perspective of the present invention, the X-ray contrast composition comprises an X-ray contrast agent that is part of the X-ray contrast composition and said X-ray contrast agent is an organic substance. According to one specific embodiment, the organic substance is the contrast "agent" and the X-ray contrast composition comprises alginate and chitosan. In another specific embodiment the X-ray contrast agent comprises one or more natural polymers, synthetic polymers, oligomers, lipids, saccharides, disaccharides, polysaccharides, peptides or any combination thereof and as mentioned before these may be the contrast "agent". In yet another specific embodiment of the present invention the X-ray contrast agent comprises one or more iodinated polymers, oligomers, lipids, saccharides, disaccharides, polysaccharides, peptides, or a derivative or a combination thereof. Further, in one embodiment the X-ray contrast agent is an inorganic acid or salt, such as chloroauric acid.

The present invention may in one embodiment comprise particles for various purposes. One purpose may be an additive contrast effect; another purpose may be to potentiating the effect and a third purpose may be as a carrier of e.g. medication or other substances. According to one specific embodiment of the present invention, the X-ray contrast composition comprises nanoparticles comprising gold (Au). In yet another embodiment the X-ray contrast composition also comprises particles in the size range from 1-1000 nm, such as nanoparticles in the size range from 2 to 500 nm and in one specific embodiment the nanoparticles comprises gold (Au) as the preferred X-ray attenuating element. In yet another embodiment, the X-ray contrast composition comprising nanoparticle that may be an MRI, PET, ultrasound, fluorescence, radiofrequency, visible light contrast agent. Furthermore, in one specific embodiment the nanoparticle is an MRI or PET contrast agent or a combination of the above mentioned imaging modalities.

The present invention may in one embodiment comprise solid particles coated with SH-PNIPAM (MW 3500). By choosing PNIPAM as the coating material various interesting properties can be introduced to the particles. PNIPAM is more hydrophobic compared to e.g. PEG but still water soluble, which enables efficient and straightforward particle coating in aqueous solution without prior extraction to organic solvents. Additionally, by having PNIPAM as the coating material results in a nano composite which can be lyophilized into a powder without inducing particle aggregation etc. which is not possible with other polymers e.g. PEG. Having the solid particles in a powder form is advantageous from multiply perspectives in terms of increased stability, easy storage and straight forward formulation procedures. Furthermore, by having PNIPAM as the only polymer on the solid particles enables the particles to be suspended in organic solvents such as e.g. EtOH for a prolonged period of time without aggregation due to the increased hydrophobicity of the particle introduced by the PNIPAM polymer. By having PNIPAM attached to the solid particles, as the only polymer in the formulation, the hydrophobic interactions with the gel forming solution in terms of e.g. sucrose acetate isobutyrate (SAIB) is increased resulting in a injectable system with very high particle retention. Choosing a more hydrophilic coating material for the particles would induce the release of the solid particles from the gel matrix which can be an advantage or a disadvantage depending on the desired properties of the formulation.

As mentioned previously the present invention may have gelating properties and the gelling may be initiated by various factors such as, but not limited to, temperature, hydration, enzymatic activation, ion concentration and/or pH. In one embodiment the X-ray contrast composition exhibits gel-formation in response to a temperature in the range of 35 to 40° C. In another embodiment the X-ray contrast composition exhibits gel-formation in response to hydration. In yet another embodiment the X-ray contrast composition exhibits gel-formation in response to an ion-concentration in the range of 1 µM to 500 mM, such as in the range of 1 mM to 200 mM. In one embodiment the ions are divalent ions, such as calcium ions. In one embodiment the X-ray contrast composition exhibits gel-formation in response to a pH in the range of 6 to 8. In yet another embodiment, the X-ray contrast composition exhibits gel-formation in response to contacting with an initiator and here an initiator can be many different things such as, but not limited to, ions, or a chemical reactive compound that cross link other molecules.

In one embodiment, the X-ray contrast composition according to the present invention may comprise radioactive compounds, paramagnetic compounds, fluorescent compounds or ferromagnetic compounds, or any mixture thereof.

As mentioned previously, the X-ray contrast composition may also act as a carrier of substances such as, but not limited to, pharmaceutical substances. The substance may be in the composition or in or coated/linked to the nanoparticles. The substance may also be other types of additives. Examples of substance could be, but is not limited to, substances suitable for chemotherapy, gemcitabine, cisplatin, doxorubicin, doranidazole, hormones or anti-bodies. In one embodiment the X-ray composition comprise at least one pharmaceutical substance. In one specific embodiment the X-ray contrast composition comprises particles in the size range from 1-1000 nm, such as nanoparticles in the size range from 2 to 500 nm and wherein the particle contains at least one pharmaceutical substance.

In one embodiment a polymer may be used to work as a stabilizer between gel and biological surrounding and therefore, the X-ray contrast composition may also comprises a molecule that increase gel stability in the human or animal body, such as an interfacially active molecule, such as an amphiphilic molecule, such as an emulsifier. Therefore in one embodiment the X-ray contrast composition comprises poly(ethylene glycol-b-caprolactone) (PEG-PCL), sucrose acetate isobutyrate (SAIB), poly(D,L-lactic acid) (PLA), or poly(lactic-co-glycolic acid) (PGLA), or a combination thereof. In one embodiment of the present invention poly (D,L-lactic acid) (PLA) is added to sucrose acetate isobutyrate (SAIB) gel causing a reduction of burst release of said encapsulated contents e.g. particles drugs etc. Further, in one embodiment, the X-ray contrast composition comprises sucrose acetate isobutyrate (SAIB) or a derivative thereof and in one specific embodiment of the present invention, the X-ray contrast composition comprises an iodinated derivate of sucrose acetate isobutyrate (SAIB). Furthermore in another specific embodiment of the present invention the X-ray contrast composition comprises an iodinated derivate of sucrose acetate isobutyrate (SAIB) doped into sucrose acetate isobutyrate (SAIB). This has been evaluated for stability and the amount of this iodo-SAIB/SAIB that can be doped into SAIB, is at least 50 w/w %.

The iodo-SAIB provides high X-ray contrast. The iodo-SAIB compound is poorly soluble in ethanol and is a white solid whereas SAIB is highly soluble in ethanol and is a thick oil. However, a mixture of ethanol and SAIB can solubilize the iodo-SAIB very nicely. This means that the SAIB helps solubility of iodo-SAIB, which is an interesting feature and which provides an injectable solution which forms a biodegradable, amorphous carbohydrate glass matrix after administration (through a thin needle, thinner than 20 gauge) that can function as a high contrast X-ray marker. When injected into mice, the iodo-SAIB/SAIB provides high contrast and has the desirable stability properties. Furthermore, the gel is homogeneous. In one embodiment of the present invention the X-ray contrast composition comprises an iodinated derivate of sucrose acetate isobutyrate (SAIB) solubilized in a mixture of ethanol and sucrose acetate isobutyrate (SAIB).

One way of containing and also storing the composition may be, held in the interior of a syringe. This indicates a possible shelf-life of at least 6 months. One embodiment of the present invention is a kit comprising a syringe, a needle used for injection into a body or surgical related procedures such as but not limited to biopsy adapted to the open end of said syringe, and a composition according to the present invention.

In one embodiment of the present invention, the X-ray contrast composition comprises an iodinated derivate of sucrose acetate isobutyrate (SAIB) and contains a pharmaceutical substance. In another embodiment the X-ray contrast composition comprises an iodinated derivate of sucrose acetate isobutyrate (SAIB) and contains particle that contains a pharmaceutical substance. In yet another embodiment, the X-ray contrast composition comprises an iodinated derivate of sucrose acetate isobutyrate (SAIB) solubilised in a mixture of ethanol and sucrose acetate isobutyrate (SAIB) and contains a pharmaceutical substance. Furthermore, in one specific embodiment of the present invention, the X-ray contrast composition comprises an iodinated derivate of sucrose acetate isobutyrate (SAIB) solubilised in a mixture of ethanol and sucrose acetate isobutyrate (SAIB) and contains a particle that contains a pharmaceutical substance.

The intended use of the present invention is for radio therapy or image-guided radiation therapy, but not exclusively, other uses are thinkable such as, but not limited to, 2D X-ray scans, for use in imaging, diagnostics, treatment and/or quality rating of radiation therapy. The present invention may be used as a tissue marker and/or for use as a controlled drug release composition.

In one embodiment the X-ray contrast composition according to the present invention is for use in administration of an amount of 0.01-5.0 mL and in one specific embodiment the X-ray contrast composition is for use in administration wherein the amount is 0.1-1.0 mL. In one embodiment the present invention may be used as a tissue sealant.

In one embodiment the X-ray contrast composition according to the present invention, the X-ray contrast composition is parenterally administered to a predetermined location of the body of a mammal, and wherein an X-ray image of at least a part of the body of the mammal including the predetermined location is recorded. Further, an embodiment of the invention may comprise a method of recording an X-ray image of the body of a mammal, comprising the steps of
  a. providing an X-ray contrast composition comprising an organic X-ray agent in a gel-forming system;
  b. administering the X-ray contrast composition to a predetermined location of the mammal, and
  c. recording X-ray-based images of at least a part of the body which comprises the predetermined location.

In another embodiment, the invention comprise a method of joint radiotherapy and X-ray imaging of a target tissue in a mammal, comprising the steps of
  a. providing an X-ray contrast composition comprising an organic X-ray agent in a gel-forming system;
  b. administering the X-ray contrast composition to a predetermined target tissue of the mammal,
  c. recording X-ray-based images, of at least a part of the body which comprises the target tissue, thereby providing a definition of the target tissue, and
  d. using the definition of the target tissue obtained in c) to direct external beam radiotherapy to the target tissue.

Steps (c) and (d) may potentially be performed simultaneously.

In another embodiment, the invention comprise a method for directing local administration of a pharmaceutical agent to a target tissue in a mammal, comprising the steps of
  a. providing an X-ray contrast composition comprising an organic X-ray agent in a gel-forming system;
  b. administering the X-ray contrast composition to a predetermined target tissue of the mammal,
  c. recording X-ray-based images, of at least a part of the body which comprises the target tissue, thereby providing a definition of the target tissue, and
  d. using the X-ray contrast composition in b) to further comprise an pharmaceutical agent for delivery of a pharmaceutical agent to a predetermined target tissue of the mammal.

Steps (c) and (d) may potentially be performed simultaneously.

In one specific embodiment of the present invention the target tissue comprises undesirably growing cells and in another specific embodiment the target tissue comprises tumor cells.

DETAILED DESCRIPTION OF THE DRAWINGS

FIG. 1. Illustrates various mechanisms of gel-formation including thermo-, ion-, pH-, enzymatically-, initiator- and hydration responsive gel-forming systems.

FIG. 2. Illustrates various thermo responsive gel-forming systems which can exhibit an inverse sol-gel transition.

FIG. 3. Illustrates various ion sensitive gel-forming systems which form gels in high salt concentration.

FIG. 4. Illustrates various pH sensitive gel-forming systems which form hydrogels at specific pH intervals.

FIG. 5. Illustrates various enzymatically sensitive gel-forming systems which form hydrogels in presence of specific enzymes.

Figure 6:
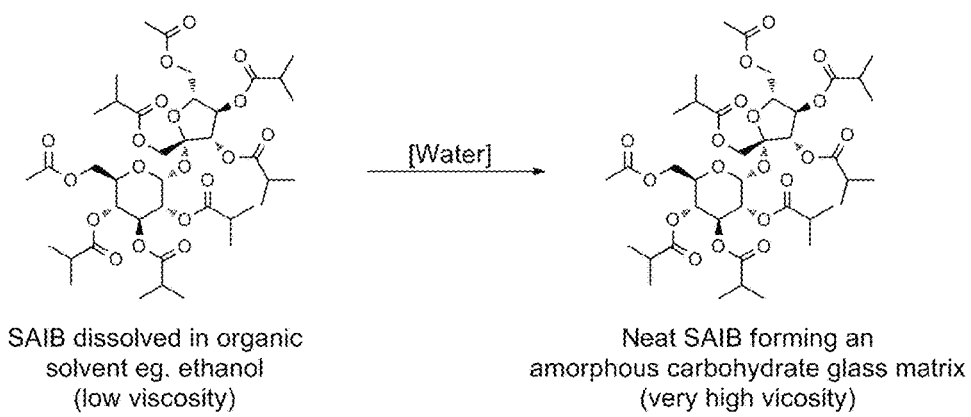

FIG. 6. Illustrates the use of sucrose acetate isobutyrate (SAIB) as a hydration sensitive gel-forming system. SAIB dissolved in organic solvent such as ethanol have a low viscosity suitable for injection trough thin needles. Upon hydration the ethanol diffuses out of the matrix resulting in a highly viscous hydrophobic gel suitable for encapsulation of contrast agents.

FIG. 7. Illustrates various iodo-SAIB derivates which may be used for x-ray attenuation.

Figure 8:
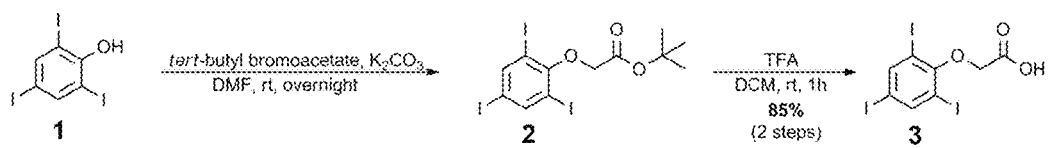

FIG. 8. Illustrates a synthetic scheme for the synthesis of 2-(2,4,6-triiodophenoxy)acetic acid (3)

Figure 9:
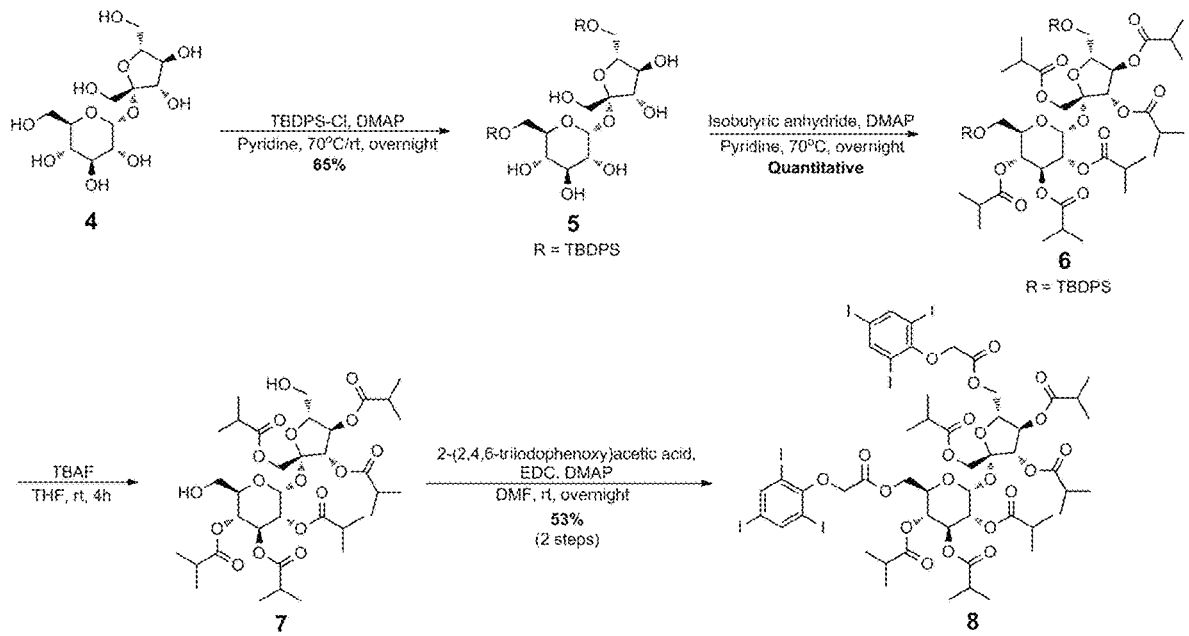

FIG. 9. Illustrates a synthetic scheme for the synthesis of 6,6'-(2,4,6-triiodophenoxy)acetoxy-isobutyric-Sucrose (8)

Figure 10:
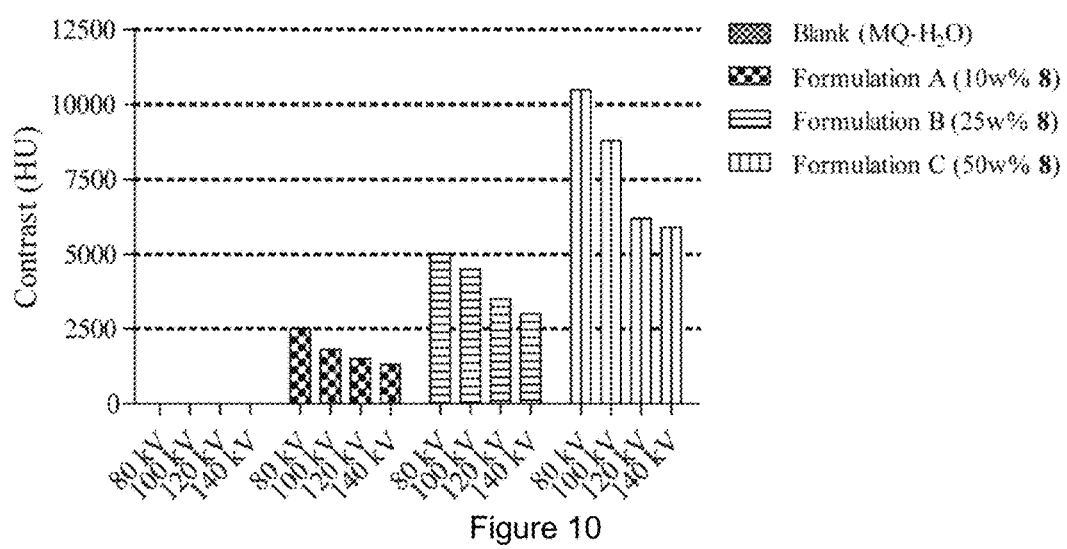

FIG. 10. Illustrates CT-contrast of iodinated gels with 10-, 25-, or 50 w % (8) ((w % is the weight of the atom/molecule (in this case iodine) divided by the total weight of the material times 100)) and a negative control containing $MQ-H_2O$ were visualized in a clinical CT-scanner at different energies; 80-, 100-, 120- and 140 kV, all 200 mAs, 2 mm (col 40×0.6 mm).

Figure 11:
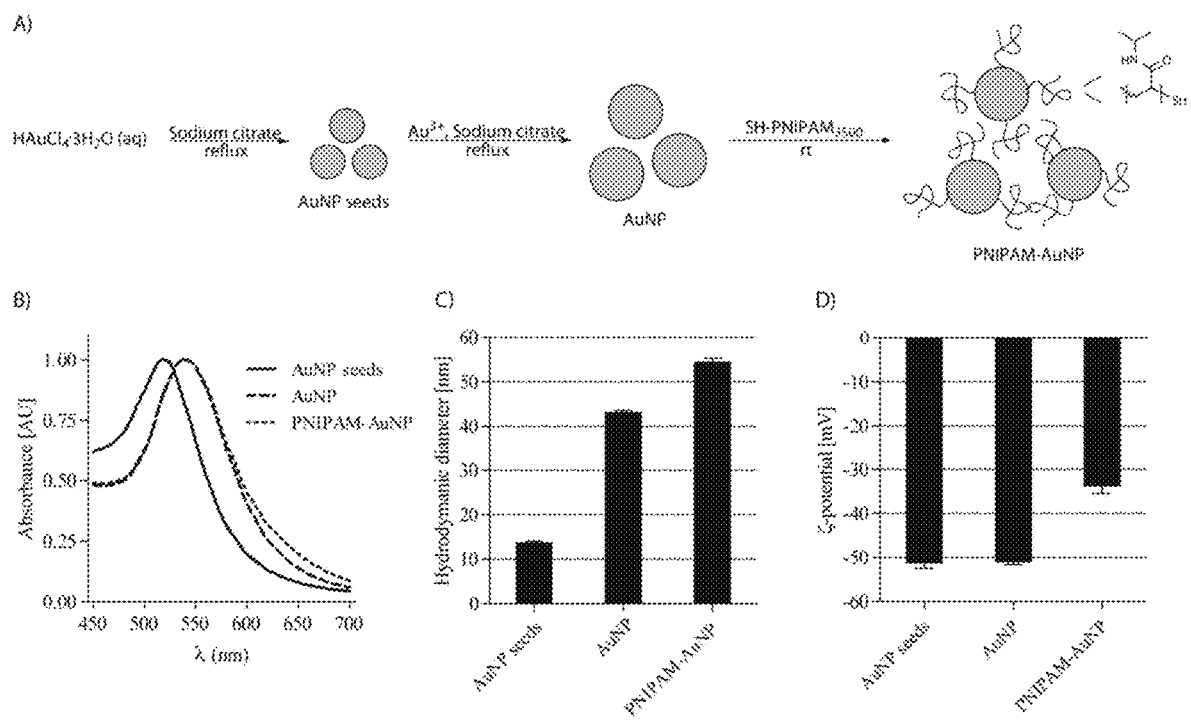

FIG. 11. Illustrates AuNP synthesis and characterization. A) Synthetic scheme for the synthesis of PNIPAM-coated AuNPs using a seeding approach; B) AuNP characterization by UV-Vis; C) AuNP characterization by DLS; D) AuNP characterization by ζ-potential.

Figure 12:
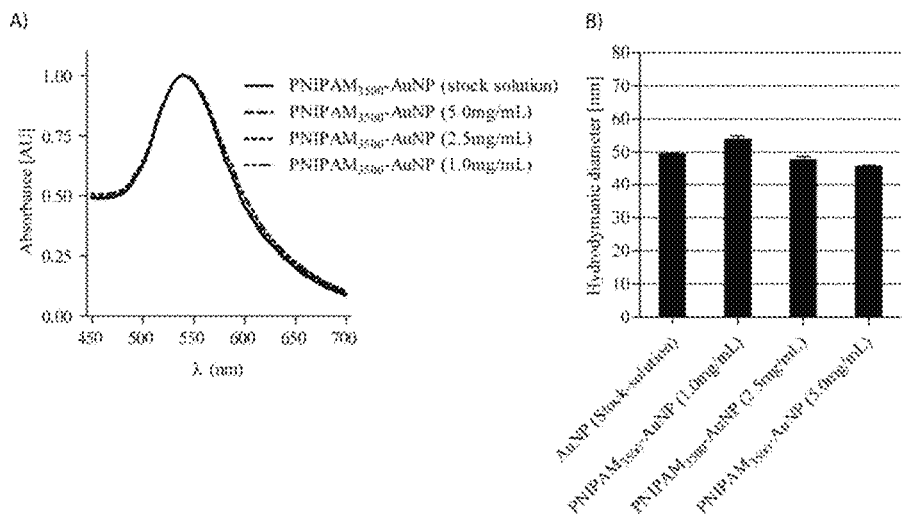

FIG. 12. Illustrates the enhanced stability of PNIPAM coated AuNPs. A) UV-Vis of PNIPAM coated AuNPs before (stock)/after lyophilization and re-suspension in anhydrous EtOH (concentration of AuNP in the range of 1.0-5.0 mg Au/mL); B) DLS of PNIPAM coated AuNPs before (stock)/after lyophilization and re-suspension in anhydrous EtOH (concentration of AuNP in the range of 1.0-5.0 mg Au/mL).

Figure 13:
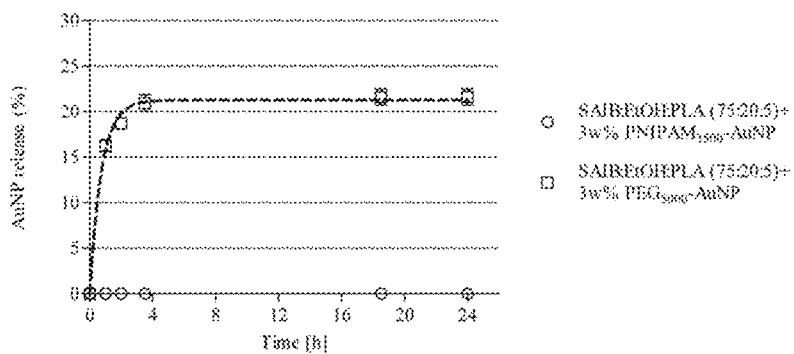

FIG. 13. Illustrates the accumulative release of PNIPAM$_{3500}$- and PEG$_{5000}$ coated AuNPs from gels composed of SAIB/EtOH/PLA (75:20:5)+3.0 w % PNIPAM$_{3500}$ or PEG$_{5000}$ coated AuNPs.

Figure 14:
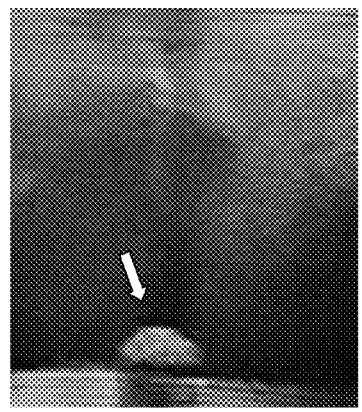

FIG. 14. Illustrates a ultrasonography image of Formulation B (SAIB/8/EtOH (55:25:20)) (250 µL) in vitro. Gel present at the bottom of a glass beaker under water.

Figure 15:
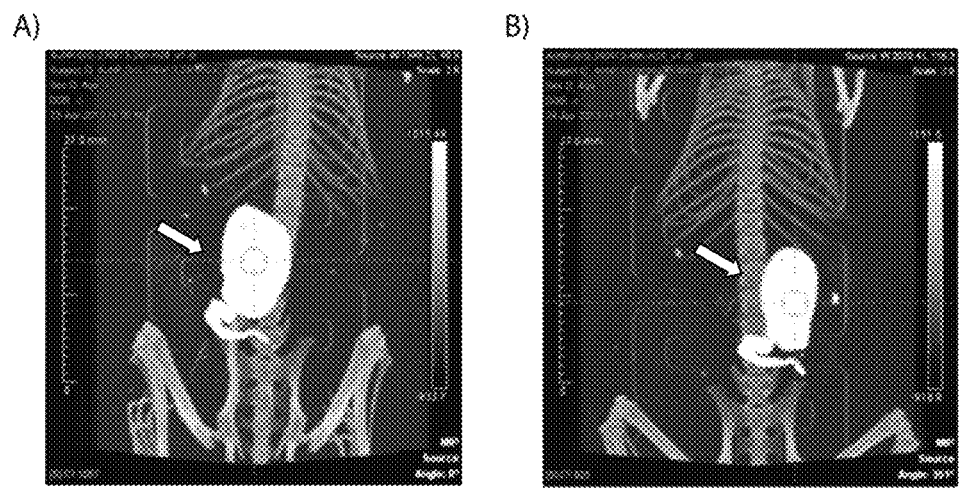

FIG. 15. Illustrates MicroCT images of Formulation B (SAIB/8/EtOH (55:25:20)) (200 µL) administered by subcutaneous injection to healthy NMRI mice. A) CT-image recorded 24 h p.i.; B) CT-image recorded 48 p.i.

Figure 16:
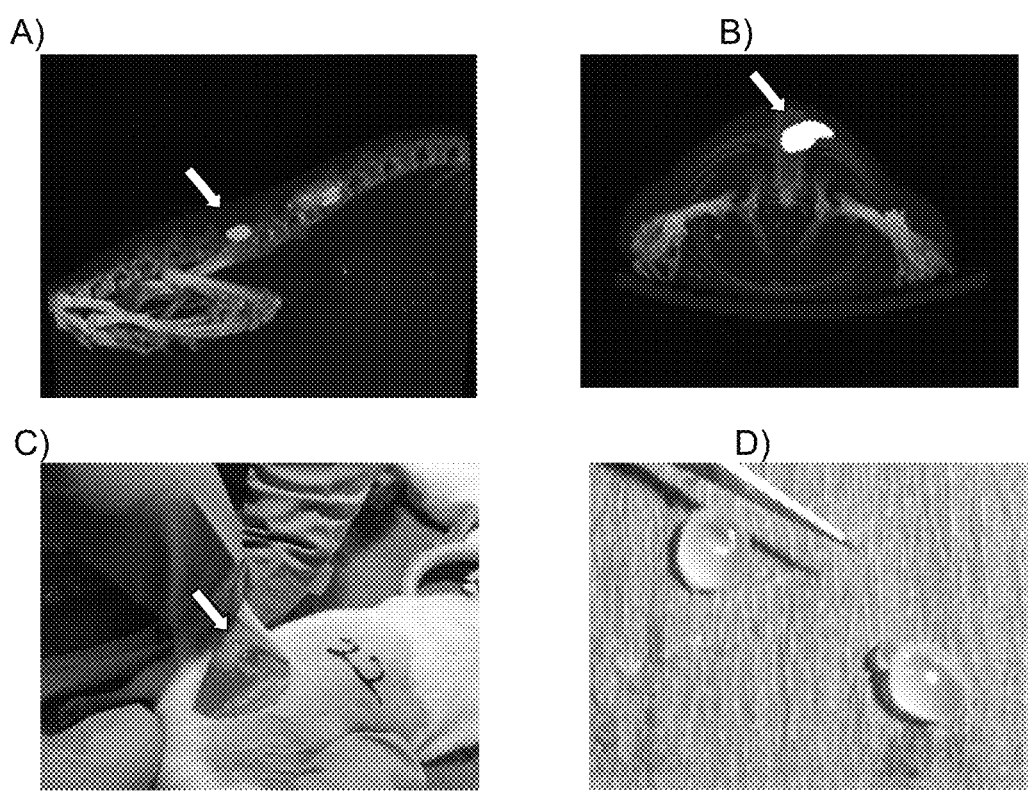

FIG. 16. A) MicroCT image of SAIB/8/EtOH (65:15:20) injected s.q. in immunocompetent mice; B) MicroCT image of SAIB/8/EtOH (50:30:20) injected s.q. in immunocompetent mice; C) Ex vivo visualization of SAIB/8/EtOH (50:30:20) present in the s.q. compartment 14 w p.i. and D) Gel implants composed of SAIB/8/EtOH (50:30:20) removed after 14 w implantation in immunocompetent mice.

Figure 17:
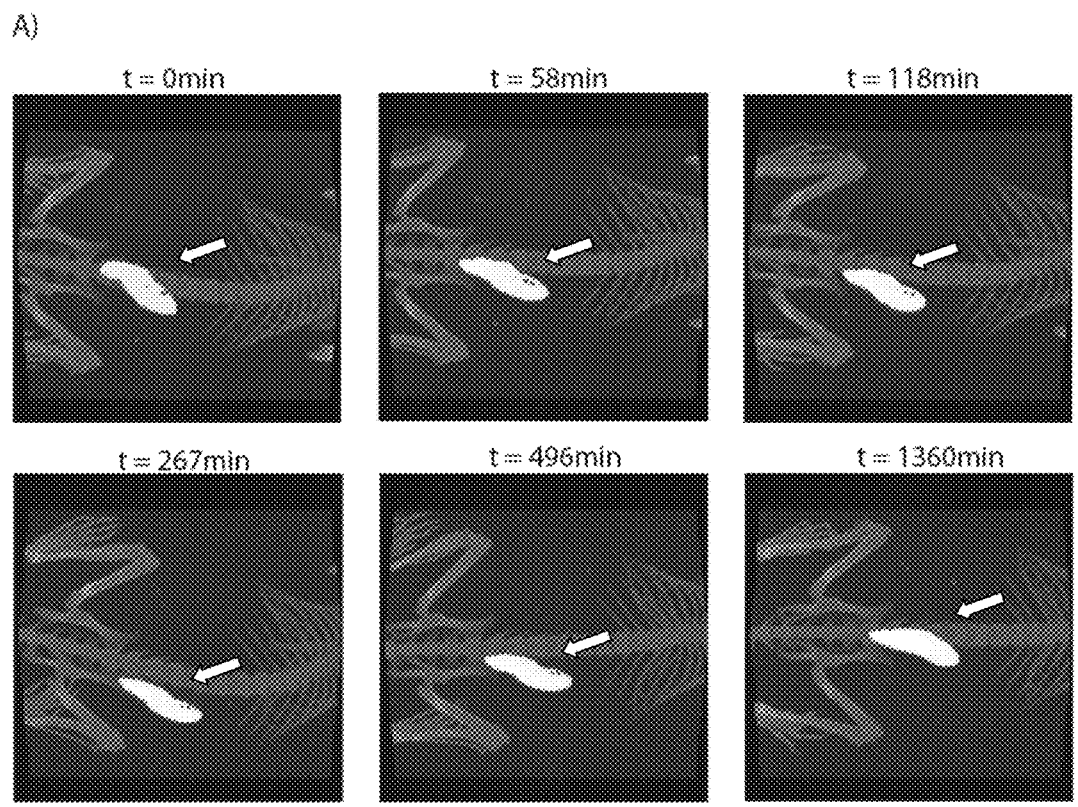
Figure 17:
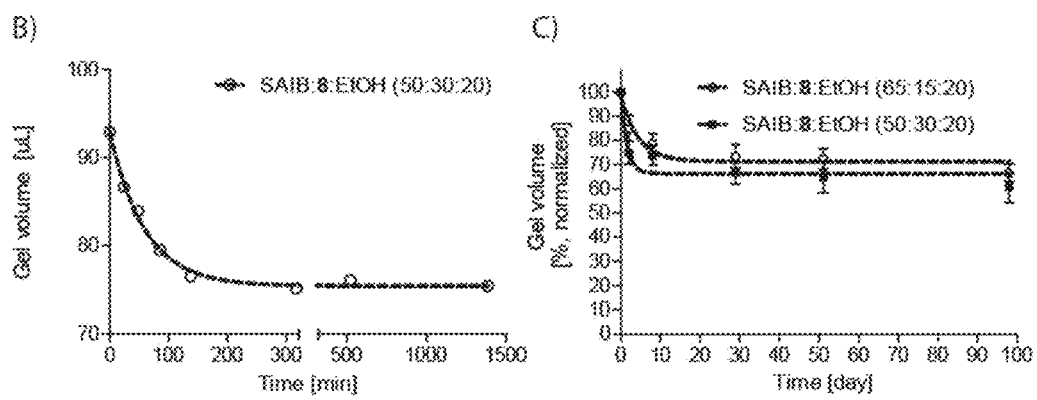

FIG. 17. A) Series of MicroCT images of SAIB/8/EtOH (50:30:20) injected s.q. in mice. MicroCT scans recorded with short time intervals to monitor the gelation kinetics of the iododinated gel; B) Gelation kinetics of SAIB/8/EtOH (50:30:20) (50 µL) implanted s.q. in immunocompetent mice and C) 14 w degradation profiles of iododinated gels composed of SAIB/8/EtOH (65:15:20) or SAIB/8/EtOH (50:30:20) after s.q. implantation (50 µL).

Figure 18:
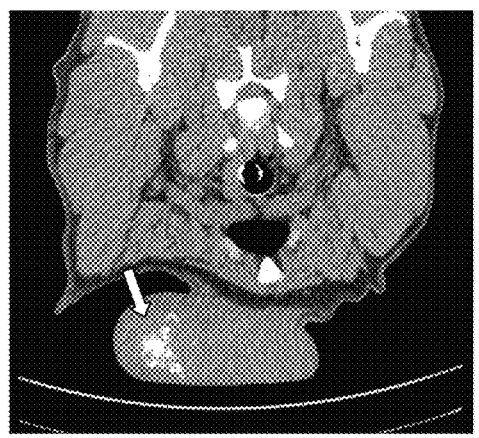

FIG. 18. Illustrates a CT-image of Formulation B (SAIB/8/EtOH (55:25:20)) administrated intratumoral to a companion dog (American Staffordshire terrier, 9 years, 34 kg) with a mast cell tumor present between the front legs.

EXAMPLES

Example 1

Iodo-SAIB Gel Formation and CT-Contrast In Vitro

Materials

Chemicals were purchased from Sigma-Aldrich Inc. (Brøndby, Denmark) unless otherwise stated. 2-(2,4,6-triiodophenoxy)acetic acid (3) and 6,6'-(2,4,6-triiodophenoxy)acetoxy-isobutyric-Sucrose (8) was synthesized in two and four steps, respectively, as outlined in FIG. 7 and FIG. 8.

Synthesis

2-(2,4,6-triiodophenoxy)acetic acid (3)

2,4,6-triiodophenol (1) (10.00 g, 21.2 mmol) was dissolved in dry DMF (75 mL) under N$_2$-atmosphere. To this solution, tert-butyl bromoacetate (4.20 mL, 28.46 mmol) and K$_2$CO$_3$ (8.79 g, 63.6 mmol) were added and the stirred overnight at rt. The solvent was removed in vacou and the remaining yellow oil re-dissolved in EtOAc (150 mL) and washed with MQ-H$_2$O (3×150 mL). The organic phase was dried with MgSO$_4$, filtrated and concentrated in vacou to give tert-butyl 2-(2,4,6-triiodophenoxy)acetate (2) as a light yellow oil which was used in the next step without further purification. 2 was dissolved in CH$_2$Cl$_2$ (60 mL) and trifluoroacetic acid (30 mL) was added. The mixture stirred for 1 h at rt after which the solvent was removed in vacou to give a white solid. The crude product was re-crystallized from EtOH to give 2-(2,4,6-triiodophenoxy)acetic acid (3) as fine white needles (9.58 g, 85% (2 steps)). $^1$H-NMR (300 MHz, MeOD): δ 6.58 (s, 2H), 2.95 (s, 2H). MALDI-TOF MS (DHB+Na): Chemical Formula: C$_8$H$_5$I$_3$NaO$_3$, calculated mass; 552.83. found: 553.08 (M+Na$^+$).

6,6'-TBDPS-Sucrose (5)

Sucrose (4) (3.00 g, 8.76 mmol) was dissolved in dry pyridine (54.0 mL) under N$_2$-atmosphere. To this solution tert-butyldiphenylchlorosilane (TBDPS-Cl) (2.51 mL, 9.64 mmol) and a catalytic amount of DMAP (107.5 mg, 0.88 mmol) were added and the mixture heated at 70° C. for 3 h. After cooling to rt, TBDPS-Cl (2.51 mL, 9.64 mmol) was added and the mixture stirred overnight at rt. The solvent was removed in vacou and the crude product purified by flash chromatography using a stepwise gradient starting from; i) EtOAc, ii) EtOAc/Acetone/H$_2$O (100:100:1) and iii) EtOAc/Acetone/H$_2$O (10:10:1) as eluent to give 6,6'-TBDPS-Sucrose (5) as a white solid (4.66 g, 65%). R$_f$=0.40 (EtOAc/Acetone/H$_2$O (100:100:1)). MALDI-TOF MS (DHB+Na): Chemical Formula: C$_{44}$H$_{57}$NaO$_{11}$Si$_2$, calculated mass; 841.08. found: 841.81 (M+Na$^+$).

6,6'-TBDPS-isobutyric-Sucrose (6)

6,6'-TBDPS-Sucrose (5) (3.00 g, 3.66 mmol) was dissolved in dry pyridine (45.0 mL) under N$_2$-atmosphere. To this solution isobutyric anhydride (15.00 mL, 90.4 mmol) was added and the mixture stirred at rt overnight. Additional isobutyric anhydride (5.0 mL, 15.06 mmol) and a catalytic amount of 4-dimethylaminopyridine (DMAP) (50 mg, 0.41 mmol) were added and the mixture heated to 70° C. for 6 h. The solvent was removed in vacou and the crude product purified by flash chromatography using hexane:EtOAc (5:1) as eluent to give 6,6'-TBDPS-isobutyric-Sucrose (6) as clear viscous oil (4.54 g, quantitative). R$_f$=0.48 (hexane:EtOAc (5:1). MALDI-TOF MS (DHB+Na): Chemical Formula: C$_{68}$H$_{94}$NaO$_{17}$Si$_2$, calculated mass; 1262.62. found: 1262.22 (M+Na$^+$).

6,6'-OH-isobutyric-Sucrose (7)

6,6'-TBDPS-isobutyric-Sucrose (6) (217.2 g, 0.175 mmol) was dissolved in THF (940 mL) and stirred at RT. Glacial acetic acid (42.1 g, 0.701 mol) was added to the flask followed by addition of tetrabutyl-ammonium fluoride trihydrate (TBAF.3H$_2$O) (221.1 g, 0.701 mol) in THF (692 mL). The solution was stirred at RT for 15 h after which heptanes (2085 mL) and phosphate buffer (0.5M, 211 mL) (H$_2$KPO$_4$ (177.2 g) and HK$_2$PO$_4$ (343.3 g) in MQ-H$_2$O (6544 mL)), pH 7.0) was added. The organic phase was collected and washed with additionally two portions of phosphate buffer (0.5M, 2111 mL). The crude product purified by flash chromatography using a gradient starting from hexanes:EtOAc (7:3) then hexanes:EtOAc (6:4) as eluent to give 6,6'-OH-isobutyric-Sucrose (7) as clear viscous oil (106.1 g, 79%). R$_f$=0.21 (hexane:EtOAc (3:1). $^1$H-NMR (300 MHz, DMSO-d$_6$): δ 5.75 (d, J=6.1 Hz, 1H), 5.50 (d, J=3.6 Hz, 1H), 5.40 (d, J=7.7 Hz, 1H), 5.31 (t, J=7.4 Hz, 1H), 5.18 (t, J=9.8 Hz, 1H), 4.87 (t, J=5.5 Hz, 1H), 4.70 (dd, J=10.4, 3.7 Hz, 1H), 4.29 (d, J=11.9 Hz, 1H), 4.11 (dd, J=12.0, 5.5 Hz, 1H), 3.69-3.44 (m, 4H), 2.64-2.49 (m, 6H), 1.13-0.96 (m, 36H). MALDI-TOF MS (DHB+Na): Chemical Formula: C$_{36}$H$_{58}$NaO$_{17}$, calculated mass; 785.83. found: 785.82 (M+Na$^+$).

6,6'-(2,4,6-triiodophenoxy)acetoxy-isobutyric-Sucrose (8)

6,6'-OH-isobutyric-Sucrose (7) (800 mg, 1.05 mmol) was dissolved in dry DMF (10.0 mL) under N$_2$-atmosphere. To this solution a pre-mixed mixture of 2-(2,4,6-triiodophenoxy)acetic acid (3) (1.67 g, 3.15 mmol), EDC.HCl (622 mg, 3.15 mmol) and DMAP (769 mg, 6.29 mmol) in dry DMF (10.0 mL) were added and the reaction stirred at rt overnight. The solvent was removed in vacou and the remaining yellow oil re-dissolved in $CH_2Cl_2$ (40 mL) and washed with $MQ-H_2O$ (3×40 mL). Organic phase was dried with $MgSO_4$, filtrated and reduced in vacou to give light yellow oil. Final purification was achieved by flash chromatography using hexane:EtOAc (5:1) as eluent to give 6,6'-(2,4,6-triiodophenoxy)acetoxy-isobutyric-Sucrose (8) as white foamy solid (1.56 g, 83%). $R_f$=0.31 (hexane:EtOAc (5:1). $^1$H-NMR (300 MHz, MeOD): δ 8.05 (s, 2H), 8.04 (s, 2H), 5.68 (d, J=3.7 Hz, 1H), 5.56 (d, J=7.3 Hz, 1H), 5.54-5.48 (m, 1H), 5.43 (t, J=7.2 Hz, 1H), 5.37 (t, J=9.8 Hz, 1H), 5.03 (dd, J=10.2, 3.7 Hz, 1H), 4.70-4.06 (m, 12H), 2.73-2.45 (m, 6H), 1.36-1.04 (m, 36H). MALDI-TOF MS (DHB+Na): Chemical Formula: $C_{52}H_{64}I_6NaO_{21}$, calculated mass; 1809.47. found: 1809.59 (M+Na$^+$).

Gel Preparation

Three sucrose acetate isobutyrate (SAIB)-based formulations (600 mg each) with increasing amounts of 6,6'-(2,4,6-triiodophenoxy)acetoxy-isobutyric-sucrose were prepared as outlined in the table below.

| Formulation | SAIB | 6,6'-(2,4,6-triiodophenoxy)-acetoxy-isobutyric-sucrose (8) | EtOH |
|---|---|---|---|
| A SAIB/8/EtOH (70:10:20) | 420 mg | 60 mg | 120 mg |
| B SAIB/8/EtOH (55:25:20) | 330 mg | 150 mg | 120 mg |
| C SAIB/8/EtOH (30:50:20) | 180 mg | 300 mg | 120 mg |

SAIB-solution (90 w/w in EtOH) was weighted off and mixed with 8 and anhydrous EtOH (see table above). The mixtures were homogenized on a ball-mill homogenizer for 60 min (30 s$^{-1}$) and centrifuged for 20 s at 5000 RPM to remove air bubbles from the formulations. All formulations were homogenous clear solutions with increasing viscosity as a function of the concentration of 8—all injectable trough 25 G hypodermic needles.

Iodinated gels (500 μL) from formulation A-C were prepared by injection into $MQ-H_2O$ (5.0 mL) containing plastic vials at 37° C. The aqueous solutions were replaced three times and the gels stored at 37° C. for 12 days prior to CT-visualization and HU-contrast measurements in a clinical CT-scanner.

CT-Contrast of Iodinated Gels In Vitro

The three formed iodinated gels with 10-, 25-, or 50 w % 8 and a negative control containing $MQ-H_2O$ were visualized in a clinical CT-scanner at different energies; 80-, 100-, 120- and 140 kV, all 200 mAs, 2 mm (col 40×0.6 mm). The obtained contrast in Hounsfield unit (HU) plotted as a function of energy is illustrated in FIG. 10 and listed in the table below. Excellent contrast ranging from 1.300-10.500 HU was observed dependent on the w % of 8 and the applied energy.

| Formulation | w % iodine (before injection) | 80 kV | 100 kV | 120 kV | 140 kV |
|---|---|---|---|---|---|
| A | 4.26 w % | 2500 HU | 1800 HU | 1500 HU | 1300 HU |
| B | 10.65 w % | 5000 HU | 4500 HU | 3500 HU | 3000 HU |
| C | 21.30 w % | 10500 HU | 8800 HU | 6200 HU | 5900 HU |

As may be understood from above, according to one specific embodiment of the present invention, the X-ray contrast composition is a liquid before administration into a human or animal body and having an iodine concentration of more than 1.5 w % before injection, such as 2-30 w %, such as 3-25 w %, such as 4-25 w %.

Example 2

Synthesis and Improved Properties of PNIPAM-Coated AuNP

Materials

Chemicals were purchased from Sigma-Aldrich Inc. (Brøndby, Denmark) unless otherwise stated. $HAuCl_4 \times 3H_2O$ was purchased from Wako Chemicals GmbH (Neuss, Germany) and SH-PNIPAM (MW 3500, PDI=1.24) was purchased from Polymer Source (Dorval, Canada).

AuNP Synthesis, PNIPAM Coating and Particle Characterization

All glassware was cleaned with aqua regia prior to use. Trisodium citrate (10 mL, 38.8 mM) was rapidly injected into a refluxing solution of $HAuCl_4*3H_2O$ (100 mL, 1.0 mM) under vigorous stirring. An immediately color change from light yellow to wine red was observed and the reflux was continued for 15 min after which the solution was cooled to rt. The obtained AuNP-seeds (20 mL) were added to a boiling solution of $HAuCl_4*3H_2O$ (2500 mL, 0.296 mM) under vigorous stirring. Subsequently, trisodium citrate (11.2 mL, 38.8 mM) was added and the mixture refluxed for 30 min resulting in a clear color change from wine red to purple. Additional trisodium citrate (100 mL, 38.8 mM) was added as stabilizer and the mixture heated for additional 1 h. The AuNP solution was cooled to rt and SH-PNIPAM$_{3500}$ (40 mg, 11.4 μmol) (6 molecules pr/nm$^2$ AuNP surface area) dissolved in EtOH (5.0 mL) was added. The reaction mixtures stirred overnight at rt (FIG. 11a). The PNIPAM-coated AuNPs was extensively washed with $MQ-H_2O$ and up-concentrated to approx. 2.3 mL (theoretically 65 mg AuNP/mL) by centrifugation (4.500 RPM, 45 min/cycle). The AuNP-seeds, the citrate stabilized AuNPs and the purified up-concentrated PNIPAM-coated AuNP were all characterized by UV-Vis (FIG. 11b), DLS (FIG. 11c) and the ζ-potential was measured (FIG. 11d). The [Au]-concentration of the up-concentration PNIPAM-coated AuNPs were determined by ICP-MS using a Au$^{3+}$-standard (1000 mg/mL) in 5% HCl spiked with 0.5 ppt Ir as internal standard. Up-concentrated PNIPAM-coated AuNPs were dissolved in aqua regia and diluted with 5% HCl to theoretically 666 ppt Au$^{3+}$. The concentration of the PNIPAM-coated AuNPs was determined to 64 mg Au/mL. The PNIPAM coated AuNPs were stored at 5° C. until further use.

Lyophilization of PNIPAM Coated AuNP and Stability in Organic Solvent

PNIPAM coated AuNPs (see synthesis above) were diluted to 1.0-, 2.5- or 5.0 mg Au/mL (500 μL each) with $MQ-H_2O$ and snap-frozen in liquid nitrogen for 2 minutes. The samples were lyophilized overnight (p<6.0×10$^{-2}$ mbar) to form dark colored shiny powders. The lyophilized PNI- PAM coated AuNPs were re-dissolved in EtOH (0.50 mL) and vortexed for a few seconds. The particles completely re-dispersed within seconds to give dark colored solutions. The particle morphology was evaluated by UV-Vis (FIG. 12a) and DLS (FIG. 12b). No sign of aggregation or instability was observed for the PNIPAM-coated AuNPs neither during lyophilization or EtOH solubilization. The lyophilized powder could easily be stored and weighted off at a later time-point.

Example 3

Controlling Particle Retention in SAIB Gels Based on Particle Hydrophobicity

Chemicals were purchased from Sigma-Aldrich Inc. (Brøndby, Denmark) unless otherwise stated. $HAuCl_4 \times 3H_2O$ was purchased from Wako Chemicals GmbH (Neuss, Germany), SH-PNIPAM (MW 3500, PDI=1.24) was purchased from Polymer Source (Dorval, Canada) and MeO-$PEG_{5000}$-SH was purchased from Rapp Polymere GmbH (Tuebingen, Germany).
AuNP Synthesis, $PEG_{5000}$ Coating and Particle Characterization
PEGylated AuNPs ($PEG_{5000}$) were prepared as outlined for the PNIPAM coated AuNP in Example 2 using SH-$PEG_{5000}$ as particle coating polymer. PEGylated particles were characterized by UV-Vis (λ=539 nm) and DLS (59.7±0.9 nm) and the concentration determined by ICP-MS (82.6 mg Au/mL).
In Vitro Release of AuNP from SAIB/EtOH/PLA Gels
Formulations (1000 mg each) consisting of SAIB/EtOH/PLA (75:20:5)+3.0 w % $PNIPAM_{3500}$ or $PEG_{5000}$ coated AuNP was prepared as outlined in the table below.

| Formulation | SAIB | EtOH | PLA | $PNIPAM_{3500}$-AuNP | $PEG_{5000}$-AuNP |
|---|---|---|---|---|---|
| D | 750 mg | 200 mg | 50 mg | 30 mg | — |
| E | 750 mg | 200 mg | 50 mg | — | 30 mg |

The gel components were mixed and homogenized by a ball homogenizer (45 min, 30 s$^{-1}$) to give a clear homogenous solution. AuNPs ($PNIPAM_{3500}$ or $PEG_{5000}$) were transferred into anhydrous EtOH, mixed with the gel solution and vortexed. In vitro release study was carried out by injection of the formulations (3×200 μL each) into MQ-$H_2O$ (10.0 mL for PNIPAM-AuNP) or PBS-containing (for PEG-AuNP) glass vial at 37° C. Small aliquots (1.0 mL) were removed as a function of time and replaced with fresh aqueous solutions. The amount of released AuNPs was measured by correlating the UV-Vis absorbance with a standard curve based on the corresponding particles (FIG. 13). A burst release (20%) of the encapsulated hydrophilic PEGylated particles was observed within the first few hours whereas the more hydrophobic PNIPAM coated AuNP remained encapsulated in the SAIB-amorphous glass matrix due to the enhanced hydrophobic interactions with the gel matrix.

Example 4

Iodo-SAIB Gel Formation with PNIPAM-Coated AuNP In Vitro

Materials Chemicals were purchased from Sigma-Aldrich Inc. (Brøndby, Denmark) unless otherwise stated. $HAuCl_4 \times 3H_2O$ was purchased from Wako Chemicals GmbH (Neuss, Germany) and SH-PNIPAM (MW 3500, PDI=1.24) was purchased from Polymer Source (Dorval, Canada). 6,6'-(2,4,6-triiodophenoxy)acetoxy-isobutyric-sucrose (8) was synthesized as described in Example 1.
AuNP Synthesis, PNIPAM Coating and Particle Characterization
PNIPAM coated AuNPs were prepared as described in Example 2.
Gel Preparation
A formulation consisting of SAIB/8/EtOH (55:25:20)+3.0 w % PNIPAM-AuNP was prepared as outlined in the table below.

| Formulation | SAIB | 6,6'-(2,4,6-triiodophenoxy)-acetoxy-isobutyric-sucrose (8) | EtOH | PNIPAM-AuNPs |
|---|---|---|---|---|
| F SAIB/8/EtOH (55:25:20) + 3.0 w % PNIPAM-AuNP | 165 mg | 75 mg | 60 mg | 9 mg |

SAIB-solution (90 w/w % in EtOH) was weighted off and mixed with 8 (see table above). The mixture were homogenized on a ball-mill homogenizer for 60 min (30 s$^{-1}$) and centrifuged for 20 s at 5000 RPM to remove air bubbles from the formulations. PNIPAM coated AuNPs (141 μL, 64 mg AuNP/mL) was diluted with MQ-$H_2O$ (1659 μL) and lyophilized to give a shinny powder. The lyophilized PNIPAM-coated AuNPs was re-dispersed anhydrous EtOH (52.8 uL) and mixed with the other gel components.
In Vitro Release of AuNP in MQ-$H_2O$
An iodinated gel (200 μL) with 3.0 w % PNIPAM-coated AuNPs (Formulation F) were prepared by injection into a MQ-$H_2O$ (10.0 mL) containing glass vial at 37° C. Small aliquots (1.0 mL) were removed as a function of time and replaced with fresh MQ-$H_2O$. The amount of released AuNPs was measured by correlating the UV-Vis absorbance with a standard curve based on the PNIPAM-coated AuNPs. No release of PNIPAM-coated AuNPs was observed throughout the experiment. Formulation F was a homogenous dark colored solution injectable trough 25 G hypodermic needles.

Example 5

Visualization of Iodo-SAIB Gels Using Ultrasonography In Vitro

Materials
Chemicals were purchased from Sigma-Aldrich Inc. (Brøndby, Denmark) unless otherwise stated. 6,6'-(2,4,6-triiodophenoxy)acetoxy-isobutyric-Sucrose (8) was synthesized as described in Example 1.
Gel Preparation
A formulation consisting of SAIB/8/EtOH (55:25:20) (350 mg) was prepared as described in Example 1 (Formulation B). The iodo-SAIB gel (250 μL) was injected into MQ-$H_2O$ (500 mL) in a glass beaker and the gel was allowed to set for 5 days prior to visualization by ultrasonography. Ultrasound imaging of the iodo-SAIB gel was conducted by an Ultrasound Scanner (BK Medical, Herlev, Denmark) with the following settings: Res/Hz 2/21 Hz, B Gain 83%, Dynamic range 80 dB, Noise reject 10, Noise cutoff 32. The iodo-SAIB gel was clearly visible using ultrasonography as illustrated in FIG. 14.

Example 6

Iodo-SAIB Gels as Injectable CT-Contrast Agent In Vivo—Visibility Study in Immunocompetent Mice Materials Chemicals were purchased from Sigma-Aldrich Inc. (Brøndby, Denmark) unless otherwise stated. 6,6'-(2,4,6-triiodophenoxy)acetoxy-isobutyric-sucrose (8) was synthesized as described in Example 1. Healthy female NMRI (Naval Medical Research Institute) mice were purchased from Taconic (Borup, Denmark).

Gel Preparation

A formulation consisting of SAIB/8/EtOH (55:25:20) (900 mg) was prepared as described in Example 1 (Formulation B).

Animal Setup

Formulation B (SAIB/8/EtOH (55:25:20)) was administrated to healthy female NMRI mice (n=3) by subcutaneous injection (200μ each) under anaesthesia.

MicroCT Imaging of Injectable Iodo-SAIB Gels

The iodinated gels were visualized over time by computed tomography (CT). Images were acquired with a Micro-CAT® II system (Siemens Medical solutions, Malvern, USA). Excellent CT-contrast was achieved using Formulation B (SAIB/8/EtOH (55:25:20)) as illustrated in FIG. 15A-B (CT-images recorded 24 h p.i and 48 p.i.)

Example 7

Iodo-SAIB Gels as Injectable CT-Contrast Agent In Vivo—Long Term Stability and Visibility Study in Immunocompetent Mice Materials Chemicals were purchased from Sigma-Aldrich Inc. (Brøndby, Denmark) unless otherwise stated. 6,6'-(2,4,6-triiodophenoxy)acetoxy-isobutyric-Sucrose (8) was synthesized as described in Example 1. Healthy female NMRI (Naval Medical Research Institute) mice were purchased from Taconic (Borup, Denmark).

Gel Preparation

Formulation consisting of a) SAIB/8/EtOH (65:15:20) (750 mg) and b) SAIB/8/EtOH (50:30:20) (750 mg) were prepared as described in Example 1.

Animal Setup

Both formulations; a) SAIB/8/EtOH (65:15:20) and b) SAIB/8/EtOH (50:30:20) were administrated to healthy female NMRI mice (n=2×8 mice) by subcutaneous injection (50 μL each) under anesthesia.

MicroCT Imaging of Injectable Iodo-SAIB Gels and Post-Implantation Visualization The iodinated gels were visualized over time by computed tomography (CT). Images were acquired with a Micro-CAT® II system (Siemens Medical solutions, Malvern, USA). Excellent CT-contrast was achieved using both formulations: a) SAIB/8/EtOH (65:15:20) and b) SAIB/8/EtOH (50:30:20) as illustrated in FIG. 16A-B. The obtained CT-contrast was found to scale with the formulated amount of iodo-SAIB (8) in the formulation. After 14 w of implantation the animals were sacrificed and the gels removed from the s.q. compartment (FIG. 16C-D). The iodinated gels were well-defined gels that could easily be removed and transferred without disruption of the gels. They were furthermore soft enough to be deformed using a scalpel.

Gelation Kinetics of Injectable Iodo-SAIB Gels

The gelation kinetics of the iodinated gels composed of SAIB/8/EtOH (50:30:20) was monitored by running multiply micro-CT scans within the first few hours of injection (FIG. 17A). Based on these images the total volume of the iodinated gel as a function of time was calculated as illustrated in FIG. 17B. Gelation of the iodinated gel is caused by efflux of EtOH from the gel matrix which takes place within the first two hours p.i. causing a rapid increase in the viscosity of the iodinated gel and an increase of CT-contrast by approximately 35% due to contraction of the gel.

Degradation Profile of Injectable Iodo-SAIB Gels Over 14 w

The degradation profile of iodinated gels composed a) SAIB/8/EtOH (65:15:20) and b) SAIB/8/EtOH (50:30:20) were monitored by microCT scanning over a period of 14 w. Based on these images the total volume of the iodinated gels as a function of time were calculated as illustrated in FIG. 17C. No difference in degradation profile between the two formulations was observed and a steady-state degradation profile was observed for both formulations. A volume loss, with a 95% confidence interval, of −0.09176 μL/day was observed for both formulations after the initial EtOH efflux phase.

Example 8

Iodo-SAIB Gels as Injectable CT-Contrast Agent In Vivo—Visibility Study in Canine with Spontaneous Tumor Materials Chemicals were purchased from Sigma-Aldrich Inc. (Brøndby, Denmark) unless otherwise stated. 6,6'-(2,4,6-triiodophenoxy)acetoxy-isobutyric-Sucrose (8) was synthesized as described in Example 1.

Gel Preparation

A formulation consisting of SAIB/8/EtOH (55:25:20) (350 mg) was prepared as described in Example 1 (Formulation B).

Animal Setup

Formulation B (SAIB/8/EtOH (55:25:20)) was administrated to a companion dog (American Staffordshire terrier, 9 years, 34 kg) with a mast cell tumor present between the front legs. The iodo-SAIB gel was administrated by intratumoral injection (500 μL) using a 25 G needle.

CT Imaging of Injectable Iodo-SAIB Gels in Canine

The iodo-SAIB gel was visualized computed tomography (CT). Images were acquired with a Single slice Siemens CT-scanner (Siemens Medical solutions, Malvern, USA). Excellent CT-contrast was achieved using Formulation B (SAIB/8/EtOH (55:25:20)) as illustrated in FIG. 18 (CT-image recorded 24 h p.i.).

The invention claimed is:

1. An imaging contrast composition for local administration, wherein the imaging contrast composition exhibits contrast properties and wherein at least 60% of an administrated amount of said imaging contrast composition remains more than 24 hours within 10 cm from an injection point when the imaging contrast composition is administrated to a human or animal body, wherein the imaging contrast composition is a liquid before administration and having the ability to transform into a gel after administration, that increases in viscosity by more than 1,000 centipoise (cP) after administration into a human or animal body, and wherein the imaging contrast composition is an X-ray contrast composition comprising an iodinated derivative of sucrose acetate isobutyrate (SAIB) or an iodinated derivative of sucrose acetate isobutyrate (SAIB) doped into sucrose acetate isobutyrate (SAIB), wherein the structure of the iodinated derivative of sucrose acetate isobutyrate (SAIB) is at least one selected from the following:
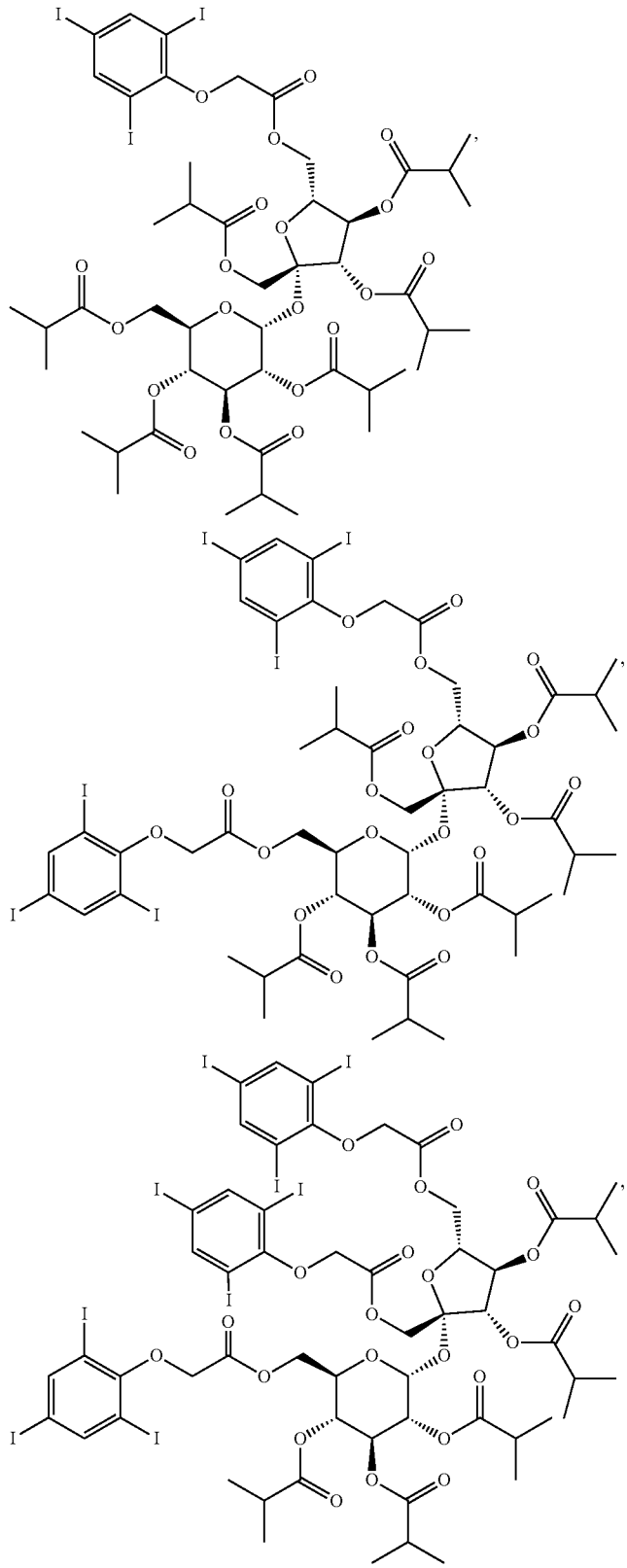

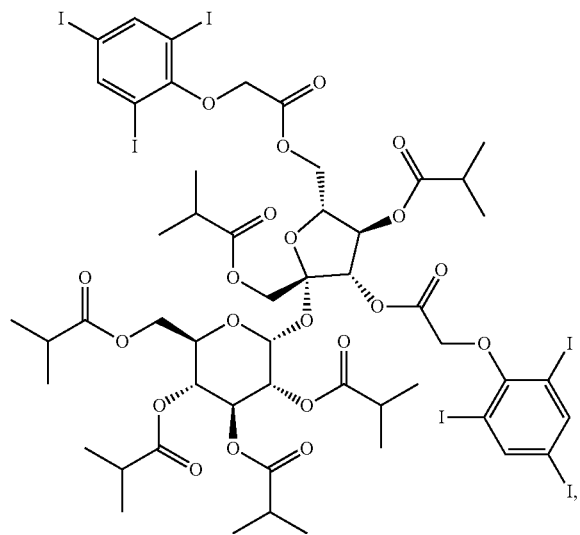
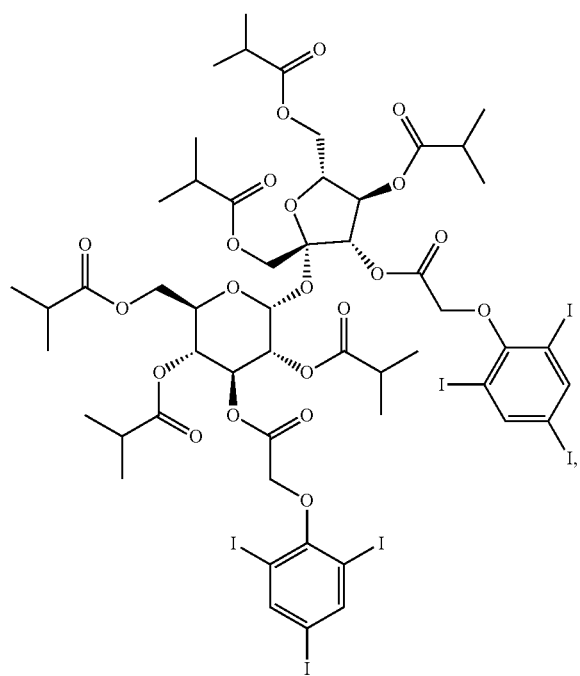

-continued
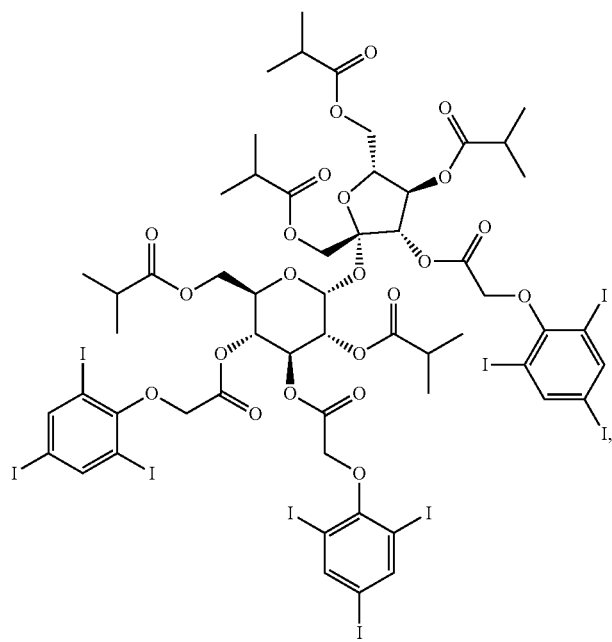
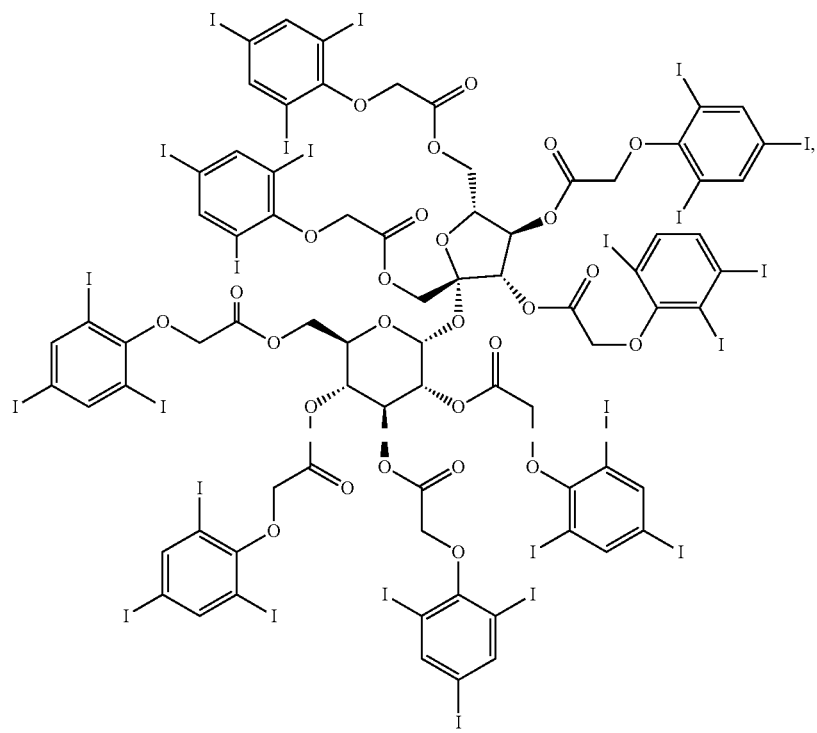

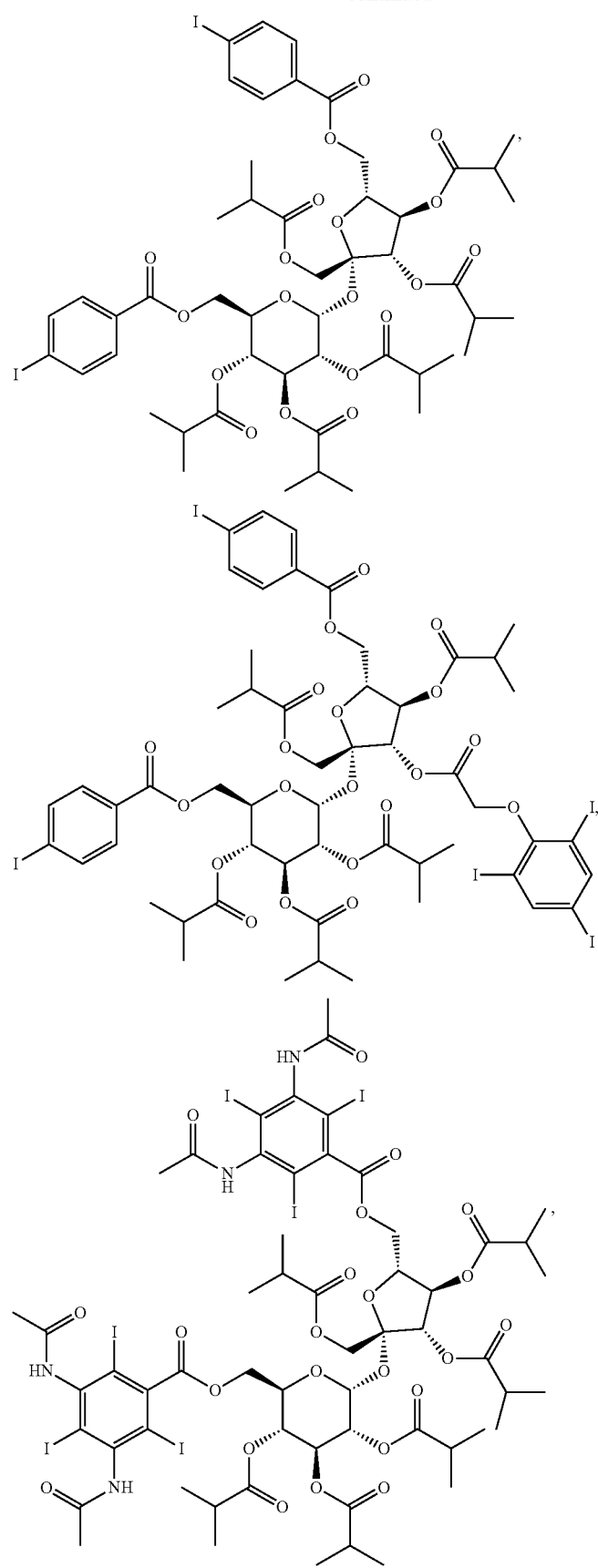

-continued

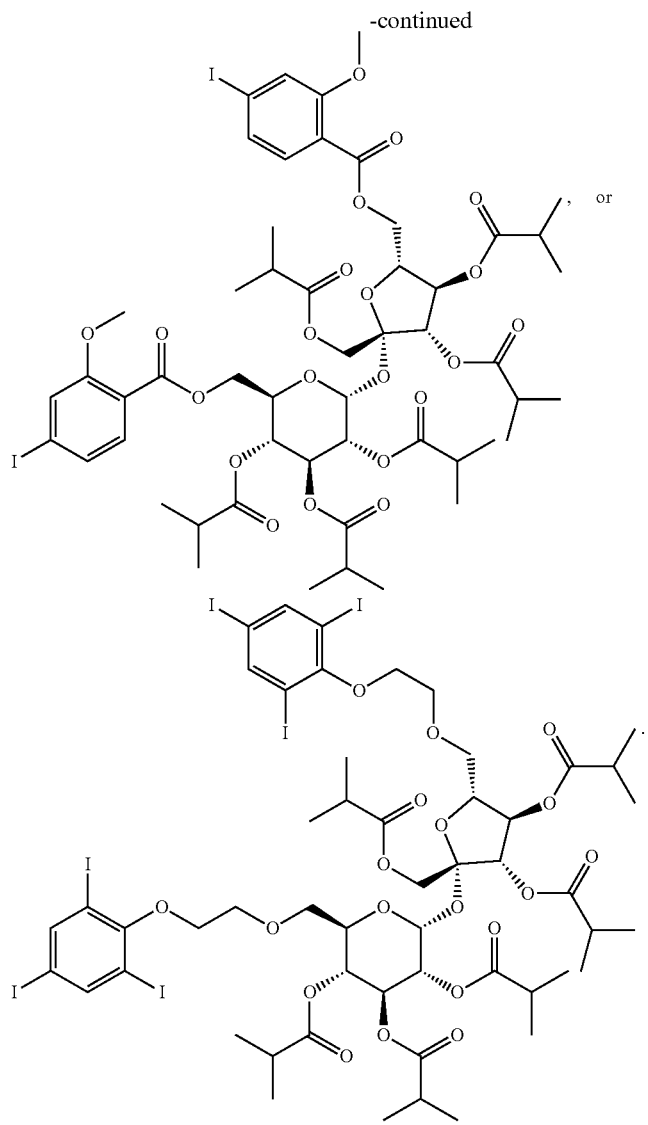

2. The imaging contrast composition according to claim 1, wherein the X-ray contrast composition has a viscosity of less than 10,000 centipoise (cP) at 20° C.

3. The imaging contrast composition according to claim 1, wherein the X-ray contrast composition exhibits gel-formation in response to a temperature in the range of 35 to 40° C., in response to hydration, in response to an ion-concentration in the range of 1 µM to 500 mM, in response to a pH in the range of 6 to 8 and/or in response to contacting with an initiator.

4. The imaging contrast composition according to claim 1, wherein the X-ray contrast composition also comprises; radioactive compounds, paramagnetic compounds, fluorescent compounds or ferromagnetic compounds, or any mixture thereof, and/or wherein the X-ray contrast composition also comprises at least one pharmaceutical substance.

5. The imaging contrast composition according to claim 1, wherein the iodinated derivate of sucrose acetate isobutyrate (SAIB) is solubilized in a mixture of ethanol and sucrose acetate isobutyrate (SAIB).

6. The imaging contrast composition according to claim 1, wherein the X-ray contrast composition comprises a pharmaceutical substance or particle that contains a pharmaceutical substance.

7. The imaging contrast composition according to claim 1, wherein the iodinated derivative of sucrose acetate isobutyrate (SAIB) is solubilised in a mixture of ethanol and sucrose acetate isobutyrate (SAIB) and contains a pharmaceutical substance or a particle that contains a pharmaceutical substance.

8. The imaging contrast composition according to claim 1, for use in radio therapy, imaging, diagnostics, treatment and/or quality rating of radio therapy, for use as a tissue marker and/or for use as a controlled drug release composition.

9. A kit comprising a syringe, a needle used for injection into a body or surgical related procedures, adapted to an open end of said syringe, and the imaging contrast composition according to claim 1.

10. The kit according to claim 9, wherein one of the surgical related procedures is biopsy.

11. A method of recording an X-ray image of the body of a mammal, comprising the steps of a. providing an X-ray contrast composition comprising an organic X-ray agent in a gel-forming system, wherein the X-ray contrast composition is a liquid before administration and having the ability to transform into a gel after administration, that increases in viscosity by more than 1,000 centipoise (cP) after administration into a human or animal body, and wherein the organic X-ray agent comprises an iodinated derivative of sucrose acetate isobutyrate (SAIB) or an iodinated derivative of sucrose acetate isobutyrate (SAIB) doped into sucrose acetate isobutyrate (SAIB), wherein the structure of the iodinated derivative of sucrose acetate isobutyrate (SAIB) is at least one selected from the following:

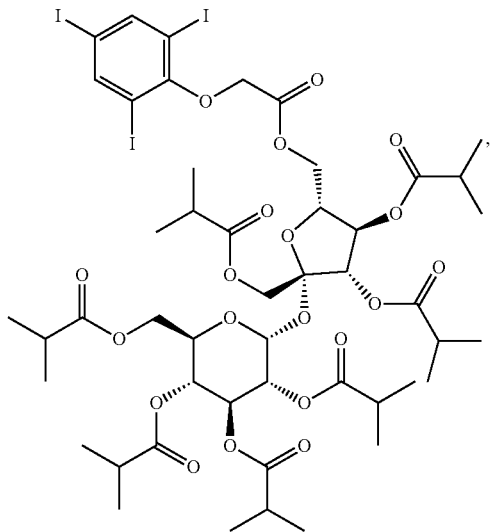

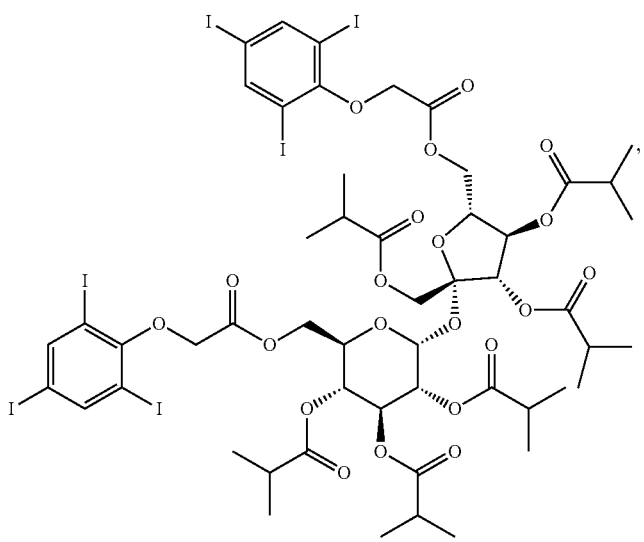 [SMILES: CC(C)C(=O)OC[C@@]1(O[C@H]2O[C@H](COCCOc3c(I)cc(I)cc3I)[C@@H](OC(=O)C(C)C)[C@H](OC(=O)C(C)C)[C@H]2OC(=O)C(C)C)O[C@H](COCCOc2c(I)cc(I)cc2I)[C@@H](OC(=O)C(C)C)[C@@H]1OC(=O)C(C)C]

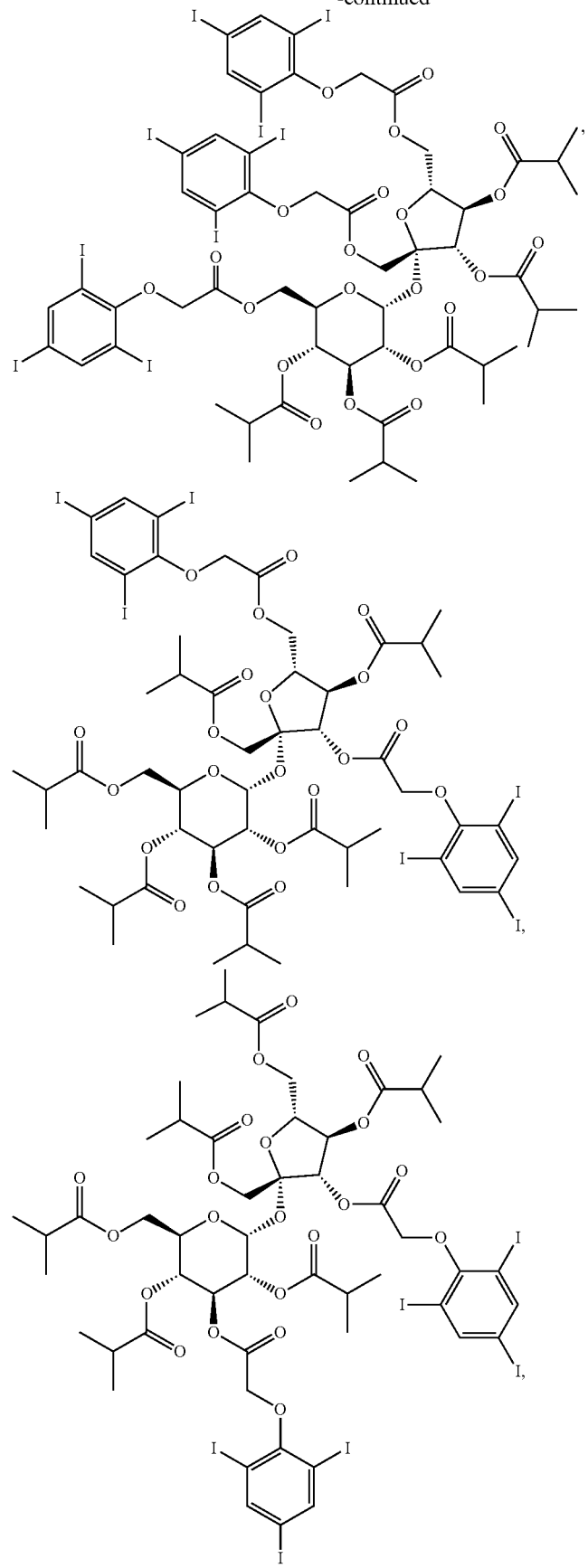

-continued
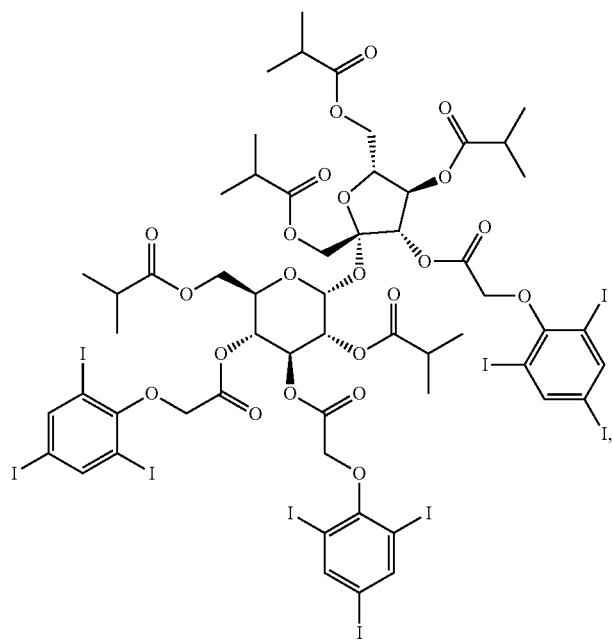
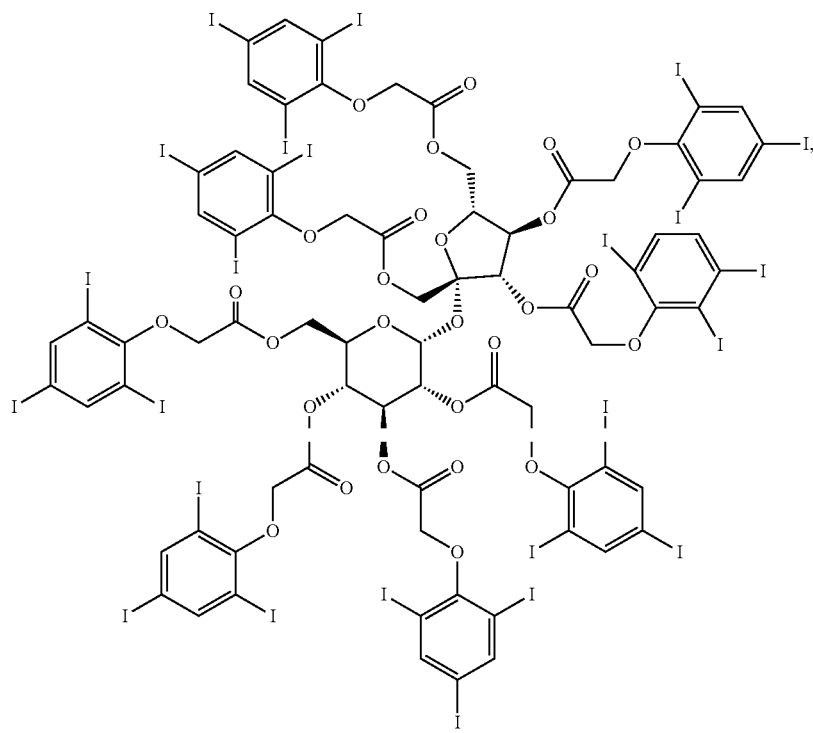

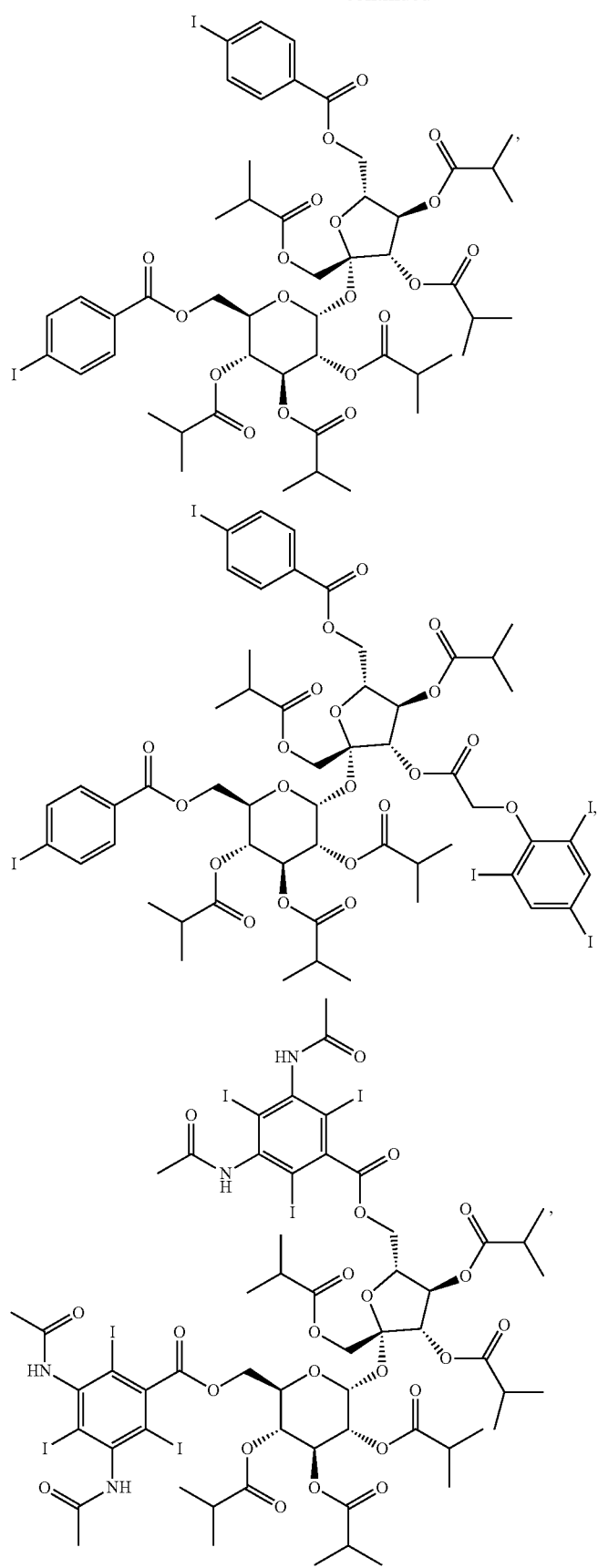

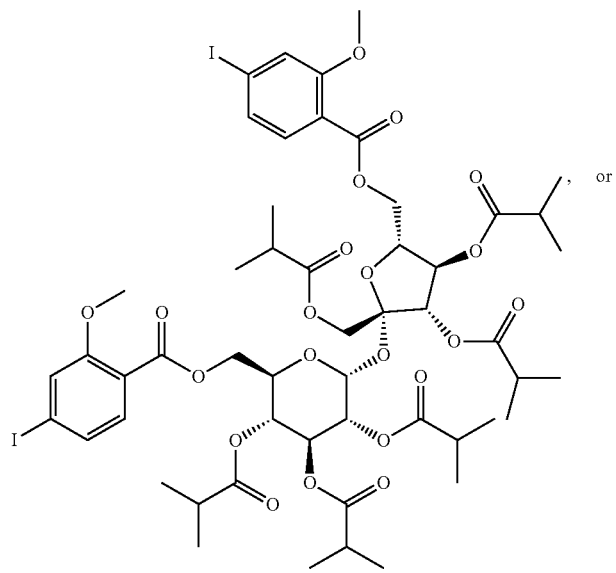

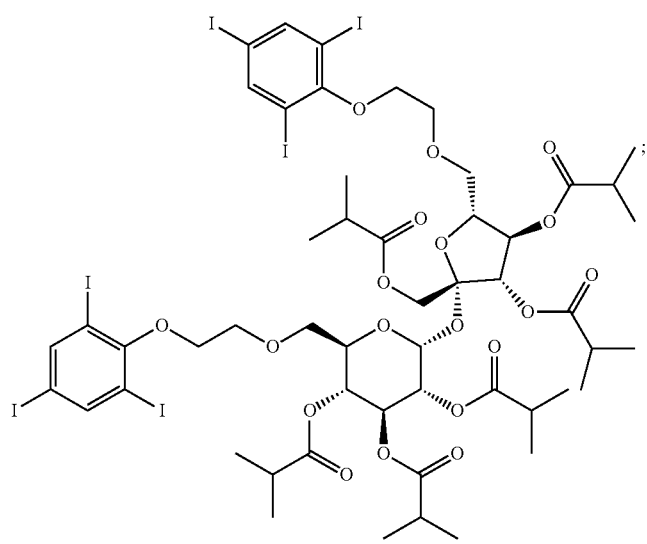 [SMILES: CC(C)C(=O)OC[C@@]1(O[C@H]2O[C@H](COCCOc3c(I)cc(I)cc3I)[C@@H](OC(=O)C(C)C)[C@H](OC(=O)C(C)C)[C@H]2OC(=O)C(C)C)O[C@H](COCCOc2c(I)cc(I)cc2I)[C@@H](OC(=O)C(C)C)[C@@H]1OC(=O)C(C)C]

a. providing an X-ray contrast composition comprising an organic X-ray agent in a gel-forming system, wherein the X-ray contrast composition is a liquid before administration and having the ability to transform into a gel after administration, that increases in viscosity by more than 1,000 centipoise (cP) after administration into a human or animal body, and wherein the organic X-ray agent comprises an iodinated derivative of sucrose acetate isobutyrate (SAIB) or an iodinated derivative of sucrose acetate isobutyrate (SAIB) doped into sucrose acetate isobutyrate (SAIB), wherein the structure of the iodinated derivative of sucrose acetate isobutyrate (SAIB) is at least one selected from the following:

b. administering the X-ray contrast composition to a predetermined location of the mammal, and c. recording X-ray-based images of at least a part of the body of the mammal which comprises the predetermined location.

12. The method according to claim 11, wherein the X-ray contrast composition is parenterally administered to a predetermined location of the body of said mammal, and wherein an X-ray image of at least a part of the body of the mammal including the predetermined location is recorded.

13. A method of joint radiotherapy and X-ray imaging of a target tissue in a mammal, comprising the steps of

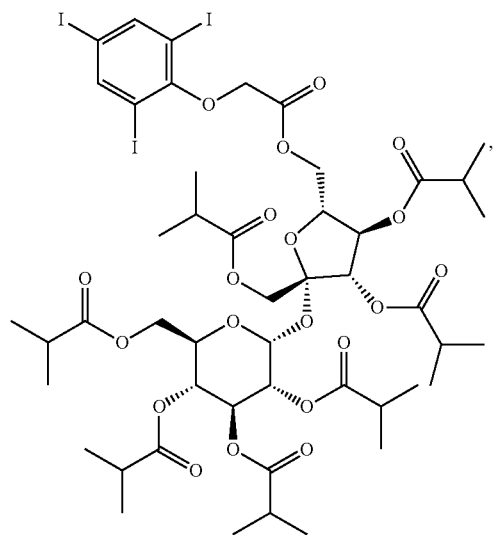
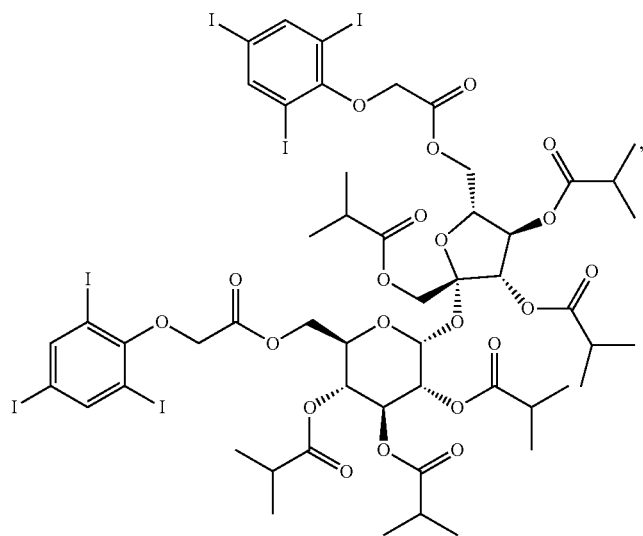 [SMILES: CC(C)C(=O)OC[C@@]1(O[C@H]2O[C@H](COCCOc3c(I)cc(I)cc3I)[C@@H](OC(=O)C(C)C)[C@H](OC(=O)C(C)C)[C@H]2OC(=O)C(C)C)O[C@H](COCCOc2c(I)cc(I)cc2I)[C@@H](OC(=O)C(C)C)[C@@H]1OC(=O)C(C)C]
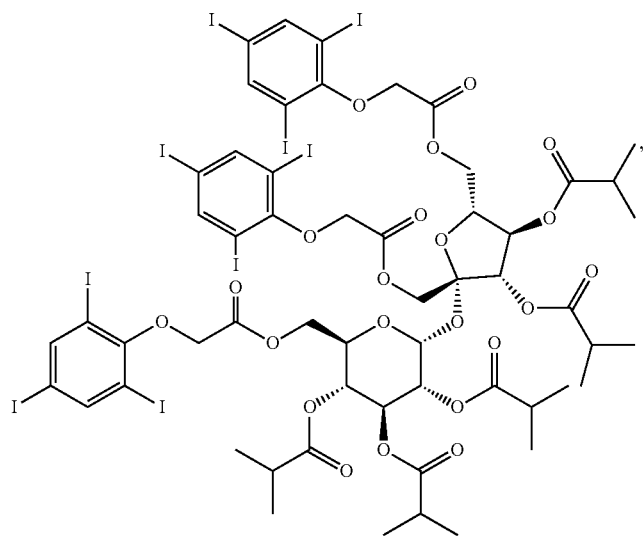

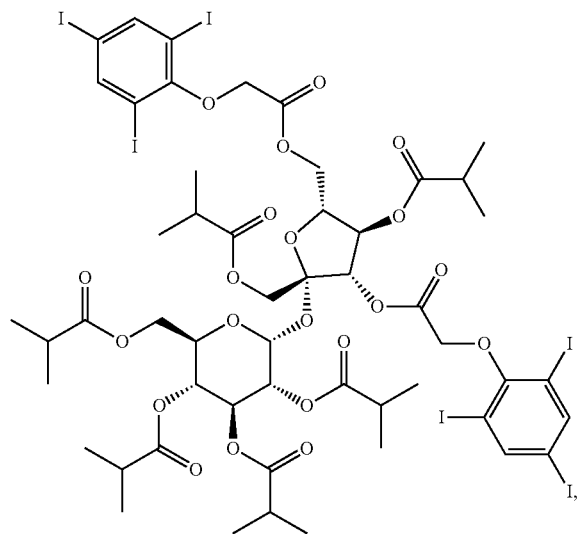
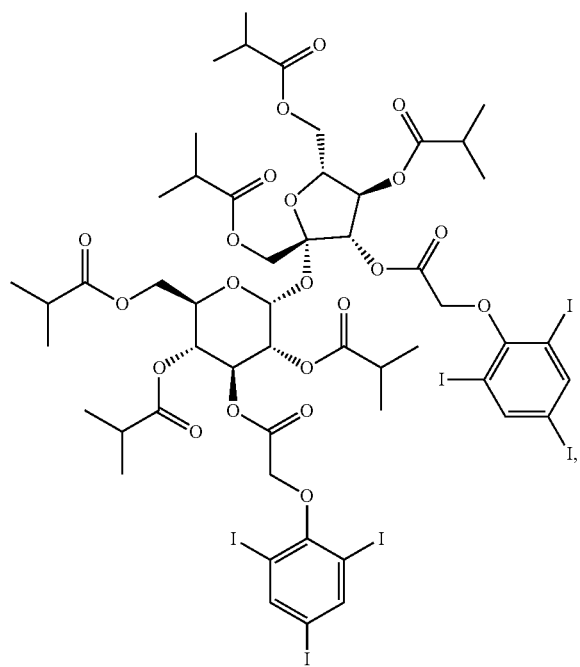

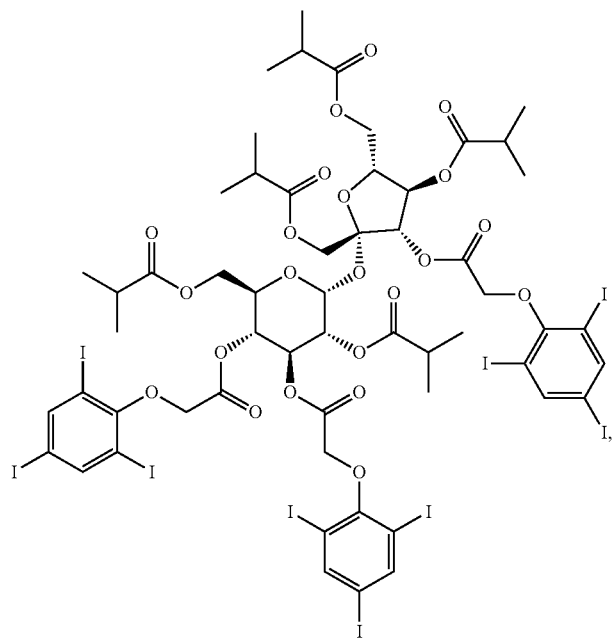
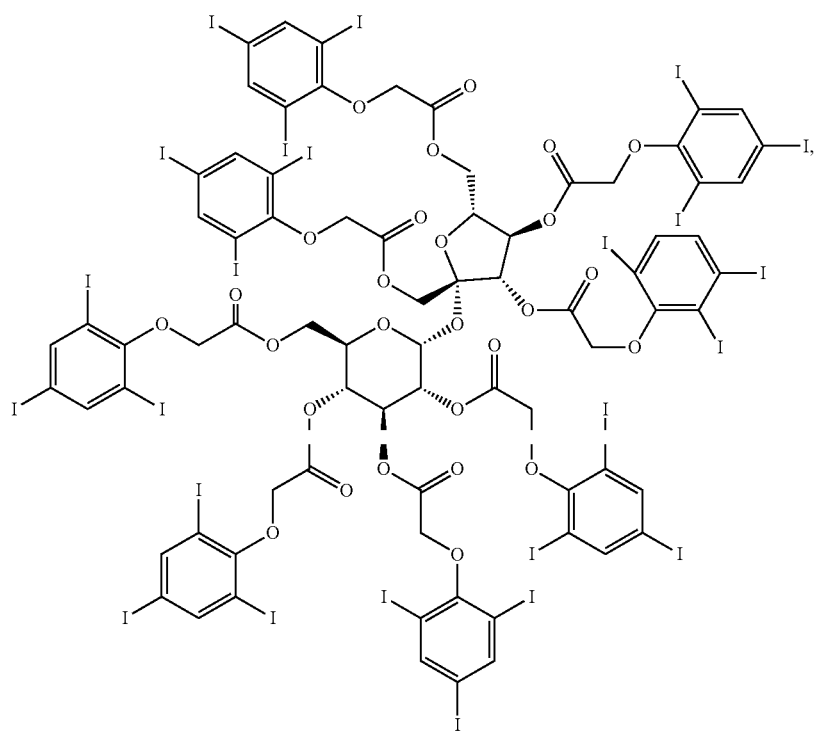

-continued
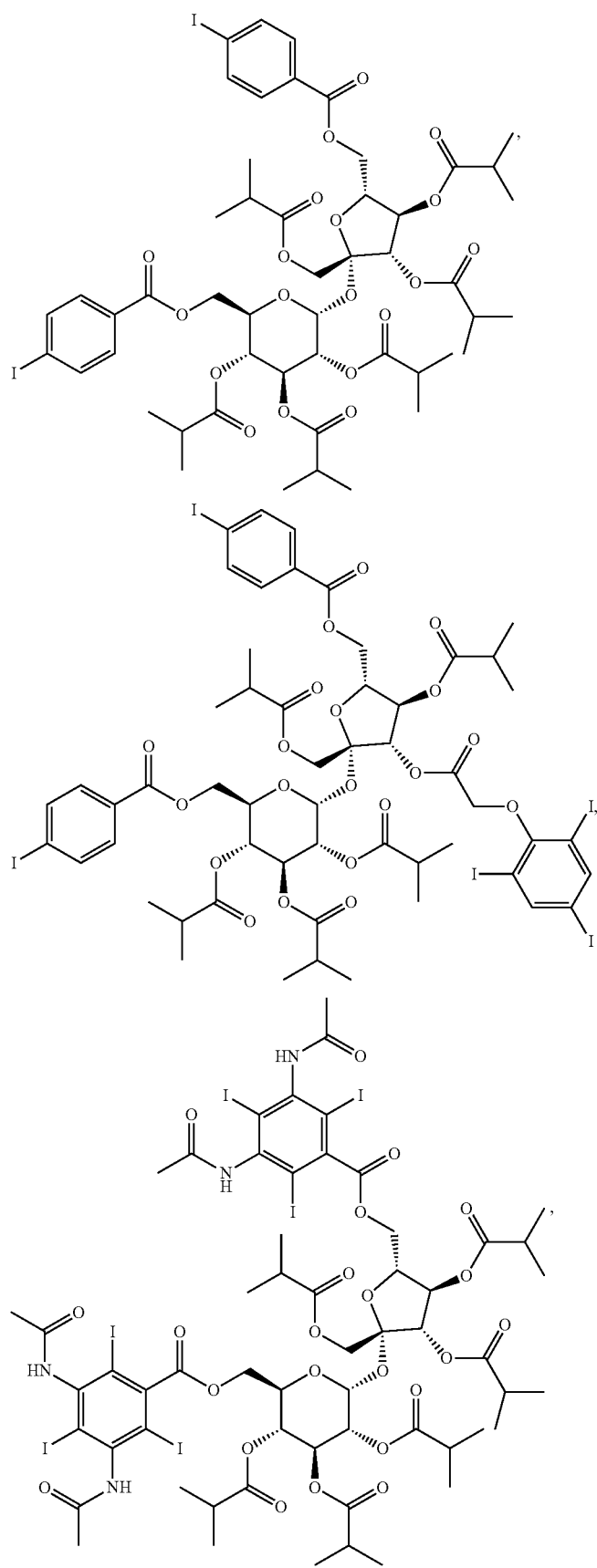

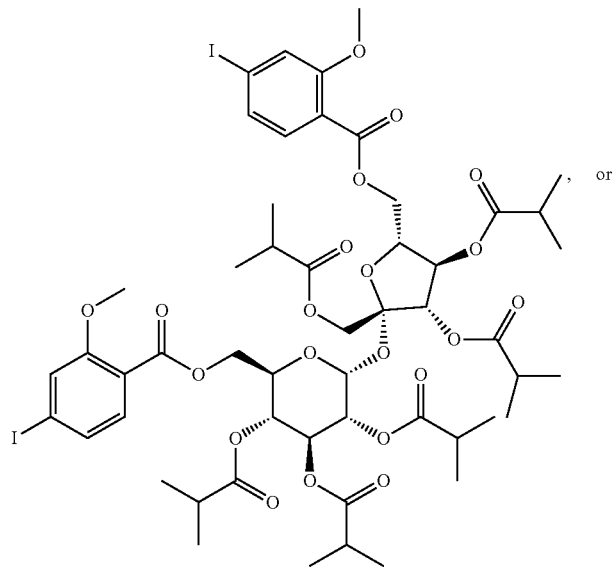

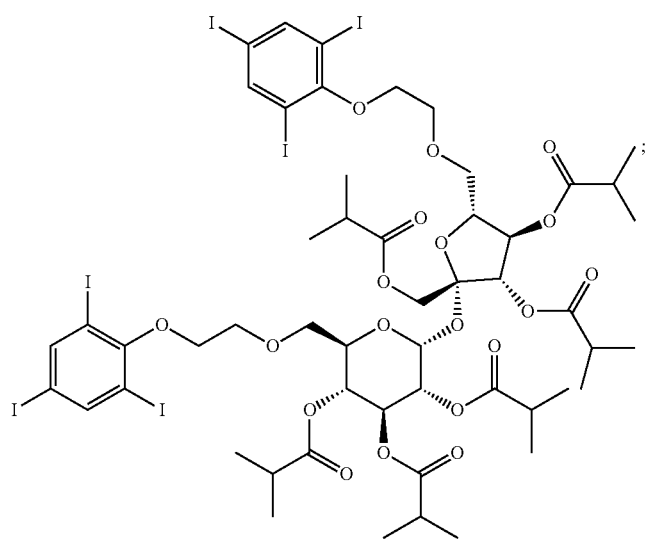 [SMILES: CC(C)C(=O)OC[C@@]1(O[C@H]2O[C@H](COCCOc3c(I)cc(I)cc3I)[C@@H](OC(=O)C(C)C)[C@H](OC(=O)C(C)C)[C@H]2OC(=O)C(C)C)O[C@H](COCCOc2c(I)cc(I)cc2I)[C@@H](OC(=O)C(C)C)[C@@H]1OC(=O)C(C)C]

b. administering the X-ray contrast composition to a predetermined target tissue of the mammal,
c. recording X-ray-based images, of at least a part of the body of the mammal which comprises the target tissue, thereby providing a definition of the target tissue, and
d. using the definition of the target tissue obtained in c) to direct external beam radiotherapy to the target tissue.

14. A method for directing local administration of a pharmaceutically active agent to a target tissue in a mammal, comprising the steps of
a. providing an X-ray contrast composition comprising an organic X-ray agent and an active pharmaceutical agent in a gel-forming system, wherein the X-ray contrast composition is a liquid before administration and having the ability to transform into a gel after administration, that increases in viscosity by more than 1,000 centipoise (cP) after administration into a human or animal body, and wherein the organic X-ray agent comprises an iodinated derivative of sucrose acetate isobutyrate (SAIB) or an iodinated derivative of sucrose acetate isobutyrate (SAIB) doped into sucrose acetate isobutyrate (SAIB), wherein the structure of the iodinated derivative of sucrose acetate isobutyrate (SAIB) is at least one selected from the following:

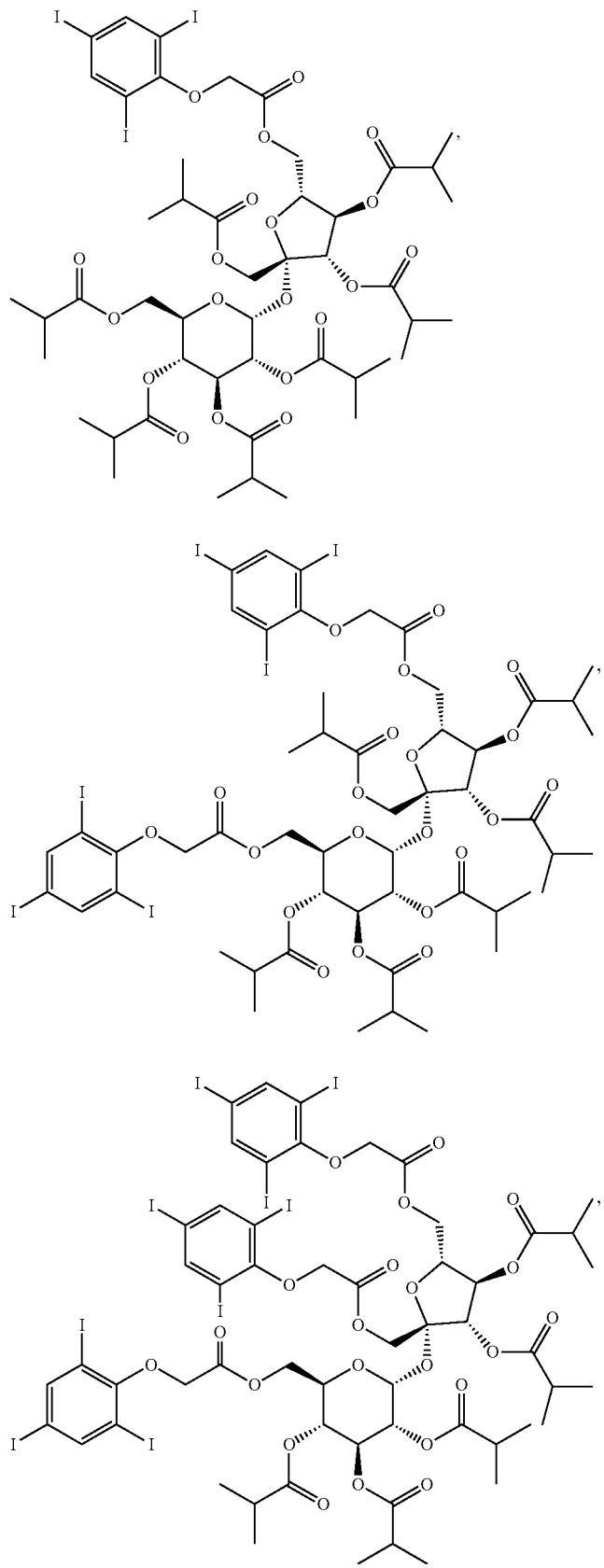

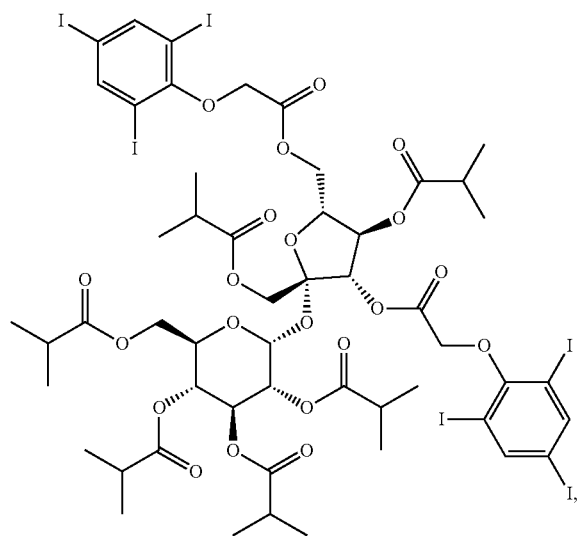
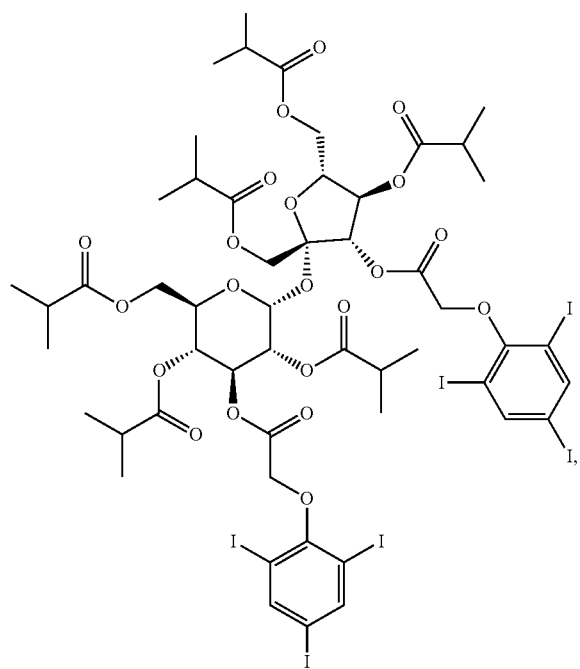

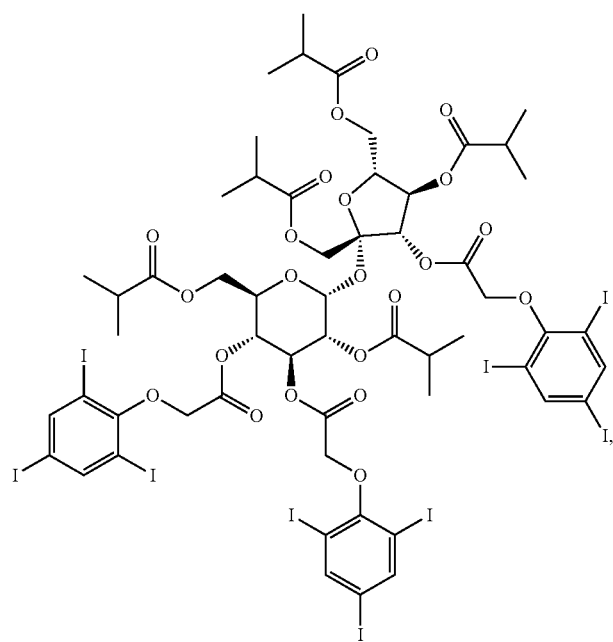
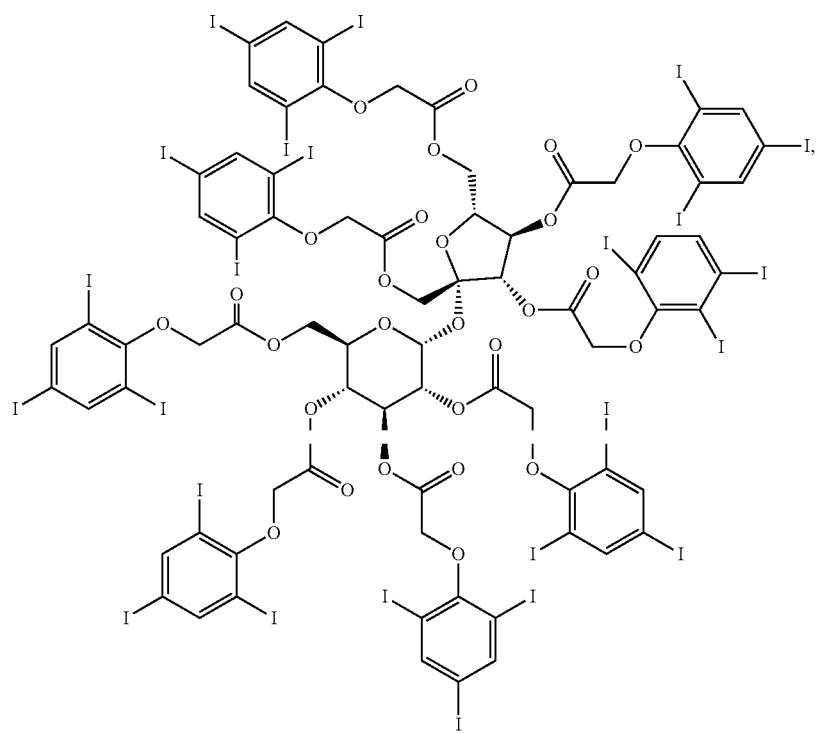

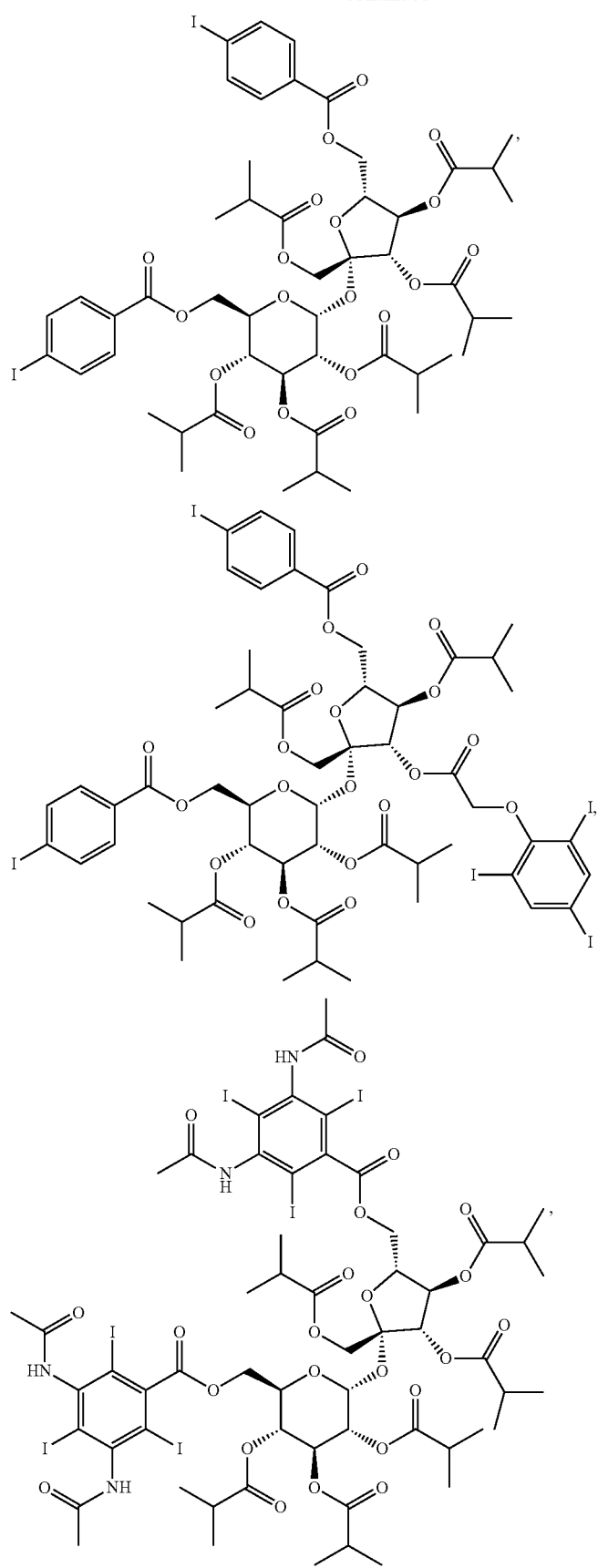

-continued

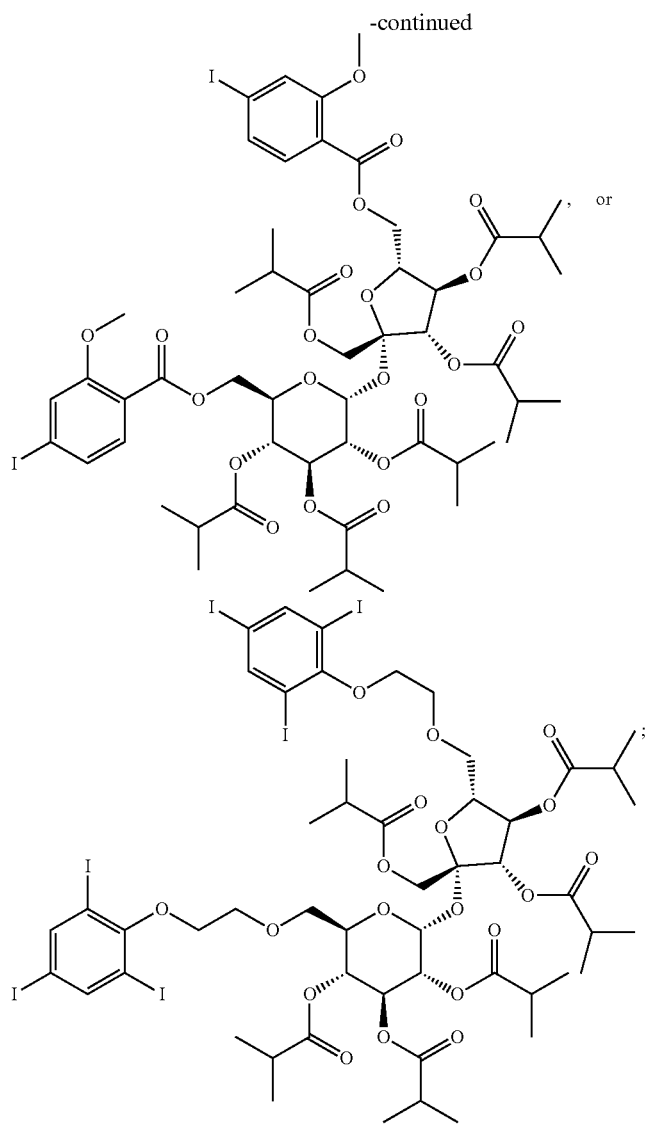

, or

;

b. administering the X-ray contrast composition to a predetermined target tissue of the mammal,
c. recording X-ray-based images, of at least a part of the body of the mammal which comprises the target tissue, thereby providing a definition of the target tissue, and
d. using the X-ray contrast composition in b) for delivery of the active pharmaceutical agent to a predetermined target tissue of the mammal.

15. The method according to any one of claims 13 and 14, wherein the target tissue comprises tumor cells.

16. The method according to any one of claims 11 to 14, wherein the X-ray contrast composition comprises the feature of exhibiting contrast properties and wherein at least 60% of an administrated amount of the X-ray contrast composition remains more than 24 hours within 10 cm from an injection point when the X-ray contrast composition is administrated to the mammal.

* * * * *